(12) United States Patent
Smith et al.

(10) Patent No.: US 12,005,067 B2
(45) Date of Patent: Jun. 11, 2024

(54) JAK INHIBITOR WITH A VITAMIN D ANALOG FOR TREATMENT OF SKIN DISEASES

(71) Applicant: INCYTE CORPORATION, Wilmington, DE (US)

(72) Inventors: Paul Smith, Wilmington, DE (US); Zheng Zhang, Wilmington, DE (US); Melissa Parker, Wilmington, DE (US); James Fidge, Guildford (GB)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 17/541,601

(22) Filed: Dec. 3, 2021

(65) Prior Publication Data

US 2022/0202834 A1   Jun. 30, 2022

Related U.S. Application Data

(60) Provisional application No. 63/199,876, filed on Jan. 29, 2021, provisional application No. 63/121,531, filed on Dec. 4, 2020.

(51) Int. Cl.
| | | |
|---|---|---|
| *A61K 31/593* | (2006.01) | |
| *A61K 31/519* | (2006.01) | |
| *A61K 45/06* | (2006.01) | |
| *A61P 17/06* | (2006.01) | |

(52) U.S. Cl.
CPC .......... *A61K 31/593* (2013.01); *A61K 31/519* (2013.01); *A61K 45/06* (2013.01); *A61P 17/06* (2018.01)

(58) Field of Classification Search
CPC ..... A61P 17/06; A61K 31/519; A61K 31/593; A61K 45/06
See application file for complete search history.

(56) References Cited

FOREIGN PATENT DOCUMENTS

| WO | WO 2020/222187 | * | 11/2020 | ......... A61K 31/4174 |
|---|---|---|---|---|
| WO | WO 2022/038365 | * | 2/2022 | ............. C07C 69/60 |

* cited by examiner

*Primary Examiner* — Erich A Leeser
(74) *Attorney, Agent, or Firm* — Finnegan, Henderson, Farabow, Garrett & Dunner, LLP

(57) ABSTRACT

The present disclosure relates to topical treatment of skin diseases, such as psoriasis, atopic dermatitis, alopecia, vitiligo, Reiter's syndrome, pityriasis rubra pilaris, epidermolysis bullosa simplex, palmoplantar keratoderma, pachyonychia congenita, steatocystoma multiplex, cutaneous lichen planus, cutaneous T-cell lymphoma, hidradenitis suppurativa, contact dermatitis, ichthyosis, and a disorder of keratinization, using (a) a JAK inhibitor, or a pharmaceutically acceptable salt thereof, and (b) vitamin D3, a vitamin D3 analog, or a pharmaceutically acceptable salt thereof.

21 Claims, 10 Drawing Sheets

Compound concentration: concentrations of ruxolitinib, calcipotriol, or a combination of thereof;
Calcip = Calcipotriol; Rux = Ruxolitinib; Combinations = Calcipotriol + Ruxolitinib; MMP12 = Matrix metalloproteinase 12;
Fold change = increase expression over normal (healthy) unstimulated human skin;
Mean + S.E.M: *P<0.05; P<0.01; *P<0.001; ****P<0.0001

Compound concentration: concentrations of ruxolitinib, calcipotriol, or a combination of thereof;
Calcip = Calcipotriol; Rux = Ruxolitinib; Combinations = Calcipotriol + Ruxolitinib;
MMP12 = Matrix metalloproteinase 12;
Fold change = increase expression over normal (healthy) unstimulated human skin;
Mean + S.E.M: *P<0.05; P<0.01; *P<0.001; ****P<0.0001

Compound concentration (nM)

Compound concentration: concentrations of ruxolitinib, calcipotriol, or a combination of thereof;
Calcip = Calcipotriol; Rux = Ruxolitinib; Combinations = Calcipotriol + Ruxolitinib;
MMP12 = Matrix metalloproteinase 12;
Fold change = increase expression over normal (healthy) unstimulated human skin;
Mean + S.E.M: *$P<0.05$; $P<0.01$; *$P<0.001$; ****$P<0.0001$

FIG. 6A

| Th1 Stim | Treatment Group | | |
|---|---|---|---|
| Gene | Vitamin D Analog | JAK inhibitor | JAKi + Vit D Combo |
| CAMP | | | |
| CCL17 | | | |
| DefB4a | | | |
| FLG | | | |
| IFNg | | | |
| IL17A | | | |
| IL22 | | | |
| IL31 | | | |
| IL33 | | | |
| LOR | | | |
| MMP12 | | | |
| S100a12 | | | |
| SerpinB4 | | | |
| TNFSF18 | | | |
| TSLP | | | |

FIG. 6B

| Th17 Stim | Treatment Group | | |
|---|---|---|---|
| Gene | Vitamin D Analog | JAK inhibitor | JAK + Vit D Combo |
| CAMP | | | |
| CCL17 | | | |
| CCL22 | | | |
| DefB4a | | | |
| FLG | | | |
| IFNg | | | |
| IL17A | | | |
| IL17F | | | |
| IL22 | | | |
| IL31 | | | |
| IL4 | | | |
| MMP12 | | | |
| S100a12 | | | |
| TNFSF18 | | | |
| TSLP | | | |

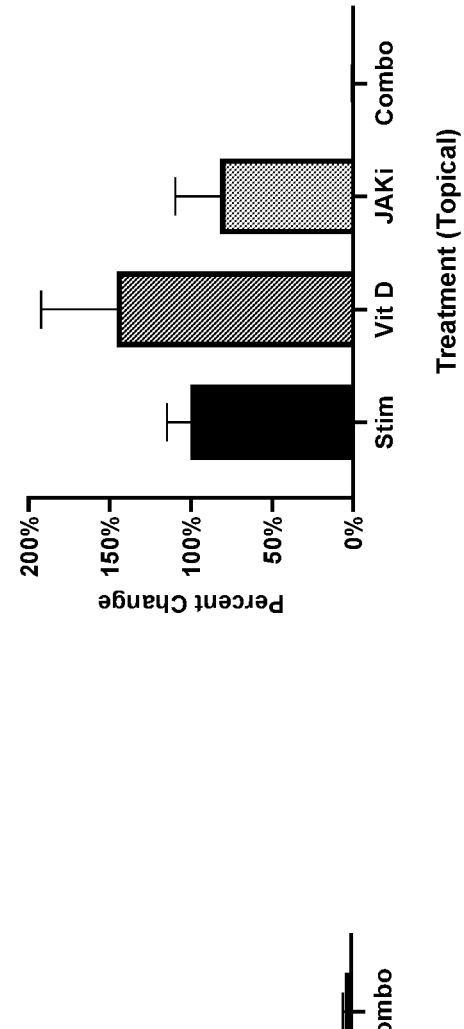
FIG. 8A *S100a12*
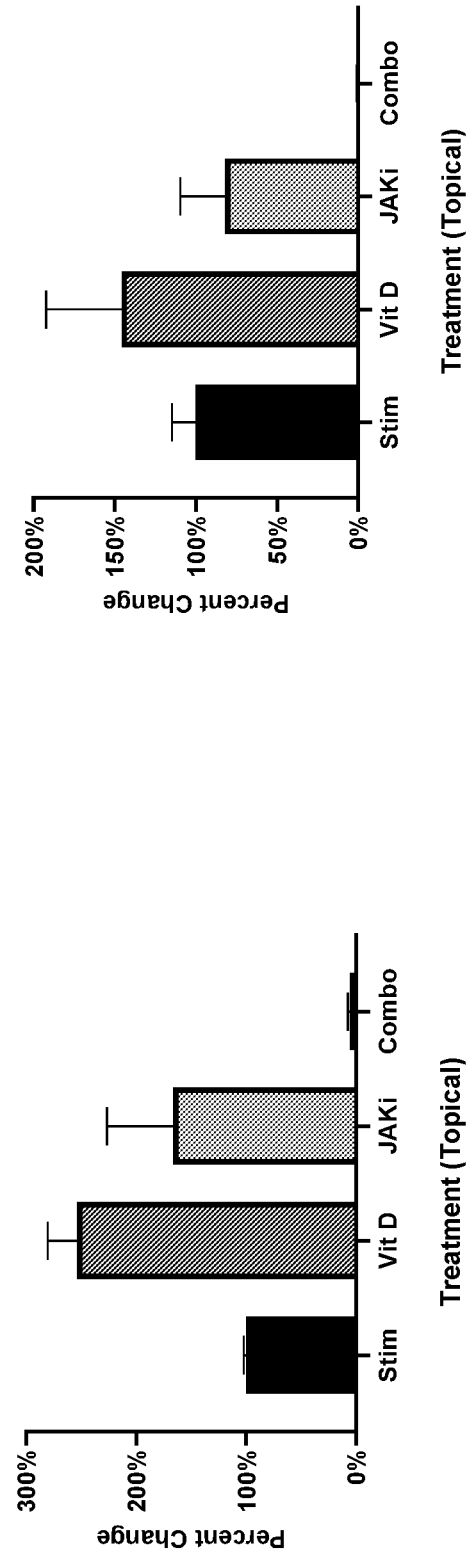
FIG. 8B *Defb4*
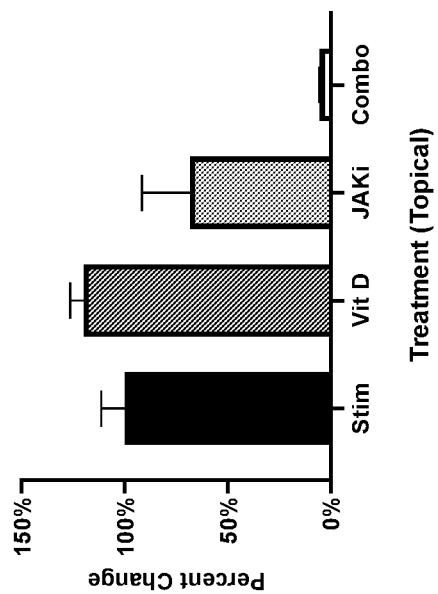
FIG. 8C *Serpinb4*

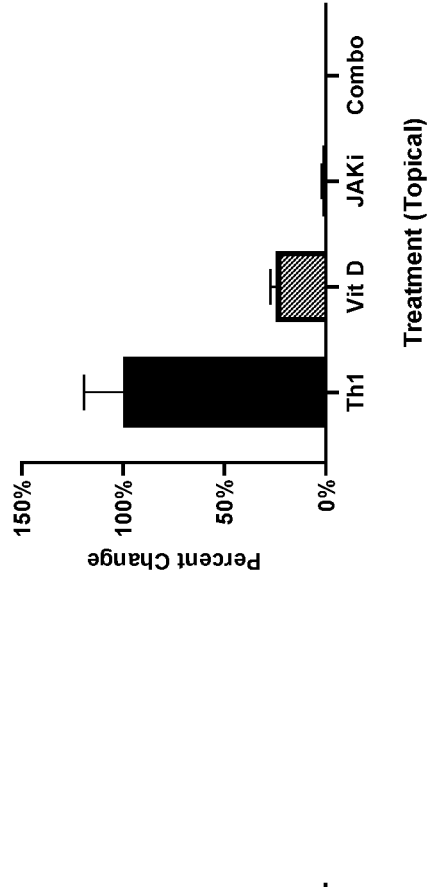
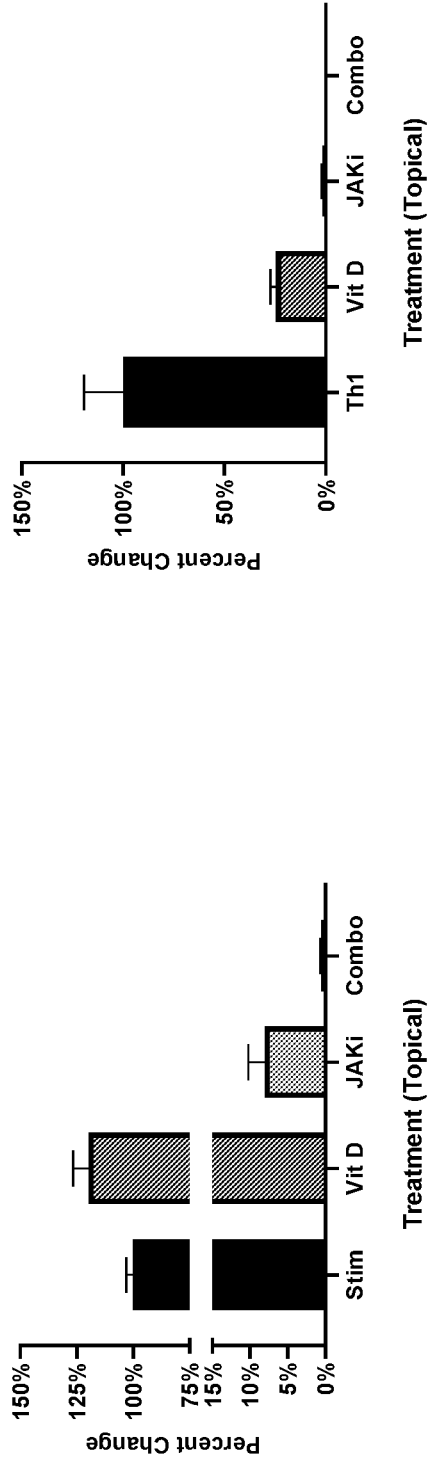
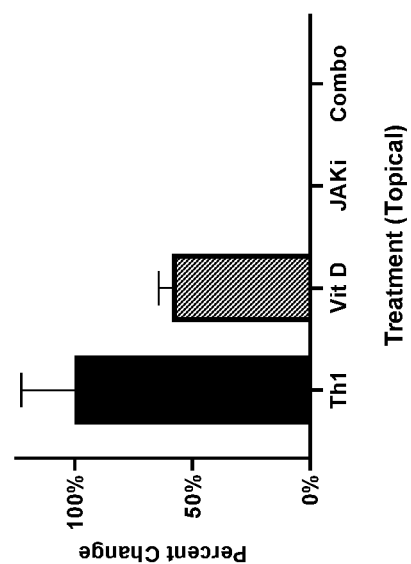

JAK INHIBITOR WITH A VITAMIN D ANALOG FOR TREATMENT OF SKIN DISEASES

CROSS REFERENCE TO RELATED APPLICATIONS

This application claims priority to U.S. Provisional Application No. 63/121,531, filed Dec. 4, 2020, and U.S. Provisional Application No. 63/199,876, filed Jan. 29, 2021, each of which is hereby incorporated by reference in its entirety.

TECHNICAL FIELD

The present disclosure relates to topical treatment of skin diseases using (a) a JAK inhibitor, or a pharmaceutically acceptable salt thereof, and (b) vitamin D3, a vitamin D3 analog, or a pharmaceutically acceptable salt thereof.

BACKGROUND

Inflammation mediated by the Janus kinase (JAK)-signal transducer is one of the important characteristics of autoimmune skin diseases. Janus kinase (JAK) inhibitors have been developed as agents for the treatment of inflammatory skin diseases including atopic dermatitis, alopecia areata, psoriasis, and vitiligo. However, as for any therapeutic, JAK inhibitors may not be equally effective in all subjects that have an inflammatory skin disease. There is a need for developing more effective formulations comprising JAK inhibitors to treat a broader number of subjects with various inflammatory skin disease.

Considering these limitations, there is a medical need for new therapeutic options. The present disclosure is directed to that need and others.

SUMMARY

The present disclosure provides methods of treating skin disease in a patient in need thereof, comprising topically administering to an affected area of the patient (a) a JAK inhibitor, or a pharmaceutically acceptable salt thereof, and (b) vitamin D3, a vitamin D3 analog, or a pharmaceutically acceptable salt thereof.

The present disclosure also provides methods of treating skin disease a patient in need thereof, comprising topically administering to an affected area of the patient (a) ruxolitinib, or a pharmaceutically acceptable salt thereof, and (b) vitamin D3, a vitamin D3 analog, or a pharmaceutically acceptable salt thereof.

The present disclosure also provides methods of treating skin disease in a patient in need thereof, comprising topically administering to an affected area of the patient (a) ruxolitinib, or a pharmaceutically acceptable salt thereof, and (b) calcipotriol, or a pharmaceutically acceptable salt thereof to patients.

The present disclosure also provides a JAK inhibitor, or a pharmaceutically acceptable salt thereof, for use in topical treatment of a skin disease described herein in combination with a vitamin D3, a vitamin D3 analog, or a pharmaceutically acceptable salt thereof.

The present disclosure also provides ruxolitinib, or a pharmaceutically acceptable salt thereof, for use in topical treatment of a skin disease described herein in combination with a vitamin D3, a vitamin D3 analog, or a pharmaceutically acceptable salt thereof.

The present disclosure also provides ruxolitinib, or a pharmaceutically acceptable salt thereof, for use in topical treatment of a skin disease described herein in combination with calcipotriol, or a pharmaceutically acceptable salt thereof.

The present disclosure also provides use of a JAK inhibitor, or a pharmaceutically acceptable salt thereof, for manufacture of a medicament for topical treatment of a skin disease described herein in combination with a vitamin D3, a vitamin D3 analog, or a pharmaceutically acceptable salt thereof.

The present disclosure also provides use of ruxolitinib, or a pharmaceutically acceptable salt thereof, for manufacture of a medicament for topical treatment of a skin disease described herein in combination with a vitamin D3, a vitamin D3 analog, or a pharmaceutically acceptable salt thereof.

The present disclosure also provides use of ruxolitinib, or a pharmaceutically acceptable salt thereof, for manufacture of a medicament for topical treatment of a skin disease described herein in combination with calcipotriol, or a pharmaceutically acceptable salt thereof.

In some embodiments of each of the aforementioned, the patient is a human patient.

The present disclosure further provides a topical formulation comprising (a) a JAK inhibitor, or a pharmaceutically acceptable salt thereof, and (b) vitamin D3, a vitamin D3 analog, or a pharmaceutically acceptable salt thereof, for use in topical treatment of a skin disorder described herein.

The present disclosure further provides a topical formulation comprising (a) ruxolitinib, or a pharmaceutically acceptable salt thereof, and (b) vitamin D3, a vitamin D3 analog, or a pharmaceutically acceptable salt thereof for use in topical treatment of a skin disorder described herein.

The present disclosure further provides ruxolitinib topical formulation comprising (a) ruxolitinib, or a pharmaceutically acceptable salt thereof, and (b) calcipotriol, or a pharmaceutically acceptable salt thereof for use in topical treatment of a skin disorder described herein.

The present disclosure also provides use of a topical formulation comprising (a) a JAK inhibitor, or a pharmaceutically acceptable salt thereof, and (b) vitamin D3, a vitamin D3 analog, or a pharmaceutically acceptable salt thereof for manufacture of a medicament for use in topical treatment of a skin disorder described herein.

The present disclosure also provides use of a topical formulation comprising (a) ruxolitinib, or a pharmaceutically acceptable salt thereof, and (b) vitamin D3, a vitamin D3 analog, or a pharmaceutically acceptable salt thereof for manufacture of a medicament for use in topical treatment of a skin disorder described herein.

The present disclosure also provides use of a topical formulation comprising (a) ruxolitinib, or a pharmaceutically acceptable salt thereof, and (b) calcipotriol, or a pharmaceutically acceptable salt thereof for manufacture of a medicament for use in topical treatment of a skin disorder described herein.

The present disclosure further provides pharmaceutical formulations for topical treatment of a skin disease comprising (a) a JAK inhibitor, or a pharmaceutically acceptable salt thereof, and (b) vitamin D3, a vitamin D3 analog, or a pharmaceutically acceptable salt thereof.

The present disclosure also provides pharmaceutical formulations for topical treatment of a skin disease, comprising (a) ruxolitinib, or a pharmaceutically acceptable salt thereof, and (b) vitamin D3, a vitamin D3 analog, or a pharmaceutically acceptable salt thereof.

The present disclosure further provides pharmaceutical formulations for topical treatment of a skin disease, comprising (a) ruxolitinib phosphate, or a pharmaceutically acceptable salt thereof, and (b) vitamin D3, a vitamin D3 analog, or a pharmaceutically acceptable salt thereof.

The details of one or more embodiments of the present disclosure are set forth in the description below. Other features, objects, and advantages of the present disclosure will be apparent from the description and drawings, and from the claims.

BRIEF DESCRIPTION OF THE DRAWINGS

FIGS. 6A-6B depicts the absolute fold change in certain gene expression after treatment with combinations of calcipotriol and ruxolitinib as compared to untreated control after Th1 or Th17 stimulation, respectively (white indicates <2 absolute fold change, grey indicates >2 absolute fold change, and black indicates >4 absolute fold change).

FIGS. 8A-8C depicts fold changes (with mean+SEM) of S100a12, Defb4, and Serpinb5, respectively of the skins treated topically with various concentrations of ruxolitinib, calcipotriol, and a combination of thereof at 24 hours following stimulation over normal (healthy) unstimulated and stimulated human skins (JAKi is ruxolitinib; Vit D is calcipotriol).

FIGS. 9A-9C depicts fold changes (with mean+SEM) of MMP12, IL-22, and CXCL10, respectively of the skins treated topically with various concentrations of ruxolitinib, calcipotriol, and a combination of thereof at 24 hours following stimulation over normal (healthy) unstimulated and stimulated human skins (JAKi is ruxolitinib; Vit D is calcipotriol).

DETAILED DESCRIPTION

Figure 1:
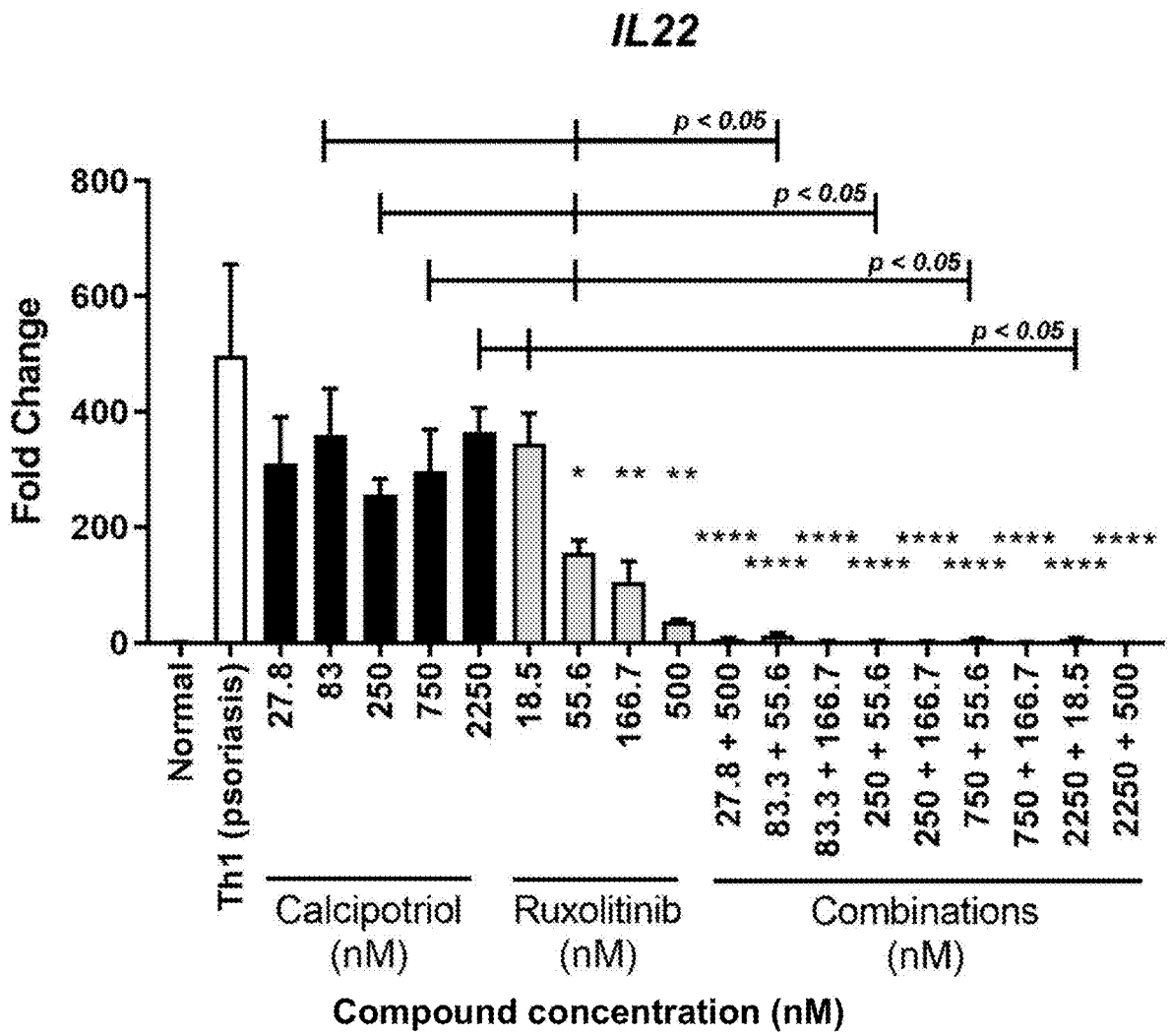
FIG. 1 depicts fold changes and p-values of IL-22 levels of the skins treated basolaterally with various concentrations of ruxolitinib, calcipotriol, and a combination of thereof at 24 hours following stimulation over normal (healthy) unstimulated and stimulated human skins.

The present disclosure provides methods of treating a skin disease in a patient in need thereof, comprising topically administering to an affected area of the patient (a) a JAK inhibitor, or a pharmaceutically acceptable salt thereof, and (b) a vitamin D derivative, or a pharmaceutically acceptable salt thereof.

The present disclosure provides methods of treating a skin disease in a patient in need thereof, comprising topically administering to an affected area of the patient (a) a JAK inhibitor, or a pharmaceutically acceptable salt thereof, and (b) vitamin D3, a vitamin D3 analog, or a pharmaceutically acceptable salt thereof.

The present disclosure also provides methods of treating a skin disease in a patient in need thereof, comprising topically administering to an affected area of the patient (a) a JAK inhibitor, or a pharmaceutically acceptable salt thereof, and (b) vitamin D3, or a pharmaceutically acceptable salt thereof.

The present disclosure also provides methods of treating a skin disease in a patient in need thereof, comprising topically administering to an affected area of the patient (a) a JAK inhibitor, or a pharmaceutically acceptable salt thereof, and (b) a vitamin D3 analog, or a pharmaceutically acceptable salt thereof.

The present disclosure also provides methods of treating a skin disease in a patient in need thereof, comprising topically administering to an affected area of the patient (a) ruxolitinib, or a pharmaceutically acceptable salt thereof, and (b) vitamin D3, a vitamin D3 analog, or a pharmaceutically acceptable salt thereof.

The present disclosure also provides methods of treating a skin disease in a patient in need thereof, comprising topically administering to an affected area of the patient (a) ruxolitinib, or a pharmaceutically acceptable salt thereof, and (b) vitamin D3, or a pharmaceutically acceptable salt thereof.

The present disclosure also provides methods of treating a skin disease in a patient in need thereof, comprising topically administering to an affected area of the patient (a) ruxolitinib, or a pharmaceutically acceptable salt thereof, and (b) a vitamin D3 analog, or a pharmaceutically acceptable salt thereof.

The present disclosure also provides methods of treating a skin disease in a patient in need thereof, comprising topically administering to an affected area of the patient (a) ruxolitinib phosphate, and (b) vitamin D3, a vitamin D3 analog, or a pharmaceutically acceptable salt thereof.

The present disclosure also provides methods of treating a skin disease in a patient in need thereof, comprising topically administering to an affected area of the patient (a) ruxolitinib phosphate, and (b) vitamin D3, or a pharmaceutically acceptable salt thereof.

The present disclosure also provides methods of treating a skin disease in a patient in need thereof, comprising topically administering to an affected area of the patient (a) ruxolitinib phosphate, and (b) a vitamin D3 analog, or a pharmaceutically acceptable salt thereof.

The present disclosure also provides methods of treating a skin disease in a patient in need thereof, comprising topically administering to an affected area of the patient (a) ruxolitinib phosphate, and (b) calcipotriol, or a pharmaceutically acceptable salt thereof. In some embodiments, the skin disease is an autoimmune skin disease.

The present disclosure also provides methods of treating a skin disease in a patient in need thereof, comprising topically administering to an affected area of the patient (a) a JAK inhibitor, or a pharmaceutically acceptable salt thereof, and (b) calcipotriol, or a pharmaceutically acceptable salt thereof. In some embodiments, the skin disease is an autoimmune skin disease.

In some embodiments, the skin disease is an inflammatory skin disease.

In some embodiments, the skin disease is associated with Th1 or Th2. T helper (Th)1 and/or T helper (Th)17 cells are involved in many inflammatory and autoimmune skin diseases. For example, the following diseases are primarily Th17 biased: (i) psoriasis (Fletcher, et al., *Clin Exp Immunol*, 201(2):121-134 (2020) at PMID: 32379344; Liu, et al., *Front Immunol*, 11:594735 (2020) at PMID: 33281823); (ii) ichthyosis (Czarnowicki, et al., *J Invest Dermatol*, 138(10): 2157-2167 (2018) at PMID: 29660300; Paller, et al, *J Allergy Clin Immunol*, 139(1):152-165 (2017) at PMID: 27554821); and (iii) pityriasis rubra pilaris (Liu, supra, at PMID: 33281823). Further, the following diseases are primarily Th1 biased: (i) alopecia areata (Żeberkiewicz, et al., *Cent Eur J Immunol*, 45(3):325-333 (2020) at PMID: 33437185; and (ii) vitiligo (Boniface, et al., *Clin Rev Allergy Immunol*, 54(1):52-67 (2018) at PMID: 28685247). Some diseases are associated with both Th1 and Th17, including: (i) hidradenitis suppurativa (Fletcher, supra, at PMID: 32379344; Liu, supra, at PMID: 33281823; Banerjee, et al., *Immunol Invest*, 46(2):149-158 (2017) at PMID: 27819528; Moran, et al., *J Invest Dermatol*, 137(11):2389-2395 (2017) at PMID: 28652108); and (ii) cutaneous lichen planus (Aghamajidi, et al., *Scand J Immunol*, e13000 (2020) at PMID: 33190330). Further, blocking of inflammatory cytokines, such as IL-22 and CXCL10 which are involved in Th1 or Th17 lymphocyte proliferation, survival and function, can be useful for treating Th1 or Th17 associated diseases. For example, T helper (Th)17 cells are a distinct lineage of effector CD4+ T cells characterized by their production of IL-17. See Liang, et al., *J Exp Med*, 203(10):2271-9 (2006) at PMID: 16982811. Th17 cells have been shown to express IL-22 at substantially higher amounts than Th1 or Th2 cells. Further, expansion of IL-22-producing cells is dependent on IL-23. In turn, blocking IL-17 and IL-23 are clinically validated approaches in psoriasis. Examples of this approach in treating psoriasis, a Th17 associated disease, include secukinumab and guselkumab, which block blocking IL-17 and IL-23, respectively. T helper (Th)1 cells are a distinct lineage of effector CD4+ T cells characterized by their production of IFN-gamma and T-bet transcriptional marker. See Szabo, et al., *Cell*, 100(6):655-69 (2000) at PMID: 10761931. CXCL10, also known as interferon gamma-induced protein 10 (IP-10), attracts lymphocytes to the skin. Further, CXCR3 is the receptor for the CXCL10 ligand. In turn, diseases such as vitiligo appear to be Th1 associated, as lymphocyte infiltration into vitiliginous skin is thought to be driven by CXCR3-positive Th1 cells responding to the CXCL10 ligand.

In some embodiments, the skin disease is mediated by interleukin 22 (IL-22), C-X-C motif chemokine 10 (CXCL10), matrix metallopeptidase 12 (MMP12), or a combination thereof. In some embodiments, the skin disease is mediated by IL-22. In some embodiments, the skin disease is mediated by MMP12. In some embodiments, the skin disease is mediated by CXCL10.

In some embodiments, the skin disease is mediated by Defb4, S100a12, or Serpinb4. S100a12 is a significant marker for psoriasis disease activity (Wilsmann-Theis, D, et al., J Eur Acad Dermatol Venereol, 30(7):1165-70 (2016); doi: 10.1111/jdv.13269, which is incorporated herein by reference in its entirety). Defb4 encodes human beta-defensin 2(hBD2), an antimicrobial peptide that plays an essentially role in inflammatory processes in the skin and is important in the pathogenesis of psoriasis (Johansen C, et al., J Invest Derm, 136(8):1608-1616 (2016); doi: 10.1016/j.jid.2016.04.012, which is incorporated herein by reference in its entirety). Serpinb4 contributes to inflammation in patients with chronic skin diseases, including atopic dermatitis (Sivaprasad, U, et al., J Invest Derm 135(1):160-169 (2015); DOI:10.1038/jid.2014.353, which is incorporated herein by reference in its entirety).

In some embodiments, the skin disease is selected from psoriasis, atopic dermatitis, alopecia, vitiligo, Reiter's syndrome, pityriasis rubra pilaris, epidermolysis bullosa simplex, palmoplantar keratoderma, pachyonychia congenita, steatocystoma multiplex, cutaneous lichen planus, cutaneous T-cell lymphoma, hidradenitis suppurativa, contact dermatitis, ichthyosis, and a disorder of keratinization.

In some embodiments, the skin disease is selected from psoriasis, atopic dermatitis, alopecia, vitiligo, Reiter's syndrome, pityriasis rubra pilaris, epidermolysis bullosa simplex, palmoplantar keratoderma, pachyonychia congenita, steatocystoma multiplex, cutaneous lichen planus, cutaneous T-cell lymphoma, hidradenitis suppurativa, contact dermatitis, and ichthyosis.

In some embodiments, the skin disease is psoriasis. In some embodiments, the psoriasis is mediated by interleukin 22 (IL-22), C-X-C motif chemokine 10 (CXCL10), matrix metallopeptidase 12 (MMP12), or a combination thereof. The nexus between psoriasis and IL-22, CXCL10, and/or MMP12 can be found, for example, at IL-22, CXCL10, and/or MMP12, see He et al. "Tape strips detect distinct immune and barrier profiles in atopic dermatitis and psoriasis" J Allergy Clin Immunol. 2020 Jul. 9; S0091-6749(20) 30824-1, PMID: 32709423, which is incorporated by reference in its entirety herein. In some embodiments, the psoriasis is mediated by interleukin 22 (IL-22). In some embodiments, the psoriasis is mediated by C-X-C motif chemokine 10 (CXCL10). In some embodiments, the psoriasis is mediated by matrix metallopeptidase 12 (MMP12). In some embodiments, the psoriasis is selected from plaque psoriasis, nail psoriasis, intertriginous psoriasis, palmoplantar psoriasis, and pustular psoriasis. In some embodiments, the psoriasis is plaque psoriasis. In some embodiments, the plaque psoriasis is mediated by interleukin 22 (IL-22). In some embodiments, the plaque psoriasis is mediated by C-X-C motif chemokine 10 (CXCL10). In some embodiments, the plaque psoriasis is mediated by matrix metallopeptidase 12 (MMP12).

In some embodiments, the skin disease is atopic dermatitis. In some embodiments, the atopic dermatitis is mediated by interleukin 22 (IL-22), C-X-C motif chemokine 10 (CXCL10), matrix metallopeptidase 12 (MMP12), or a combination thereof. The nexus between atopic dermatitis and IL-22 and/or MMP12 can be found, for example, at He et al. "Tape strips detect distinct immune and barrier profiles in atopic dermatitis and psoriasis" J Allergy Clin Immunol. 2020 Jul. 9; S0091-6749(20)30824-1, PMID: 32709423. The nexus between atopic dermatitis and CXCL10 can be found, for example, at Brunner et al. "Nonlesional atopic dermatitis skin shares similar T-cell clones with lesional tissues" Allergy. 2017 December; 72(12):2017-2025, PMID: 28599078. Each of the references cited herein is incorporated by reference in its entirety herein. In some embodiments, the atopic dermatitis is mediated by interleukin 22 (IL-22). In some embodiments, the atopic dermatitis is mediated by C-X-C motif chemokine 10 (CXCL10). In some embodiments, the atopic dermatitis is mediated by matrix metallopeptidase 12 (MMP12).

In some embodiments, the skin disease is alopecia. In some embodiments, the skin disease is alopecia areata. The nexus between alopecia areata and IL-22 can be found, for example, at Loh et al. "Role of T helper 17 cells and T regulatory cells in alopecia areata: comparison of lesion and serum cytokine between controls and patients" J Eur Acad Dermatol Venereol. 2018 June; 32(6):1028-1033, PMID: 29283462. The nexus between alopecia areata and CXCL10 can be found, for example, at Duca et al. "Frontal fibrosing alopecia shows robust T helper 1 and Janus kinase 3 skewing" Br J Dermatol. 2020 Mar. 25, PMID: 32215911. Each of the references cited herein is incorporated by reference in its entirety herein. In some embodiments, the alopecia is mediated by interleukin 22 (IL-22). In some embodiments, the alopecia is mediated by C-X-C motif chemokine 10 (CXCL10).

In some embodiments, the skin disease is vitiligo. The nexus between vitiligo and IL-22 can be found, for example, at Czarnowicki et al. "Blood endotyping distinguishes the profile of vitiligo from that of other inflammatory and autoimmune skin diseases" J Allergy Clin Immunol. 2019 June; 143(6):2095-2107. PMID: 30576756. The nexus between vitiligo and CXCL10 can be found, for example, at Abdallah et al. "CXCL-10 and Interleukin-6 are reliable serum markers for vitiligo activity: A multicenter cross-sectional study" Pigment Cell Melanoma Res. 2018 March; 31(2):330-336. PMID: 29094481. Each of the references cited herein is incorporated by reference in its entirety herein. In some embodiments, the vitiligo is mediated by interleukin 22 (IL-22). In some embodiments, the vitiligo is mediated by C-X-C motif chemokine 10 (CXCL10).

In some embodiments, the skin disease is Reiter's syndrome. The nexus between Reiter's syndrome and IL-22 can be found, for example, at Zhao et al. "IL-22+ CD4+ T cells in patients with rheumatoid arthritis" Int J Rheum Dis. 2013 October; 16(5):518-26, PMID: 24164838. The nexus between Reiter's syndrome and CXCL10 can be found, for example, at Pandya et al. "Blood chemokine profile in untreated early rheumatoid arthritis: CXCL10 as a disease activity marker" Arthritis Res Ther. 2017 Feb. 2; 19(1):20, PMID: 28148302. Each of the references cited herein is incorporated by reference in its entirety herein. In some embodiments, the Reiter's syndrome is mediated by interleukin 22 (IL-22). In some embodiments, the Reiter's syndrome is mediated by C-X-C motif chemokine 10 (CXCL10).

In some embodiments, the skin disease is pityriasis rubra pilaris. The nexus between pityriasis rubra pilaris and IL-22 can be found, for example, at Feldmeyer et al. "Interleukin 23-Helper T Cell 17 Axis as a Treatment Target for Pityriasis Rubra Pilaris" JAMA Dermatol. 2017 Apr. 1; 153(4):304-308, PMID: 28122069. The nexus between pityriasis rubra pilaris and CXCL10 can be found, for example, at Adnot-Desanlis et al. "Effectiveness of infliximab in pityriasis rubra pilaris is associated with pro-inflammatory cytokine inhibition" Dermatology 2013; 226(1):41-6, PMID: 23548788. Each of the references cited herein is incorporated by reference in its entirety herein. In some embodiments, the pityriasis rubra pilaris is mediated by interleukin 22 (IL-22). In some embodiments, the pityriasis rubra pilaris is mediated by C-X-C motif chemokine 10 (CXCL10).

In some embodiments, the skin disease is epidermolysis bullosa simplex. The nexus between epidermolysis bullosa simplex and IL-22 and/or CXCL10 can be found, for example, at Castela et al. "Epidermolysis bullosa simplex generalized severe induces a T helper 17 response and is improved by apremilast treatment" Br J Dermatol. 2019 February; 180(2):357-364, PMID: 29932457, which is incorporated by reference in its entirety herein. In some embodiments, the epidermolysis bullosa simplex is mediated by interleukin 22 (IL-22). In some embodiments, the epidermolysis bullosa simplex is mediated by C-X-C motif chemokine 10 (CXCL10).

In some embodiments, the skin disease is palmoplantar keratoderma. The nexus between almoplantar keratoderma and IL-22 can be found, for example, at Druetz et al. "Association of Transient Palmoplantar Keratoderma With Clinical and Immunologic Characteristics of Bullous Pemphigoid" JAMA Dermatol. 2019 Feb. 1; 155(2):216-220, PMID: 30484821, which is incorporated by reference in its entirety herein. In some embodiments, the palmoplantar keratoderma is mediated by interleukin 22 (IL-22).

In some embodiments, the skin disease is pachyonychia congenita. The nexus between pachyonychia congenita and IL-22 can be found, for example, at Yang et al. "Keratin 17 in disease pathogenesis: from cancer to dermatoses" J Pathol. 2019 February; 247(2):158-165, PMID: 30306595, which is incorporated by reference in its entirety herein. In some embodiments, the pachyonychia congenita is mediated by interleukin 22 (IL-22).

In some embodiments, the skin disease is steatocystoma multiplex. The nexus between steatocystoma multiplex and IL-22 can be found, for example, at Yang et al. "Keratin 17 in disease pathogenesis: from cancer to dermatoses" J Pathol. 2019 February; 247(2):158-165, PMID: 30306595, which is incorporated by reference in its entirety herein. In some embodiments, the steatocystoma multiplex is mediated by interleukin 22 (IL-22).

In some embodiments, the skin disease is cutaneous lichen planus. The nexus between cutaneous lichen planus and IL-22 can be found, for example, at Chen et al. "Immunoexpression of interleukin-22 and interleukin-23 in oral and cutaneous lichen planus lesions: a preliminary study" Mediators Inflamm. 2013; 2013:801974, PMID: 24376306. The nexus between cutaneous lichen planus and CXCL10 can be found, for example, at Domingues et al. "The dysfunctional innate immune response triggered by Toll-like receptor activation is restored by TLR7/TLR8 and TLR9 ligands in cutaneous lichen planus" Br J Dermatol. 2015 January; 172(1):48-55, PMID: 24976336 and Wenzel et al. "CXCR3↔ligand-mediated skin inflammation in cutaneous lichenoid graft-versus-host disease" J Am Acad Dermatol. 2008 March; 58(3):437-42, PMID: 18280341, each of which is incorporated by reference in its entirety herein. In some embodiments, the cutaneous lichen planus is mediated by interleukin 22 (IL-22). In some embodiments, the cutaneous lichen planus is mediated by C-X-C motif chemokine 10 (CXCL10).

In some embodiments, the skin disease is cutaneous T-cell lymphoma. In some embodiments, the cutaneous T-cell lymphoma is mediated by interleukin 22 (IL-22), C-X-C motif chemokine 10 (CXCL10), matrix metallopeptidase 12 (MMP12), or a combination thereof. The nexus between cutaneous T-cell lymphoma and IL-22 and/or MMP12 can be found, for example, at Litvinov et al. "The Use of Transcriptional Profiling to Improve Personalized Diagnosis and Management of Cutaneous T-cell Lymphoma (CTCL)" Clin Cancer Res. 2015 Jun. 15; 21(12):2820-9, PMID: 25779945. The nexus between cutaneous T-cell lymphoma and CXCL10 can be found, for example, at Mehul et al. "Proteomic analysis of stratum corneum in Cutaneous T-Cell Lymphomas and psoriasis" Exp Dermatol. 2019 March; 28(3):317-321, PMID: 30637808. Each of the references cited herein is incorporated by reference in its entirety herein. In some embodiments, the cutaneous T-cell lymphoma is mediated by interleukin 22 (IL-22). In some embodiments, the cutaneous T-cell lymphoma is mediated by C-X-C motif chemokine 10 (CXCL10). In some embodiments, the cutaneous T-cell lymphoma is mediated by matrix metallopeptidase 12 (MMP12).

In some embodiments, the skin disease is hidradenitis suppurativa. The nexus between hidradenitis suppurativa and IL-22 can be found, for example, at Rumberger et al. "Transcriptomic analysis of hidradenitis suppurativa skin suggests roles for multiple inflammatory pathways in disease pathogenesis" Inflamm Res. 2020 October; 69(10):967-973, PMID: 32661800, which is incorporated by reference in its entirety herein. In some embodiments, the hidradenitis suppurativa is mediated by interleukin 22 (IL-22).

In some embodiments, the skin disease is contact dermatitis. In some embodiments, the contact dermatitis is mediated by interleukin 22 (IL-22), C-X-C motif chemokine 10 (CXCL10), matrix metallopeptidase 12 (MMP12), or a combination thereof. The nexus between contact dermatitis and IL-22 can be found, for example, at Robb et al. "Prostaglandin E 2 stimulates adaptive IL-22 production and promotes allergic contact dermatitis" J Allergy Clin Immunol. 2018 January; 141(1):152-162, PMID: 28583370. The nexus between contact dermatitis and CXCL10 can be found, for example, at Brans et al. "Stratum corneum levels of inflammatory mediators and natural moisturizing factor in patch test reactions to thiurams and fragrances and their possible role in discrimination between irritant and allergic reactions to hapten mixtures" Contact Dermatitis. 2020 Nov. 21, PMID: 33222241. The nexus between contact dermatitis and MMP12 can be found, for example, at Meguro et al. "SOCS3 Expressed in M2 Macrophages Attenuates Contact Hypersensitivity by Suppressing MMP-12 Production" J Invest Dermatol. 2016 March; 136(3):649-657, PMID: 27015453. Each of the references cited herein is incorporated by reference in its entirety herein. In some embodiments, the contact dermatitis is mediated by interleukin 22 (IL-22). In some embodiments, the contact dermatitis is mediated by C-X-C motif chemokine 10 (CXCL10). In some embodiments, the contact dermatitis is mediated by matrix metallopeptidase 12 (MMP12).

In some embodiments, the skin disease is ichthyosis. The nexus between ichthyosis and IL-22 can be found, for example, at Czarnowicki et al. "The Major Orphan Forms of Ichthyosis Are Characterized by Systemic T-Cell Activation and Th-17/Tc-17/Th-22/Tc-22 Polarization in Blood" J Invest Dermatol. 2018 October; 138(10):2157-2167, PMID: 29660300, which is incorporated by reference in its entirety herein. In some embodiments, the ichthyosis is mediated by interleukin 22 (IL-22). In some embodiments, the ichthyosis is ichthyosis vulgaris, x-linked ichthyosis, bullous congenital ichthyosiform erythroderma (BCIE), nonbullous congenital ichthyosiform erythroderma (NBCIE), lamellar ichthyosis, harlequin ichthyosis, ichthyosis syndrome, or acquired ichthyosis.

Generally, disorders of keratinization are a group of disorders of cornification. The nexus between a disorder of keratinization and IL-22 can be found, for example, at Yang et al. "Keratin 17 in disease pathogenesis: from cancer to dermatoses" J Pathol. 2019 February; 247(2):158-165, PMID: 30306595, which is incorporated by reference in its entirety herein. In some embodiments, the disorder of keratinization is mediated by IL-22. In some embodiments, the disorder of keratinization is selected from ichthyosis, palmoplantar keratoderma, keratosis pilari, and acantholytic dermatosis.

In some embodiments, the skin disease is rosacea, psoriatic arthritis, dermal fibrosis, morphea, spitz nevi, dermatophytosis, or acne vulgaris. In some embodiments, the skin disease is rosacea. In some embodiments, the rosacea is mediated by interleukin 22 (IL-22) or C-X-C motif chemokine 10 (CXCL10), or a combination thereof. The nexus between rosacea and IL-22 and CXCL10 can be found, for example, see Buhl, et al., J. Invest. Derm., 135(9), P2198-2208 (2015), PMID: 25848978, which is incorporated by reference in its entirety herein. In some embodiments, the rosacea is mediated by interleukin 22 (IL-22). In some embodiments, the psoriasis is rosacea by C-X-C motif chemokine 10 (CXCL10). In some embodiments, the skin disease is psoriasis mediated by S100a12. In some embodiments, the skin disease is psoriatic arthritis mediated by S100a12. In some embodiments, the skin disease is dermal fibrosis mediated by S100a12. In some embodiments, the skin disease is morphea mediated by S100a12. In some embodiments, the skin disease is atopic dermatitis mediated by S100a12. In some embodiments, the skin disease is spitz nevi mediated by S100a12.

In some embodiments, the skin disease is psoriasis mediated by Defb4. In some embodiments, the skin disease is psoriatic arthritis mediated by Defb4. In some embodiments, the skin disease is dermatophytosis mediated by Defb4. In some embodiments, the skin disease is acne vulgaris mediated by Defb4. In some embodiments, the skin disease is hidradenitis suppurativa mediated by Defb4.

In some embodiments, the skin disease is psoriasis mediated by Serpinb4. In some embodiments, the skin disease is psoriatic arthritis mediated by Serpinb4.

In some embodiments, (a) the JAK inhibitor, or the pharmaceutically acceptable salt thereof, and (b) the vitamin D3, the vitamin D3 analog, or the pharmaceutically acceptable salt thereof, are administered sequentially.

In some embodiments, (a) the JAK inhibitor, or the pharmaceutically acceptable salt thereof, and (b) the vitamin D3, the vitamin D3 analog, or the pharmaceutically acceptable salt thereof, are administered sequentially.

In some embodiments, (a) the JAK inhibitor, or the pharmaceutically acceptable salt thereof, and (b) the vitamin D3, the vitamin D3 analog, or the pharmaceutically acceptable salt thereof, are administered at least one time per day.

In some embodiments, the JAK inhibitor, or the pharmaceutically acceptable salt thereof, is administered once per day.

In some embodiments, the JAK inhibitor, or the pharmaceutically acceptable salt thereof, is administered twice per day.

In some embodiments, the vitamin D3, the vitamin D3 analog, or the pharmaceutically acceptable salt thereof, is administered once per day.

In some embodiments, the vitamin D3, the vitamin D3 analog, or the pharmaceutically acceptable salt thereof, is administered twice per day.

In some embodiments, (a) the JAK inhibitor, or the pharmaceutically acceptable salt thereof, and (b) the vitamin D3, the vitamin D3 analog, or the pharmaceutically acceptable salt thereof, are administered as separate formulations.

In some embodiments, (a) the JAK inhibitor, or the pharmaceutically acceptable salt thereof, and (b) the vitamin D3, the vitamin D3 analog, or the pharmaceutically acceptable salt thereof, are administered as a single formulation.

In some embodiments, (a) the JAK inhibitor, or the pharmaceutically acceptable salt thereof, and (b) the vitamin D3, the vitamin D3 analog, or the pharmaceutically acceptable salt thereof, are administered once per day.

In some embodiments, (a) the JAK inhibitor, or the pharmaceutically acceptable salt thereof, and (b) the vitamin D3, the vitamin D3 analog, or the pharmaceutically acceptable salt thereof, are administered twice per day.

In some embodiments, the vitamin D3, the vitamin D3 analog, or the pharmaceutically acceptable salt thereof, is administered in a synergistic amount.

In some embodiments, there is a synergistic effect between the JAK inhibitor, or the pharmaceutically acceptable salt thereof, and the vitamin D3, the vitamin D3 analog, or the pharmaceutically acceptable salt thereof.

The present disclosure provides methods of treating a skin disease in a patient in need thereof, comprising topically administering to an affected area of the patient (a) a JAK inhibitor, or a pharmaceutically acceptable salt thereof, and (b) vitamin D3, a vitamin D3 analog, or a pharmaceutically acceptable salt thereof, further comprising administering an additional therapeutic agent. In some embodiments, the additional therapeutic agent is a corticosteroid.

In some embodiments, (b) is vitamin D3, or a pharmaceutically acceptable salt thereof.

In some embodiments, provided are the methods as described herein, wherein (a) the JAK inhibitor, or the pharmaceutically acceptable salt thereof, is administered in a therapeutically effective amount.

In some embodiments, provided are the methods as described herein, wherein (b) vitamin D3, the vitamin D3 analog, or the pharmaceutically acceptable salt thereof, is administered in a therapeutically effective amount.

In some embodiments of each of the aforementioned, the patient is a human patient.

In some embodiments, (a) the JAK inhibitor, or the pharmaceutically acceptable salt thereof, and (b) the vitamin D3 analog, or a pharmaceutically acceptable salt thereof, are administered one time per day.

In some embodiments, (a) the JAK inhibitor, or the pharmaceutically acceptable salt thereof, and (b) the vitamin D3 analog, or a pharmaceutically acceptable salt thereof, are administered at least two times per day.

In some embodiments, (a) the JAK inhibitor, or the pharmaceutically acceptable salt thereof, and (b) the vitamin D3 analog, or a pharmaceutically acceptable salt thereof, are administered at least two times per day.

In some embodiments, the JAK inhibitor, or a pharmaceutically acceptable salt thereof, and the vitamin D3 analog, or the pharmaceutically acceptable salt thereof, are each administered in a topical formulation. In some embodiments, each topical formulation is an ointment, a cream, or a lotion. In some embodiments, the JAK inhibitor, or a pharmaceutically acceptable salt thereof, and the vitamin D3 analog, or the pharmaceutically acceptable salt thereof, are in a single formulation. In some embodiments, the single formulation is a cream or a lotion. In some embodiments, the formulation has a pH of from about 6.0 to about 8.0, from about 6.5 to about 7.5, or from about 6.5 to about 7.0.

Vitamin D3 and Vitamin D3 Analogs for Use in Methods and Topical Formulations

In some embodiments, the vitamin D3, the vitamin D3 analog, or the pharmaceutically acceptable salt thereof, is a compound having Formula (I):

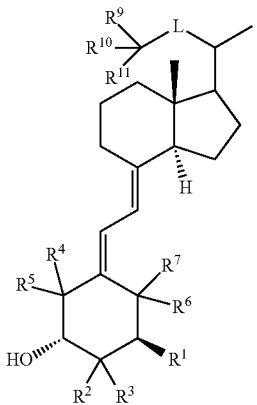

(I)

In some embodiments, $R^1$ is H or OH. In some embodiments, $R^1$ is H. In some embodiments, $R^1$ is OH.

In some embodiments, $R^2$ and $R^3$ are each H. In some embodiments, $R^2$ is H. In some embodiments, $R^3$ is H. In some embodiments, $R^2$ and $R^3$ are both H.

In some embodiments, $R^2$ is O—$R^{2A}$ and $R^3$ is H.

In some embodiments, $R^2$ and $R^3$ are taken together to form a =$CH_2$ group.

In some embodiments, $R^{2A}$ is —$C_{1-4}$ alkylene-OH.

In some embodiments, $R^4$ and $R^5$ are each H. In some embodiments, $R^4$ is H. In some embodiments, $R^5$ is H. In some embodiments, $R^4$ and $R^5$ are both H.

In some embodiments, $R^4$ and $R^5$ are taken together to form a =$CH_2$ group.

In some embodiments, $R^6$ and $R^7$ are each H. In some embodiments, $R^6$ and $R^7$ are both H. In some embodiments, $R^6$ is H. In some embodiments, $R^7$ is H.

In some embodiments, $R^6$ and $R^7$ are taken together to form a =$CH_2$ group.

In some embodiments, L is —$CH_2$—$CH_2$—$CH(R^{12})$—, —$CH_2$—$CH_2$—$CH_2$—$CH(R^{12})$—, —CH=CH—CH($R^{12}$)—, —CH=CH—CH=CH—, —$CH_2$—C≡C—, —O—$CH_2$—$CH_2$—, or —O—$CH_2$—$CH_2$—$CH_2$—. In some embodiments, L is —$CH_2$—$CH_2$—$CH(R^{12})$—. In some embodiments, L is —$CH_2$—$CH_2$—$CH_2$—$CH(R^{12})$—. In some embodiments, L is —CH=CH—CH($R^{12}$)—. In some embodiments, L is —CH=CH—CH=CH—. In some embodiments, L is —$CH_2$—C≡C—. In some embodiments, L is —O—$CH_2$—$CH_2$—. In some embodiments, L is —O—$CH_2$—$CH_2$—$CH_2$—. In some embodiments, $R^{12}$ is H or OH. In some embodiments, $R^{12}$ is OH. In some embodiments, $R^{12}$ is H.

In some embodiments, $R^9$ is $C_{1-3}$ alkyl or $C_{1-4}$ haloalkyl. In some embodiments, $R^9$ is $C_{1-3}$ alkyl. In some embodiments, $R^9$ is $C_{1-4}$ haloalkyl.

In some embodiments, $R^{10}$ is $C_{1-3}$ alkyl or $C_{1-4}$ haloalkyl. In some embodiments, $R^{10}$ is $C_{1-3}$ alkyl. In some embodiments, $R^{10}$ is $C_{1-4}$ haloalkyl.

In some embodiments, $R^{11}$ is H or OH. In some embodiments, $R^{11}$ is OH. In some embodiments, $R^{11}$ is H.

In some embodiments, $R^9$ and $R^{10}$ together with the carbon atom to which they are attached form a $C_{3-4}$ cycloalkyl ring. In some embodiments, $R^{11}$ is H.

In some embodiments, the vitamin D3, the vitamin D3 analog, or the pharmaceutically acceptable salt thereof, is a compound having Formula (II):

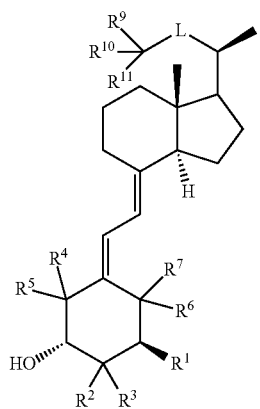

(II)

In some embodiments, $R^1$ is H or OH. In some embodiments, $R^1$ is H. In some embodiments, $R^1$ is OH.

In some embodiments, $R^2$ and $R^3$ are each H. In some embodiments, $R^2$ is H. In some embodiments, $R^3$ is H. In some embodiments, $R^2$ and $R^3$ are both H.

In some embodiments, $R^2$ is O—$R^{2A}$ and $R^3$ is H.

In some embodiments, $R^2$ and $R^3$ are taken together to form a =$CH_2$ group.

In some embodiments, $R^{2A}$ is —$C_{1-4}$ alkylene-OH.

In some embodiments, $R^4$ and $R^5$ are each H. In some embodiments, $R^4$ is H. In some embodiments, $R^5$ is H. In some embodiments, $R^4$ and $R^5$ are both H.

In some embodiments, $R^4$ and $R^5$ are taken together to form a =$CH_2$ group.

In some embodiments, $R^6$ and $R^7$ are each H. In some embodiments, $R^6$ and $R^7$ are both H. In some embodiments, $R^6$ is H. In some embodiments, $R^7$ is H.

In some embodiments, $R^6$ and $R^7$ are taken together to form a =$CH_2$ group.

In some embodiments, L is —$CH_2$—$CH_2$—$CH(R^{12})$—, —$CH_2$—$CH_2$—$CH_2$—$CH(R^{12})$—, —$CH$=$CH$—$CH(R^{12})$—, —$CH$=$CH$—$CH$=$CH$—, —$CH_2$—$C$≡$C$—, —O—$CH_2$—$CH_2$—, or —O—$CH_2$—$CH_2$—$CH_2$—. In some embodiments, L is —$CH_2$—$CH_2$—$CH(R^{12})$—. In some embodiments, L is —$CH_2$—$CH_2$—$CH_2$—$CH(R^{12})$—. In some embodiments, L is —CH=CH—$CH(R^{12})$—. In some embodiments, L is —CH=CH—CH=CH—. In some embodiments, L is —$CH_2$—C≡C—. In some embodiments, L is —O—$CH_2$—$CH_2$—. In some embodiments, L is —O—$CH_2$—$CH_2$—$CH_2$—. In some embodiments, $R^{12}$ is H or OH. In some embodiments, $R^{12}$ is OH. In some embodiments, $R^{12}$ is H.

In some embodiments, $R^9$ is $C_{1-3}$ alkyl or $C_{1-4}$ haloalkyl. In some embodiments, $R^9$ is $C_{1-3}$ alkyl. In some embodiments, $R^9$ is $C_{1-4}$ haloalkyl.

In some embodiments, $R^{10}$ is $C_{1-3}$ alkyl or $C_{1-4}$ haloalkyl. In some embodiments, $R^{10}$ is $C_{1-3}$ alkyl. In some embodiments, $R^{10}$ is $C_{1-4}$ haloalkyl.

In some embodiments, $R^{11}$ is H or OH. In some embodiments, $R^{11}$ is OH. In some embodiments, $R^{11}$ is H.

In some embodiments, $R^9$ and $R^{10}$ together with the carbon atom to which they are attached form a $C_{3-4}$ cycloalkyl ring. In some embodiments, $R^{11}$ is H.

In some embodiments, (b) is a vitamin D3 analog, or a pharmaceutically acceptable salt thereof.

In some embodiments, the vitamin D3, the vitamin D3 analog, or the pharmaceutically acceptable salt thereof, is a vitamin 1α-(OH) D3 analog, or a pharmaceutically acceptable salt thereof.

In some embodiments, the vitamin D3, the vitamin D3 analog, or the pharmaceutically acceptable salt thereof, is a vitamin 1α,25(OH)$_2$ D3 analog, a vitamin 1α,24(OH)$_2$ D3 analog or a vitamin 1α,26(OH)$_2$ D3 analog, or a pharmaceutically acceptable salt thereof.

In some embodiments, the vitamin D3, the vitamin D3 analog, or the pharmaceutically acceptable salt thereof, is a vitamin 1α,25(OH)$_2$ D3 analog, or a pharmaceutically acceptable salt thereof.

In some embodiments, the vitamin D3, the vitamin D3 analog, or the pharmaceutically acceptable salt thereof, is a vitamin 1α,24(OH)$_2$ D3 analog, or a pharmaceutically acceptable salt thereof.

In some embodiments, the vitamin D3, the vitamin D3 analog, or the pharmaceutically acceptable salt thereof, is a vitamin 1α,26(OH)$_2$ D3 analog, or a pharmaceutically acceptable salt thereof.

As used herein, "vitamin D3" (calcitol; cholecalciferol) has a formula of Formula (i) with numbering as shown below. As used herein, "vitamin D derivatives" refers to vitamin D3 (cholecalciferol), vitamin D2 (ergocalciferol), and structural analogs of Formula (i), sharing the scaffold the scaffold formed by carbons 1, 2, 3, 4, 5, 6, 7, 8, 9, 10, 11, 12, 13, 14, 15, 16, 17, 18, 20, and 21, wherein the stereochemistry at carbon 20 can be (R) or (S).

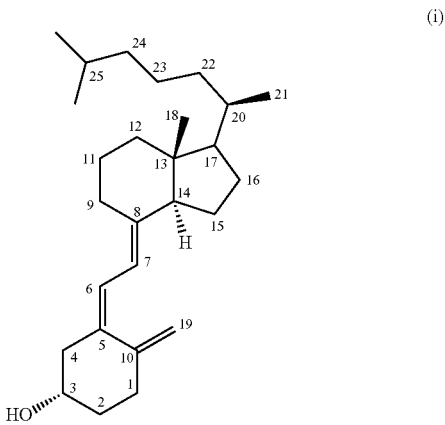 [SMILES: C=C1CC[C@H](O)C/C1=C/C=C1\CCC[C@]2(C)C([C@H](C)CCCC(C)C)CC[C@@H]12]

(i)

In some embodiments, the phrase "vitamin D3 analog" refers a structural analog of Formula (i), sharing the scaffold formed by carbons 1, 2, 3, 4, 5, 6, 7, 8, 9, 10, 11, 12, 13, 14, 15, 16, 17, 18, 20, and 21, wherein the stereochemistry at carbon 20 can be (R) or (S), wherein the compound does not contain a methyl substituent at carbon 24, and wherein the substitution and bonding at carbons 3, 6, 7, 8, 9, 11, 12, 13, 14, 15, 16, 17, 20, and 21 remains unaltered. In some embodiments, the double bond at carbon 19 is absent. In some embodiments, the double bond at carbon 19 is present. In some embodiments, carbon 1 may have a hydroxy group α to the hydroxy group at carbon 3.

As used herein, the phrase "vitamin 1α-(OH) D3 analog" refers a structural analog of Formula (ii), sharing scaffold formed by carbons 1, 2, 3, 4, 5, 6, 7, 8, 9, 10, 11, 12, 13, 14, 15, 16, 17, 18, 20, and 21, wherein each dotted line can be a single, double or triple bond within the constraints of proper valency, wherein the compound does not contain a methyl substituent at carbon 24 and wherein the substitution at carbons 3, 6, 7, 8, 9, 11, 12, 13, 14, 15, 16, 17, 20, and 21 remains unaltered. In some embodiments, the double bond at carbon 19 is absent. In some embodiments, the double bond at carbon 19 is present.

(ii)

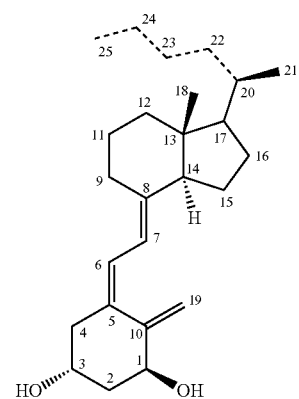

As used herein, the phrase "vitamin 1α,25-(OH)$_2$ D3 analog" refers a structural analog of Formula (iii), sharing scaffold formed by carbons 1, 2, 3, 4, 5, 6, 7, 8, 9, 10, 11, 12, 13, 14, 15, 16, 17, 18, 20, 21, 22, 23, 24, and 25, wherein each dotted line can be a single, double or triple bond within the constraints of proper valency, wherein the compound does not contain a methyl substituent at carbon 24, and wherein the substitution at carbons 3, 6, 7, 8, 9, 11, 12, 13, 14, 15, 16, 17, 20, and 21 remains unaltered. In some embodiments, the double bond at carbon 19 is absent. In some embodiments, the double bond at carbon 19 is present.

Formula (iii)

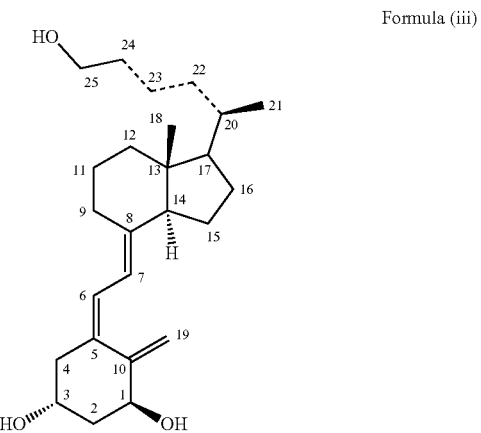

As used herein, the phrase "vitamin 1α,24-(OH)$_2$ D3 analog" refers a structural analog of structure (iv), sharing scaffold formed by carbons 1, 2, 3, 4, 5, 6, 7, 8, 9, 10, 11, 12, 13, 14, 15, 16, 17, 18, 20, 21, 22, 23, and 24, wherein each dotted line can be a single, double or triple bond within the constraints of proper valency, wherein the compound does not contain a methyl substituent at carbon 24, and wherein the substitution at carbons 3, 6, 7, 8, 9, 11, 12, 13, 14, 15, 16, 17, 20, and 21 remains unaltered. In some embodiments, the double bond at carbon 19 is absent. In some embodiments, the double bond at carbon 19 is present.

(iv)

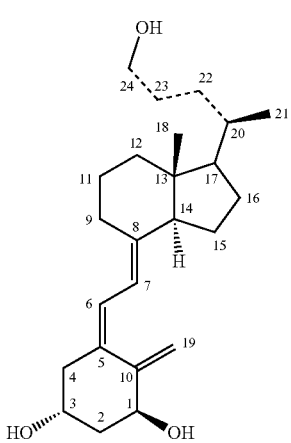

As used herein, the phrase "vitamin 1α,26-(OH)$_2$ D3 analog" refers a structural analog of structure (v), sharing scaffold formed by carbons 1, 2, 3, 4, 5, 6, 7, 8, 9, 10, 11, 12, 13, 14, 15, 16, 17, 18, 20, 21, 22, 23, 24, 25, and 26 wherein each dotted line can be a single, double or triple bond within the constraints of proper valency, wherein the compound does not contain a methyl substituent at carbon 24, and wherein the substitution at carbons 3, 6, 7, 8, 9, 11, 12, 13, 14, 15, 16, 17, 20, and 21 remains unaltered. In some embodiments, the double bond at carbon 19 is absent. In some embodiments, the double bond at carbon 19 is present.

Formula (v)

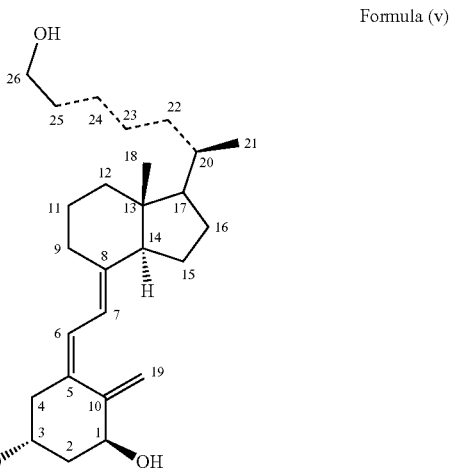

In some embodiments, the vitamin D3, the vitamin D3 analog, or the pharmaceutically acceptable salt thereof, is a compound having Formula (III):

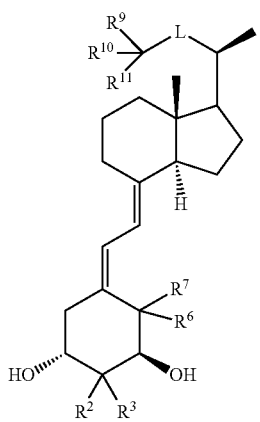

(III)

In some embodiments, $R^2$ and $R^3$ are each H. In some embodiments, $R^2$ is H. In some embodiments, $R^3$ is H. In some embodiments, $R^2$ and $R^3$ are both H.

In some embodiments, $R^2$ is O—$R^{2A}$ and $R^3$ is H.

In some embodiments, $R^{2A}$ is —$C_{1-4}$ alkylene-OH.

In some embodiments, $R^6$ and $R^7$ are each H. In some embodiments, $R^6$ and $R^7$ are both H. In some embodiments, $R^6$ is H. In some embodiments, $R^7$ is H.

In some embodiments, $R^6$ and $R^7$ are taken together to form a =$CH_2$ group.

In some embodiments, L is —$CH_2$—$CH_2$—$CH(R^{12})$—, —CH=CH—$CH(R^{12})$—, —CH=CH—CH=CH—, —$CH_2$—C≡C—, —O—$CH_2$—$CH_2$—, or —O—$CH_2$—$CH_2$—$CH_2$—. In some embodiments, L is —$CH_2$—$CH_2$—$CH(R^{12})$—. In some embodiments, L is —CH=CH—CH($R^{12}$)—. In some embodiments, L is —CH=CH—CH=CH—. In some embodiments, L is —$CH_2$—C≡C—. In some embodiments, L is —O—$CH_2$—$CH_2$—. In some embodiments, L is —O—$CH_2$—$CH_2$—$CH_2$—. In some embodiments, $R^{12}$ is H or OH. In some embodiments, $R^{12}$ is OH. In some embodiments, $R^{12}$ is H.

In some embodiments, $R^9$ is $CH_3$ or $CF_3$. In some embodiments, $R^9$ is $CH_3$. In some embodiments, $R^9$ is $CF_3$.

In some embodiments, $R^{10}$ is $CH_3$ or $CF_3$. In some embodiments, $R^{10}$ is $CF_3$. In some embodiments, $R^{10}$ is $CH_3$.

In some embodiments, $R^{11}$ is H or OH. In some embodiments, $R^{11}$ is H. In some embodiments, $R^{11}$ is OH.

In some embodiments, $R^9$ and $R^{10}$ together with the carbon atom to which they are attached form a cyclopropyl ring. In some embodiments, $R^{11}$ is H.

In some embodiments, the vitamin D3, the vitamin D3 analog, or the pharmaceutically acceptable salt thereof, is selected from calcidiol, calcitriol, calcipotriol, alfacalcidol, tacalcitol, maxacalcitol, falecalcitriol, eldecalcitol, inecalcitol, seocalcitol, lexicalcitol, 20-epi-1α,25(OH)$_2$D$_3$, CD578 (17-methyl-19-nor-21-nor-23-yne-26,27-F6-1α,25(OH)$_2$ D$_3$), TX527 (19-nor-14,20-bisepi-23-yne-1α,25(OH)$_2$D$_3$), 2MD (2-methylene-19-nor-(20S)-1α,25(OH)$_2$D$_3$), PRI-2205 ((5E,7E)-22-ene-26,27-dehydro-1α,25(OH)$_2$D$_3$), IL-X23-7553 (16-ene-23-yne-1α,25(OH)$_2$D$_3$), and MART-10 (19-nor-2α-(3-hydroxypropyl)-1α,25(OH)$_2$D$_3$).

In some embodiments, the vitamin D3, the vitamin D3 analog, or the pharmaceutically acceptable salt thereof, is selected from calcidiol, calcitriol, calcipotriol, alfacalcidol, tacalcitol, maxacalcitol, falecalcitriol, eldecalcitol, inecalcitol, seocalcitol, and lexicalcitol.

In some embodiments, the vitamin D3, the vitamin D3 analog, or the pharmaceutically acceptable salt thereof, is selected from calcipotriol, tacalcitol, maxacalcitol, and seocalcitol.

In some embodiments, the vitamin D3, the vitamin D3 analog, or the pharmaceutically acceptable salt thereof, is calcipotriol.

In some embodiments, the vitamin D3, the vitamin D3 analog, or the pharmaceutically acceptable salt thereof, is maxacalcitol.

In some embodiments, the vitamin D3, the vitamin D3 analog, or the pharmaceutically acceptable salt thereof, is tacalcitol.

In some embodiments, the vitamin D3, the vitamin D3 analog, or the pharmaceutically acceptable salt thereof, is seocalcitol.

In some embodiments, the vitamin D3, the vitamin D3 analog, or the pharmaceutically acceptable salt thereof, is calcidiol.

In some embodiments, the vitamin D3, the vitamin D3 analog, or the pharmaceutically acceptable salt thereof, is calcitriol.

In some embodiments, the vitamin D3, the vitamin D3 analog, or the pharmaceutically acceptable salt thereof, is alfacalcidol.

In some embodiments, the vitamin D3, the vitamin D3 analog, or the pharmaceutically acceptable salt thereof, is falecalcitriol.

In some embodiments, the vitamin D3, the vitamin D3 analog, or the pharmaceutically acceptable salt thereof, is eldecalcitol.

In some embodiments, the vitamin D3, the vitamin D3 analog, or the pharmaceutically acceptable salt thereof, is inecalcitol, In some embodiments, the vitamin D3, the vitamin D3 analog, or the pharmaceutically acceptable salt thereof, is lexicalcitol.

Formulations of Vitamin D3 or Vitamin D3 Analogs for Use in Methods

In some embodiments, the vitamin D3, the vitamin D3 analog, or the pharmaceutically acceptable salt thereof, is administered in a topical formulation. In some embodiments, the topical formulation is a foam, an ointment, a lotion, or a cream.

In some embodiments, the vitamin D3, the vitamin D3 analog, or the pharmaceutically acceptable salt thereof, is administered as a topical formulation comprising from about 0.0001% to about 0.1% of the vitamin D3, the vitamin D3 analog, or the pharmaceutically acceptable salt thereof, on a free base basis by weight of the formulation. In some embodiments, the vitamin D3, the vitamin D3 analog, or the pharmaceutically acceptable salt thereof, is administered as a topical formulation comprising from about 0.0001% to about 0.02% of the vitamin D3, the vitamin D3 analog, or the pharmaceutically acceptable salt thereof, on a free base basis by weight of the formulation. In some embodiments, the vitamin D3, the vitamin D3 analog, or the pharmaceutically acceptable salt thereof, is administered as a topical formulation comprising from about 0.0001% to about 0.005% of the vitamin D3, the vitamin D3 analog, or the pharmaceutically acceptable salt thereof, on a free base basis by weight of the formulation. In some embodiments, the vitamin D3, the vitamin D3 analog, or the pharmaceutically acceptable salt thereof, is administered as a topical formulation comprising from about 0.0004% to about 0.005% of the vitamin D3, the vitamin D3 analog, or the pharmaceutically acceptable salt thereof, on a free base basis by weight of the formulation.

In some embodiments, the vitamin D3, the vitamin D3 analog, or the pharmaceutically acceptable salt thereof, is calcipotriol, which is administered as a topical formulation comprising about 50 µg calcipotriol per gram of the formulation.

In some embodiments, the topical formulation is a foam, an ointment, a lotion, or a cream. In some embodiments, the topical formulation further comprises betamethasone dipropionate. In some embodiments, the betamethasone dipropionate is present in an amount of about 0.5 mg per gram of the formulation.

In some embodiments, the vitamin D3 analog is tacalcitol, which is administered as a topical formulation comprising about 4 µg tacalcitol per gram of the formulation. In some embodiments, the topical formulation is an ointment, a cream, or a lotion.

In some embodiments, the vitamin D3 analog is maxacalcitol, which is administered as a topical formulation comprising about 6 µg, about 12.5 µg/g, about 25 µg, or about 50 µg per gram of the formulation. In some embodiments, the topical formulation is an ointment.

JAK Inhibitors for Use in Methods and Topical Formulations

In some embodiments, the JAK inhibitor, or the pharmaceutically acceptable salt thereof, is a compound that inhibits JAK1, JAK2, JAK3, and/or TYK2. In some embodiments, the JAK inhibitor, or the pharmaceutically acceptable salt thereof, is selected from a JAK1 inhibitor, a JAK2 inhibitor, a JAK3 inhibitor, a TYK2 inhibitor, a JAK1/JAK2 inhibitor, a pan-JAK inhibitor, a JAK1/TYK2 inhibitor, and a JAK1/JAK3 inhibitor, or a pharmaceutically acceptable salt of any of the aforementioned.

In some embodiments, the JAK inhibitor, or the pharmaceutically acceptable salt thereof, is selected from ruxolitinib, baricitinib, oclacitinib, momelotinib, CTP-543, AH057, gandotinib, fedratinib, lestaurtinib, pacritinib, CHZ868, upadacitinib, tofacitinib, filgocitinib, abrocitinib, itacitinib, brepocitinib, ATI-501, ATI-1777, ATI-502, delgocitinib, peficitinib, gusacitinib, cucurbitacin I, cerdulatinib, decernotinib, BMS-986165, and ritlecitinib, or a pharmaceutically acceptable salt thereof.

In some embodiments, the JAK inhibitor, or the pharmaceutically acceptable salt thereof, is a JAK1 inhibitor, or a pharmaceutically acceptable salt thereof.

In some embodiments, the JAK1 inhibitor is a selective JAK1 inhibitor, or a pharmaceutically acceptable salt thereof. JAK1 plays a central role in a number of cytokine and growth factor signaling pathways that, when dysregulated, can result in or contribute to disease states. For example, IL-6 levels are elevated in rheumatoid arthritis, a disease in which it has been suggested to have detrimental effects (see e.g., Fonesca, et al., *Autoimmunity Reviews*, 8:538-42, 2009). Because IL-6 signals, at least in part, through JAK1, IL-6 can be indirectly through JAK1 inhibition, resulting in potential clinical benefit (see e.g., Guschin, et al. Embo J 14:1421, 1995; and Smolen, et al. *Lancet* 371:987, 2008). In other autoimmune diseases and cancers, elevated systemic levels of inflammatory cytokines that activate JAK1 may also contribute to the disease and/or associated symptoms. Therefore, patients with such diseases may benefit from JAK1 inhibition. Selective inhibitors of JAK1 may be efficacious while avoiding unnecessary and potentially undesirable effects of inhibiting other JAK kinases, as described herein. In some embodiments, the JAK1 inhibitor is selective for JAK1 preferentially over JAK2 (e.g., having a JAK2/JAK1 $IC_{50}$ ratio >1). In some embodiments, the compounds or salts as provided and described herein are about 10-fold more selective for JAK1 over JAK2. In some embodiments, the compounds or salts provided herein are about 3-fold, about 5-fold, about 10-fold, about 15-fold, or about 20-fold more selective for JAK1 over JAK2 as calculated by measuring $IC_{50}$ at 1 mM ATP (see Example 1).

In some embodiments, the JAK inhibitor, or the pharmaceutically acceptable salt thereof, is a JAK2 inhibitor, or a pharmaceutically acceptable salt thereof.

In some embodiments, the JAK2 inhibitor is a selective JAK2 inhibitor, or a pharmaceutically acceptable salt thereof. In some embodiments, the JAK2 inhibitor is about 3-fold, about 5-fold, about 10-fold, about 15-fold, or about 20-fold more selective for JAK2 over JAK1, JAK3 and TYK2 as calculated by measuring $IC_{50}$ at 1 mM ATP.

In some embodiments, the JAK inhibitor, or the pharmaceutically acceptable salt thereof, is a JAK3 inhibitor, or a pharmaceutically acceptable salt thereof.

In some embodiments, the JAK3 inhibitor is a selective JAK3 inhibitor, or a pharmaceutically acceptable salt thereof. In some embodiments, the JAK3 inhibitor is about 3-fold, about 5-fold, about 10-fold, about 15-fold, or about 20-fold more selective for JAK2 over JAK1, JAK2 and TYK2 as calculated by measuring $IC_{50}$ at 1 mM ATP.

In some embodiments, the JAK inhibitor, or the pharmaceutically acceptable salt thereof, is a TYK2 inhibitor, or a pharmaceutically acceptable salt thereof.

In some embodiments, the TYK2 inhibitor is a selective TYK2 inhibitor, or a pharmaceutically acceptable salt thereof. In some embodiments, the TYK2 inhibitor is about 3-fold, about 5-fold, about 10-fold, about 15-fold, or about 20-fold more selective for TYK2 over JAK1, JAK2 and JAK3 as calculated by measuring $IC_{50}$ at 1 mM ATP.

In some embodiments, the JAK inhibitor, or the pharmaceutically acceptable salt thereof, is a JAK1/JAK2 inhibitor, or a pharmaceutically acceptable salt thereof.

In some embodiments, the JAK1/JAK2 inhibitor, or the pharmaceutically acceptable salt thereof, is selective for JAK1 and JAK2 over JAK3 and TYK2. In some embodiments, the JAK1/JAK2 inhibitor, or a pharmaceutically acceptable salt thereof, is selective for JAK1 and JAK2 over JAK3. In some embodiments, the compounds or salts are about 10-fold more selective for JAK1 and JAK2 over JAK3. In some embodiments, the compounds or salts are about 3-fold, about 5-fold, about 10-fold, about 15-fold, or about 20-fold more selective for JAK1 and JAK2 over JAK3 as calculated by measuring $IC_{50}$ at 1 mM ATP.

In some embodiments, the JAK inhibitor, or the pharmaceutically acceptable salt thereof, is a pan-JAK inhibitor, or a pharmaceutically acceptable salt thereof.

In some embodiments, the JAK inhibitor, or the pharmaceutically acceptable salt thereof, is a JAK1/TYK2 inhibitor, or a pharmaceutically acceptable salt thereof.

In some embodiments, the JAK1/TYK2 inhibitor is about 3-fold, about 5-fold, about 10-fold, about 15-fold, or about 20-fold more selective for JAK1 and TYK2 over JAK2 and JAK3 as calculated by measuring $IC_{50}$ at 1 mM ATP.

In some embodiments, the JAK inhibitor, or the pharmaceutically acceptable salt thereof, is a JAK1/JAK3 inhibitor, or a pharmaceutically acceptable salt thereof.

In some embodiments, the JAK1/JAK3 inhibitor is about 3-fold, about 5-fold, about 10-fold, about 15-fold, or about 20-fold more selective for JAK1 and JAK3 over JAK2 and TYK2 as calculated by measuring $IC_{50}$ at 1 mM ATP.

In some embodiments, the JAK inhibitor, or the pharmaceutically acceptable salt thereof, is ruxolitinib, or a pharmaceutically acceptable salt thereof. Ruxolitinib is a JAK1/JAK2 inhibitor. Ruxolitinib has an $IC_{50}$ of less than 10 nM at 1 mM ATP at JAK1 and JAK2. ruxolitinib can be made by the procedure described in U.S. Pat. No. 7,598,257 (Example 67), filed Dec. 12, 2006, which is incorporated herein by reference in its entirety.

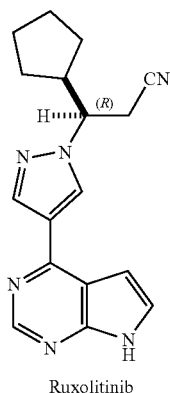

Ruxolitinib

In some embodiments, the JAK inhibitor, or the pharmaceutically acceptable salt thereof, is ruxolitinib phosphate. In some embodiments, the JAK inhibitor, or the pharmaceutically acceptable salt thereof, is the 1:1 ruxolitinib phosphoric acid salt. The phosphoric acid salt can be made as described in U.S. Pat. No. 8,722,693, which is incorporated herein by reference in its entirety.

In some embodiments, the ruxolitinib or the salt thereof is administered as a topical formulation. In some embodiments, the topical formulation comprises from about 0.05% to about 3.0%, about 0.05% to about 1.5%, about 0.05% to about 1%, about 0.05% to about 0.5%, about 0.1% to about 3.0%, about 0.1% to about 2.0%, from about 0.1% to about 1.5%, from about 0.1% to about 1.0%, from about 0.1% to about 0.5%, from about 0.5% to about 2.0%%, from about 0.5% to about 1.5%, or from about 0.5% to about 1.0% by weight of the formulation on a free base basis of the ruxolitinib, or the pharmaceutically acceptable salt thereof. In some embodiments, the topical formulation comprises from about 0.5% to about 1.5% by weight of the formulation on a free base basis of the ruxolitinib, or the pharmaceutically acceptable salt thereof. In some embodiments, the topical formulation comprises about 0.05%, about 0.06%, about 0.07%, about 0.08%, about 0.09%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1.0%, about 1.05%, about 1.1%, about 1.15%, about 1.2%, about 1.25%, about 1.3%, about 1.35%, about 1.4%, about 1.45%, about 1.5%, about 1.55%, about 1.6%, about 1.65%, about 1.7%, about 1.75%, about 1.8%, about 1.85%, about 1.9%, about 1.95%, about 2.0%, about 2.5%, or about 3.0% by weight of the formulation on a free base basis of the ruxolitinib, or the pharmaceutically acceptable salt thereof.

In some embodiments, the JAK inhibitor, or the pharmaceutically acceptable salt thereof, is ruxolitinib, wherein one or more hydrogen atoms are replaced by deuterium atoms, or a pharmaceutically acceptable salt thereof. In some embodiments, the JAK inhibitor, or the pharmaceutically acceptable salt thereof, is any of the compounds in U.S. Pat. No. 9,249,149, which is incorporated herein by reference in its entirety, or a pharmaceutically acceptable salt thereof. In some embodiments, the JAK inhibitor, or the pharmaceutically acceptable salt thereof, is CTP-543 (having the structure below), or a pharmaceutically acceptable salt thereof.

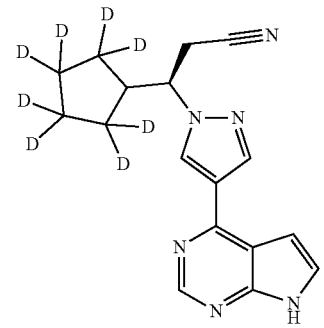 [SMILES: [2H]C1([2H])C([C@@H](CC#N)n2cc(-c3ncnc4[nH]ccc34)cn2)C([2H])([2H])C([2H])([2H])C1([2H])[2H]]

In some embodiments, the JAK inhibitor, or the pharmaceutically acceptable salt thereof, is a compound of Formula IV:

IV

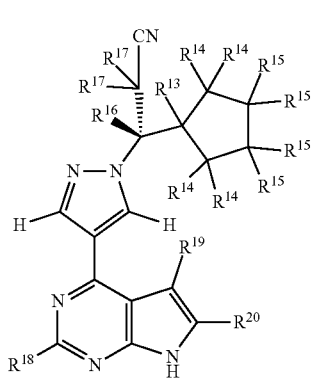

or a pharmaceutically acceptable salt thereof, wherein:
  $R^{13}$ is selected from H and D;
  each $R^{14}$ is independently selected from H and D, provided that each $R^{14}$ attached to a common carbon is the same;
  each $R^{15}$ is independently selected from H and D, provided that each $R^{15}$ attached to a common carbon is the same;
  $R^{16}$ is selected from H and D;
  each $R^{17}$ is the same and is selected from H and D; and
  $R^{18}$, $R^{19}$, and $R^{20}$ are each independently selected from H and D; provided that when $R^{13}$ is H, each $R^{14}$ and each $R^{15}$ are H, $R^{16}$ is H, and each of $R^{18}$, $R^{19}$, and $R^{20}$ is H, then each $R^{17}$ is D.

CTP-543 is a compound of Formula IV, which is a JAK1/JAK2 inhibitor.

In some embodiments, the JAK inhibitor, or the pharmaceutically acceptable salt thereof, is a compound of Formula IV selected from the following compounds 100-130 in the table below (wherein $R^{18}$, $R^{19}$, and $R^{20}$ are each H), or a pharmaceutically acceptable salt thereof. In some embodiments, the JAK inhibitor, or the pharmaceutically acceptable salt thereof, is a compound of Formula IV selected from the following compounds 200-231 in the table below (wherein $R^{18}$, $R^{19}$, and $R^{20}$ are each D), or a pharmaceutically acceptable salt thereof.

| Compound | R¹³ | Each R¹⁴ | Each R¹⁵ | R¹⁶ | Each R¹⁷ |
|---|---|---|---|---|---|
| 100 | H | H | H | D | H |
| 101 | H | H | H | H | D |
| 102 | H | H | H | D | D |
| 103 | H | H | D | H | H |
| 104 | H | H | D | D | H |
| 105 | H | H | D | H | D |
| 106 | H | H | D | D | D |
| 107 | H | D | H | H | H |
| 108 | H | D | H | D | H |
| 109 | H | D | H | H | D |
| 110 | H | D | H | D | D |
| 111 | H | D | D | H | H |
| 112 | H | D | D | D | H |
| 113 | H | D | D | H | D |
| 114 | H | D | D | D | D |
| 115 | D | H | H | H | H |
| 116 | D | H | H | D | H |
| 117 | D | H | H | H | D |
| 118 | D | H | H | D | D |
| 119 | D | H | D | H | H |
| 120 | D | H | D | D | H |
| 121 | D | H | D | H | D |
| 122 | D | H | D | D | D |
| 123 | D | D | H | H | H |
| 124 | D | D | H | D | H |
| 125 | D | D | H | H | D |
| 126 | D | D | H | D | D |
| 127 | D | D | D | H | H |
| 128 | D | D | D | D | H |
| 129 | D | D | D | H | D |
| 130 | D | D | D | D | D |
| 200 | H | H | H | H | H |
| 201 | H | H | H | H | D |
| 202 | H | H | H | D | D |
| 203 | H | H | D | H | H |
| 204 | H | H | D | D | H |
| 205 | H | H | D | H | D |
| 206 | H | H | D | D | D |
| 207 | H | D | H | H | H |
| 208 | H | D | H | D | H |
| 209 | H | D | H | H | D |
| 210 | H | D | H | D | D |
| 211 | H | D | D | H | H |
| 212 | H | D | D | D | H |
| 213 | H | D | D | H | D |
| 214 | H | D | D | D | D |
| 215 | D | H | H | H | H |
| 216 | D | H | H | D | H |
| 217 | D | H | H | H | D |
| 218 | D | H | H | D | D |
| 219 | D | H | D | H | H |
| 220 | D | H | D | D | H |
| 221 | D | H | D | H | D |
| 222 | D | H | D | D | D |
| 223 | D | D | H | H | H |
| 224 | D | D | H | D | H |
| 225 | D | D | H | H | D |
| 226 | D | D | H | D | D |
| 227 | D | D | D | H | H |
| 228 | D | D | D | D | H |
| 229 | D | D | D | H | D |
| 230 | D | D | D | D | D |
| 231 | H | H | H | H | H |

In some embodiments, the JAK inhibitor, or the pharmaceutically acceptable salt thereof, is baricitinib, or a pharmaceutically acceptable salt thereof. Baricitinib is a JAK1/JAK2 inhibitor.

In some embodiments, the JAK inhibitor, or the pharmaceutically acceptable salt thereof, is baricitinib, wherein one or more hydrogen atoms are replaced by deuterium atoms, or a pharmaceutically acceptable salt thereof. In some embodiments, the JAK inhibitor, or the pharmaceutically acceptable salt thereof, is any of the compounds in U.S. Pat. No. 9,540,367 (which is incorporated herein by reference in its entirety), or a pharmaceutically acceptable salt thereof.

In some embodiments, the JAK inhibitor, or the pharmaceutically acceptable salt thereof, is oclacitinib, or a pharmaceutically acceptable salt thereof. Oclacitinib is a JAK1/JAK2 inhibitor.

In some embodiments, the JAK inhibitor, or the pharmaceutically acceptable salt thereof, is momelotinib, or a pharmaceutically acceptable salt thereof. Momelotinib is a JAK1/JAK2 inhibitor.

In some embodiments, the JAK inhibitor, or the pharmaceutically acceptable salt thereof, is AH057, or a pharmaceutically acceptable salt thereof. AH057 is a JAK1/JAK2 inhibitor.

In some embodiments, the JAK inhibitor, or the pharmaceutically acceptable salt thereof, is gandotinib, or a pharmaceutically acceptable salt thereof. Gandotinib is a JAK2 inhibitor.

In some embodiments, the JAK inhibitor, or the pharmaceutically acceptable salt thereof, is fedratinib, or a pharmaceutically acceptable salt thereof. Fedratinib is a JAK2 inhibitor.

In some embodiments, the JAK inhibitor, or the pharmaceutically acceptable salt thereof, is lestaurtinib, or a pharmaceutically acceptable salt thereof. Lestaurtinib is a JAK2 inhibitor.

In some embodiments, the JAK inhibitor, or the pharmaceutically acceptable salt thereof, is pacritinib, or a pharmaceutically acceptable salt thereof. Pacritinib is a JAK2 inhibitor, which also inhibits fms-like tyrosine kinase 3 (FLT3).

In some embodiments, the JAK inhibitor, or the pharmaceutically acceptable salt thereof, is CHZ868, or a pharmaceutically acceptable salt thereof. CHZ868 is a JAK2 inhibitor.

In some embodiments, the JAK inhibitor, or the pharmaceutically acceptable salt thereof, is upadacitinib, or a pharmaceutically acceptable salt thereof. Upadacitinib is a JAK1 inhibitor.

In some embodiments, the JAK inhibitor, or the pharmaceutically acceptable salt thereof, is filgotinib, or a pharmaceutically acceptable salt thereof. Filgotinib is a JAK1 inhibitor.

In some embodiments, the JAK inhibitor, or the pharmaceutically acceptable salt thereof, is abrocitinib, or a pharmaceutically acceptable salt thereof. Abrocitinib is a JAK1 inhibitor.

In some embodiments, the JAK inhibitor, or the pharmaceutically acceptable salt thereof, is itacitinib, or a pharmaceutically acceptable salt thereof. Itacitinib is a JAK1 inhibitor.

In some embodiments, the JAK inhibitor, or the pharmaceutically acceptable salt thereof, is a JAK1 inhibitor, which is a compound of Table 1, or a pharmaceutically acceptable salt thereof. The compounds in Table 1 are JAK1 selective inhibitors (e.g., selective over JAK2, JAK3, and TYK2). The $IC_{50}$ values obtained by the method of Example 1 at 1 mM ATP are shown in Table 1.

TABLE 1

| Comp. No. | Prep. | Name | Structure | JAK1 IC$_{50}$ (nM) | JAK2/JAK1 |
|---|---|---|---|---|---|
| 1 | Itacitinib; US 2011/ 0224190 (Example 1) | {1-{1-[3-Fluoro-2-(trifluoromethyl) isonicotinoyl]piperidin-4-yl}-3-[4-(7H-pyrrolo [2,3-d]pyrimidin-4-yl)-1H-pyrazol-1-yl]azetidin-3-yl}acetonitrile | 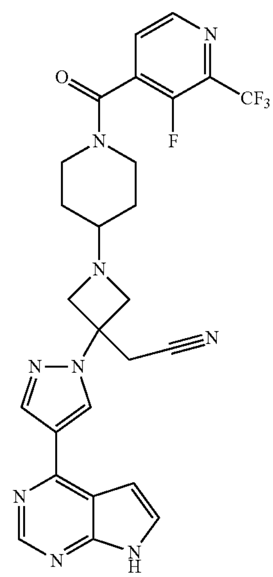 [SMILES: N#CCC1(n2cc(-c3ncnc4[nH]ccc34)cn2)CN(C2CCN(C(=O)c3ccnc(C(F)(F)F)c3F)CC2)C1] | + | >10 |
| 2 | US 2011/ 0224190 (Example 154) | 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl] piperidine-1-carboxamide | 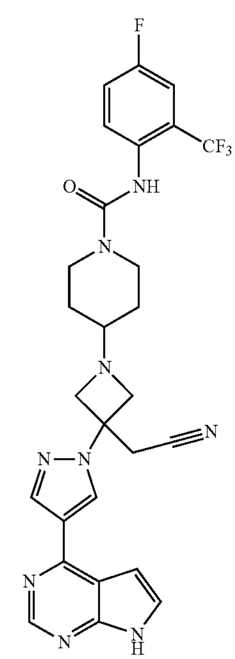 [SMILES: N#CCC1(n2cc(-c3ncnc4[nH]ccc34)cn2)CN(C2CCN(C(=O)Nc3ccc(F)cc3C(F)(F)F)CC2)C1] | + | >10 |

TABLE 1-continued

| Comp. No. | Prep. | Name | Structure | JAK1 IC$_{50}$ (nM) | JAK2/JAK1 |
|---|---|---|---|---|---|
| 3 | US 2011/0224190 (Example 85) | [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile | 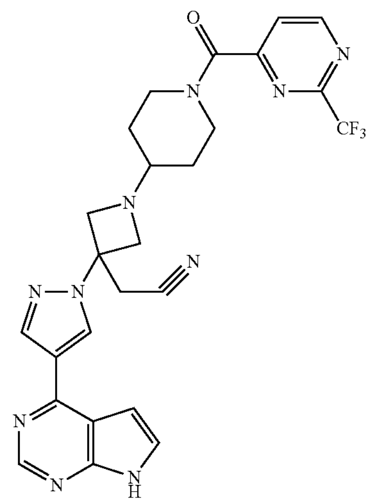 [SMILES: N#CCC1(n2cc(-c3ncnc4[nH]ccc34)cn2)CN(C2CCN(C(=O)c3ccnc(C(F)(F)F)n3)CC2)C1] | + | >10 |
| 4 | US 2014/0343030 (Example 7) | 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide | 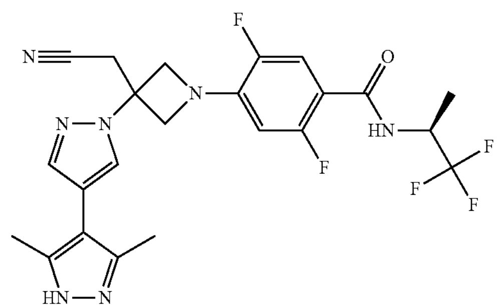 [SMILES: Cc1n[nH]c(C)c1-c1cnn(C2(CC#N)CN(c3cc(F)c(C(=O)N[C@@H](C)C(F)(F)F)cc3F)C2)c1] | +++ | >10 |
| 5 | US 2014/0121198 (Example 20) | ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile | 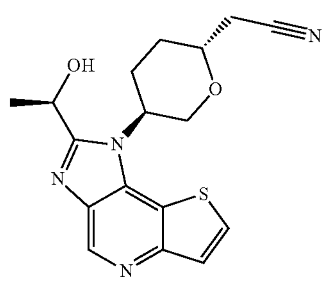 [SMILES: C[C@@H](O)c1nc2cnc3ccsc3c2n1[C@H]1CC[C@H](CC#N)OC1] | ++ | >10 |
| 6 | US 2010/0298334 (Example 2)$^a$ | 3-[1-(6-chloropyridin-2-yl)pyrrolidin-3-yl]-3-[4-(7H-pyrrolo[2,3-d]pyrimidin-4-yl)-1H-pyrazol-1-yl]propanenitrile | 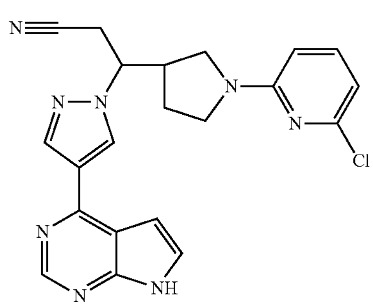 [SMILES: N#CCC(C1CCN(c2cccc(Cl)n2)C1)n1cc(-c2ncnc3[nH]ccc23)cn1] | + | >10 |

TABLE 1-continued

| Comp. No. | Prep. | Name | Structure | JAK1 IC$_{50}$ (nM) | JAK2/JAK1 |
|---|---|---|---|---|---|
| 7 | US 2010/ 0298334 (Example 13c) | 3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile | 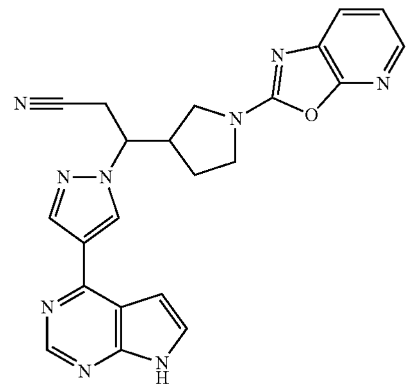 [SMILES: N#CCC(C1CCN(c2nc3cccnc3o2)C1)n1cc(-c2ncnc3[nH]ccc23)cn1] | + | >10 |
| 8 | US 2011/ 0059951 (Example 12) | 4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile | 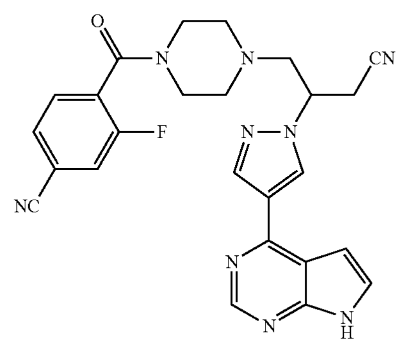 [SMILES: N#CCC(CN1CCN(C(=O)c2ccc(C#N)cc2F)CC1)n1cc(-c2ncnc3[nH]ccc23)cn1] | + | >10 |
| 9 | US 2011/ 0059951 (Example 13) | 4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile | 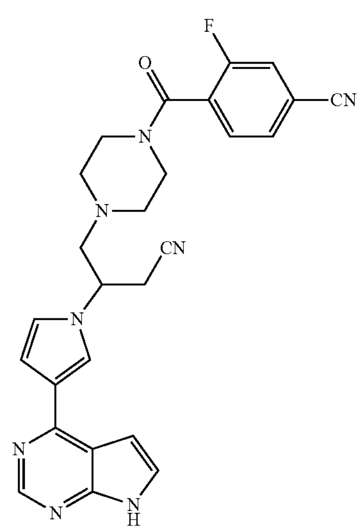 [SMILES: N#CCC(CN1CCN(C(=O)c2ccc(C#N)cc2F)CC1)n1ccc(-c2ncnc3[nH]ccc23)c1] | + | >10 |

TABLE 1-continued

| Comp. No. | Prep. | Name | Structure | JAK1 IC$_{50}$ (nM) | JAK2/JAK1 |
|---|---|---|---|---|---|
| 10 | US 2012/0149681 (Example 7b) | [trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile | 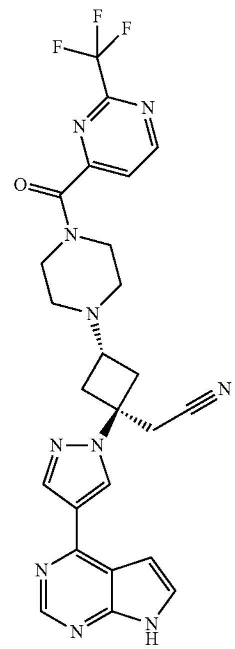 [SMILES: N#CC[C@]1(n2cc(-c3ncnc4[nH]ccc34)cn2)C[C@H](N2CCN(C(=O)c3ccnc(C(F)(F)F)n3)CC2)C1] | + | >10 |
| 11 | US 2012/0149681 (Example 157) | {trans-3-(4-{[4-[(3-hydroxyazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 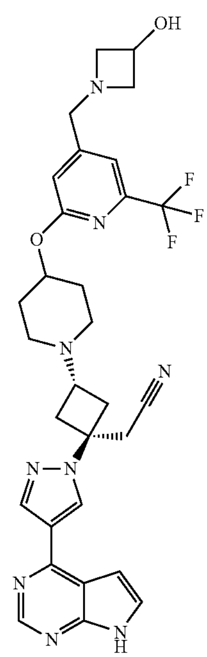 [SMILES: N#CC[C@]1(n2cc(-c3ncnc4[nH]ccc34)cn2)C[C@H](N2CCC(Oc3cc(CN4CC(O)C4)cc(C(F)(F)F)n3)CC2)C1] | + | >10 |

TABLE 1-continued

| Comp. No. | Prep. | Name | Structure | JAK1 IC$_{50}$ (nM) | JAK2/JAK1 |
|---|---|---|---|---|---|
| 12 | US 2012/ 0149681 (Example 161) | {trans-3-(4-{[4-{[(2S)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 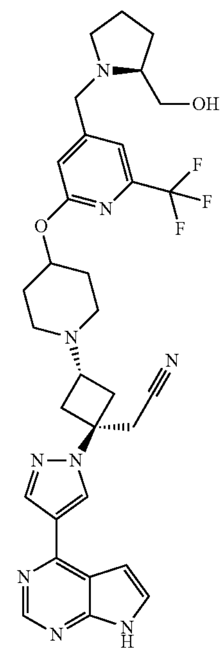 [SMILES: N#CC[C@]1(n2cc(-c3ncnc4[nH]ccc34)cn2)C[C@H](N2CCC(Oc3cc(CN4CCC[C@H]4CO)cc(C(F)(F)F)n3)CC2)C1] | + | >10 |
| 13 | US 2012/ 0149681 (Example 162) | {trans-3-(4-{[4-{[(2R)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 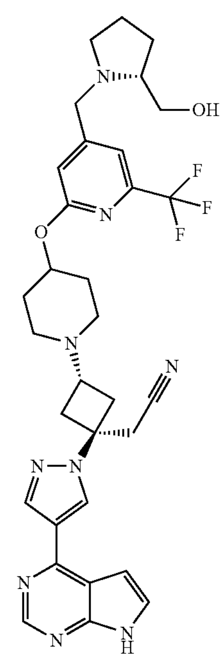 [SMILES: N#CC[C@]1(n2cc(-c3ncnc4[nH]ccc34)cn2)C[C@H](N2CCC(Oc3cc(CN4CCC[C@@H]4CO)cc(C(F)(F)F)n3)CC2)C1] | + | >10 |

TABLE 1-continued

| Comp. No. | Prep. | Name | Structure | JAK1 IC$_{50}$ (nM) | JAK2/JAK1 |
|---|---|---|---|---|---|
| 14 | US 2012/0149682 (Example 20)[b] | 4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile | 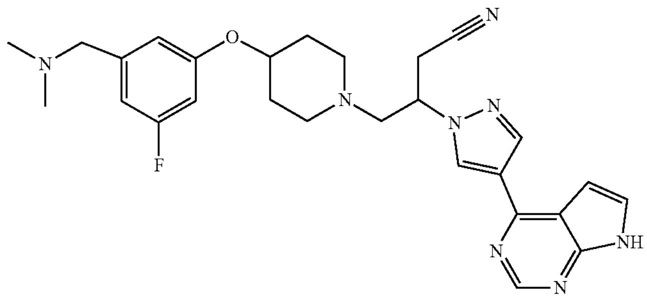 [SMILES: CN(C)Cc1cc(F)cc(OC2CCN(CC(CC#N)n3cc(-c4ncnc5[nH]ccc45)cn3)CC2)c1] | + | >10 |
| 15 | US 2013/0018034 (Example 18) | 5-{3-(cyanomethyl)-3-[4-(7H-pyrrolo[2,3-d]pyrimidin-4-yl)-1H-pyrazol-1-yl]azetidin-1-yl)-N-isopropylpyrazine-2-carboxamide | 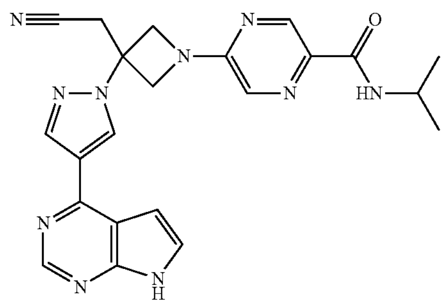 [SMILES: CC(C)NC(=O)c1cnc(N2CC(CC#N)(n3cc(-c4ncnc5[nH]ccc45)cn3)C2)cn1] | + | >10 |
| 16 | US 2013/0018034 (Example 28) | 4-{3-(cyanomethyl)-3-[4-(7H-pyrrolo[2,3-d]pyrimidin-4-yl)-1H-pyrazol-1-yl]azetidin-1-yl]-2,5-difluoro-N-[(1S)-2,2,2-trifluoro-1-methylethyl]benzamide | 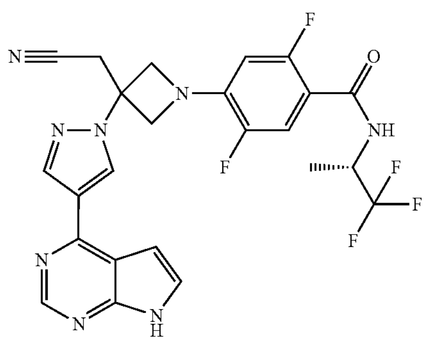 [SMILES: C[C@H](NC(=O)c1cc(F)c(N2CC(CC#N)(n3cc(-c4ncnc5[nH]ccc45)cn3)C2)cc1F)C(F)(F)F] | + | >10 |
| 17 | US 2013/0018034 (Example 34) | 5-{3-(cyanomethyl)-3-[4-(1H-pyrrolo[2,3-b]pyridin-4-yl)-1H-pyrazol-1-yl]azetidin-1-yl}-N-isopropylpyrazine-2-carboxamide | 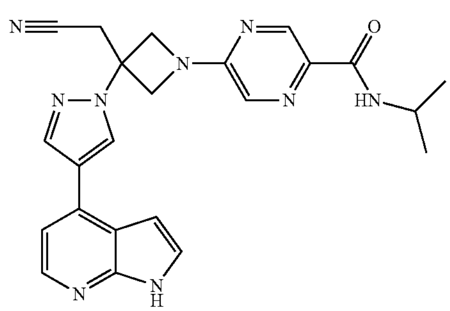 [SMILES: CC(C)NC(=O)c1cnc(N2CC(CC#N)(n3cc(-c4ccnc5[nH]ccc45)cn3)C2)cn1] | + | >10 |

TABLE 1-continued

| Comp. No. | Prep. | Name | Structure | JAK1 IC$_{50}$ (nM) | JAK2/JAK1 |
|---|---|---|---|---|---|
| 18 | US 2013/0045963 (Example 45) | {1-(cis-4-([6-(2-hydroxyethyl)-2-(trifluoromethyl)pyrimidin-4-yl]oxy)cyclohexyl)-3-[4-(7H-pyrrolo[2,3-d]pyrimidin-4-yl)-1H-pyrazol-1-yl]azetidin-3-yl}acetonitrile | 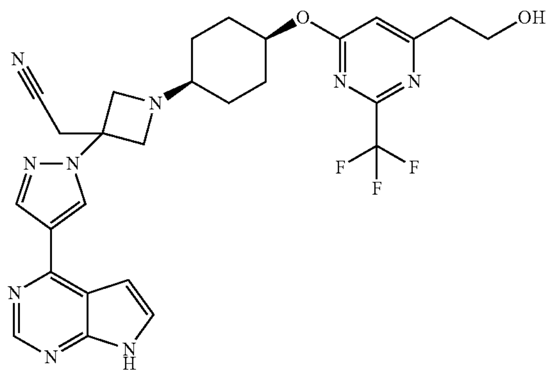 [SMILES: N#CCC1(n2cc(-c3ncnc4[nH]ccc34)cn2)CN([C@H]2CC[C@@H](Oc3cc(CCO)nc(C(F)(F)F)n3)CC2)C1] | + | >10 |
| 19 | US 2013/0045963 (Example 65) | {1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 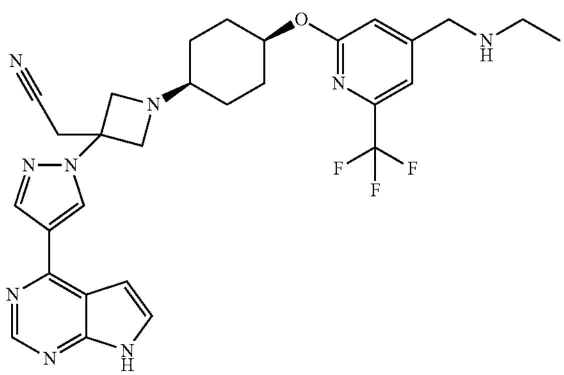 [SMILES: CCNCc1cc(O[C@H]2CC[C@@H](N3CC(CC#N)(n4cc(-c5ncnc6[nH]ccc56)cn4)C3)CC2)nc(C(F)(F)F)c1] | + | >10 |
| 20 | US 2013/0045963 (Example 69) | {1-(cis-4-{[4-(1-hydroxy-1-methylethyl)-6-(trifluoromethyl)pyridin-2-yl]oxy]cyclohexyl)-3-[4-(7H-pyrrolo[2,3-d]pyrimidin-4-yl)-1H-pyrazol-1-yl]azetidin-3-yl}acetonitrile | 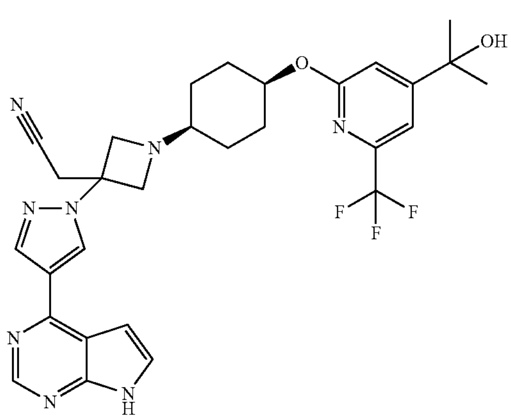 [SMILES: CC(C)(O)c1cc(O[C@H]2CC[C@@H](N3CC(CC#N)(n4cc(-c5ncnc6[nH]ccc56)cn4)C3)CC2)nc(C(F)(F)F)c1] | + | >10 |

TABLE 1-continued

| Comp. No. | Prep. | Name | Structure | JAK1 IC$_{50}$ (nM) | JAK2/ JAK1 |
|---|---|---|---|---|---|
| 21 | US 2013/ 0045963 (Example 95) | {1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 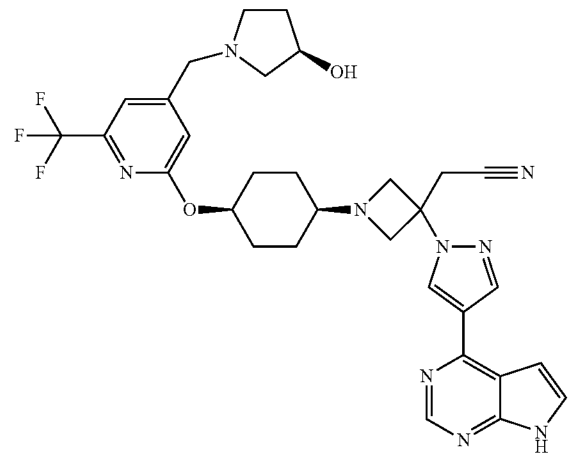 [SMILES: N#CCC1(n2cc(-c3ncnc4[nH]ccc34)cn2)CN([C@H]2CC[C@@H](Oc3cc(CN4CC[C@@H](O)C4)cc(C(F)(F)F)n3)CC2)C1] | + | >10 |
| 22 | US 2013/ 0045963 (Example 95) | {1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 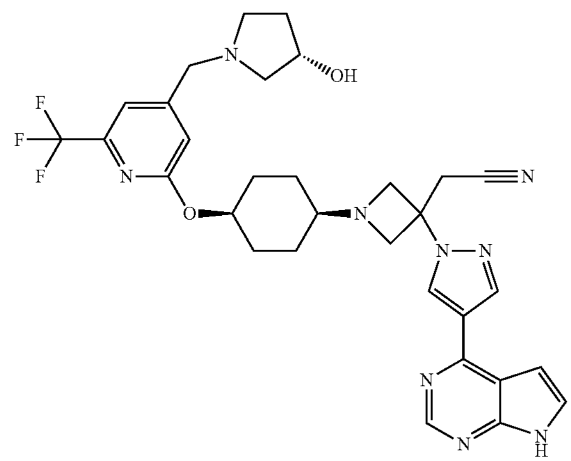 [SMILES: N#CCC1(n2cc(-c3ncnc4[nH]ccc34)cn2)CN([C@H]2CC[C@@H](Oc3cc(CN4CC[C@H](O)C4)cc(C(F)(F)F)n3)CC2)C1] | + | >10 |
| 23 | US 2014/ 0005166 (Example 1) | {trans-3-(4-{[4-({[(1S)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 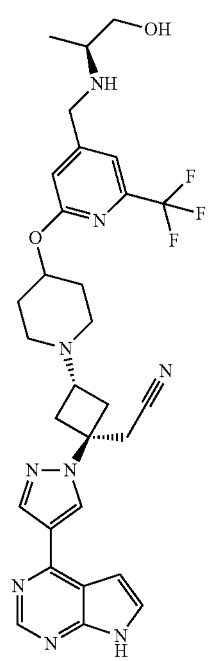 [SMILES: C[C@@H](CO)NCc1cc(OC2CCN([C@H]3C[C@](CC#N)(n4cc(-c5ncnc6[nH]ccc56)cn4)C3)CC2)nc(C(F)(F)F)c1] | + | >10 |

TABLE 1-continued

| Comp. No. | Prep. | Name | Structure | JAK1 IC$_{50}$ (nM) | JAK2/ JAK1 |
|---|---|---|---|---|---|
| 24 | US 2014/ 0005166 (Example 14) | {trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl]acetonitrile | 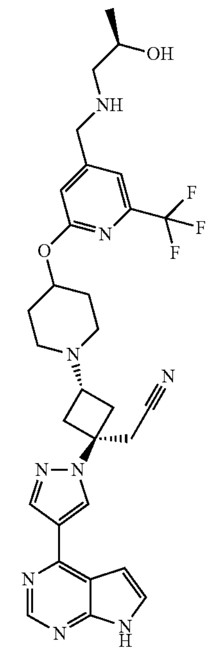 [SMILES: C[C@@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |
| 25 | US 2014/ 0005166 (Example 15) | {trans-3-(4-{[4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 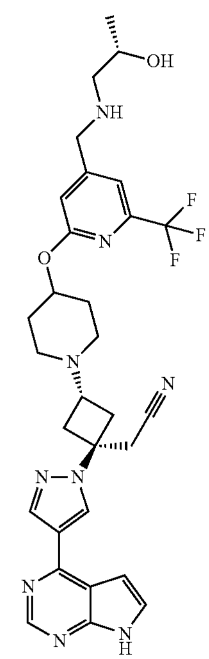 [SMILES: C[C@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |

TABLE 1-continued

| Comp. No. | Prep. | Name | Structure | JAK1 IC$_{50}$ (nM) | JAK2/ JAK1 |
|---|---|---|---|---|---|
| 26 | US 2014/ 0005166 (Example 20) | {trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 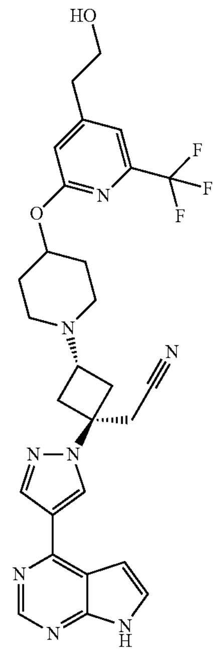 [SMILES: N#CC[C@]1(n2cc(-c3ncnc4[nH]ccc34)cn2)C[C@H](N2CCC(Oc3cc(CCO)cc(C(F)(F)F)n3)CC2)C1] | + | >10 |

+ means <10 nM (see Example 1 for assay conditions)
++ means ≤100 nM (see Example 1 for assay conditions)
+++ means ≤300 nM (see Example 1 for assay conditions)
$^a$Data for enantiomer 1
$^b$Data for enantiomer 2

In some embodiments, the JAK1 inhibitor, or the pharmaceutically acceptable salt thereof, is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile, or a pharmaceutically acceptable salt thereof. In some embodiments, the JAK1 inhibitor, or the pharmaceutically acceptable salt thereof, is a JAK1 inhibitor, which is {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile adipic acid salt. The synthesis and preparation of {1-{1-[3-fluoro-2-(trifluoromethyl)isonicotinoyl]piperidin-4-yl}-3[4-(7H-pyrrolo[2,3-d]pyrimidin-4-yl)-1H-pyrazol-1-yl]azetidin-3-yl}acetonitrile and the adipic acid salt of the same can be found, e.g., in US Patent Publ. No. 2011/0224190, filed Mar. 9, 2011, US Patent Publ. No. 2013/0060026, filed Sep. 6, 2012, and US Patent Publ. No. 2014/0256941, filed Mar. 5, 2014, each of which is incorporated herein by reference in its entirety.

In some embodiments, the JAK1 inhibitor, or the pharmaceutically acceptable salt thereof, is a JAK1 inhibitor, which is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or a pharmaceutically acceptable salt thereof. In some embodiments, the JAK1 inhibitor, or the pharmaceutically acceptable salt thereof, is a JAK1 inhibitor, which is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt. In some embodiments, the JAK1 inhibitor, or the pharmaceutically acceptable salt thereof, is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide hydrochloric acid salt. In some embodiments, the JAK1 inhibitor, or the pharmaceutically acceptable salt thereof, is 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide hydrobromic acid salt. In some embodiments, the JAK1 inhibitor, or the pharmaceutically acceptable salt thereof, is s 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide sulfuric acid salt. The synthesis and preparation of 4-[3-(cyanomethyl)-3-(3',5'-dimethyl-1H, 1'H-4,4'-bipyrazol-1-yl)azetidin-1-yl]-2,5-difluoro-N-[(1S)-2,2,2-trifluoro-1-methylethyl]benzamide and the phosphoric acid salt of the same can be found, e.g., in US Patent Publ. No. US 2014/0343030, filed May 16, 2014, which is incorporated herein by reference in its entirety.

In some embodiments, the JAK1 inhibitor, or the pharmaceutically acceptable salt thereof, is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile, or a pharmaceutically acceptable salt thereof.

In some embodiments, the JAK1 inhibitor, or the pharmaceutically acceptable salt thereof, is ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrilemonohydrate, or a pharmaceutically acceptable salt thereof. Synthesis of ((2R, 5S)-5-{2-[(1R)-1-hydroxyethyl]-1H-imidazo[4,5-d]thieno[3,2-b]pyridin-1-yl}tetrahydro-2H-pyran-2-yl)acetonitrile and characterization of the anhydrous and monohydrate forms of the same are described in US Patent Publ. No. 2014/0121198, filed Oct. 31, 2013 and US Patent Publ. No. 2015/0344497, filed Apr. 29, 2015, each of which is incorporated herein by reference in its entirety.

In some embodiments, the compounds of Table 1 are prepared by the synthetic procedures described in US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, the JAK1 inhibitor, or the pharmaceutically acceptable salt thereof, is selected from the compounds, or pharmaceutically acceptable salts thereof, of US Patent Publ. No. 2011/0224190, filed Mar. 9, 2011, US Patent Publ. No. 2014/0343030, filed May 16, 2014, US Patent Publ. No. 2014/0121198, filed Oct. 31, 2013, US Patent Publ. No. 2010/0298334, filed May 21, 2010, US Patent Publ. No. 2011/0059951, filed Aug. 31, 2010, US Patent Publ. No. 2012/0149681, filed Nov. 18, 2011, US Patent Publ. No. 2012/0149682, filed Nov. 18, 2011, US Patent Publ. 2013/0018034, filed Jun. 19, 2012, US Patent Publ. No. 2013/0045963, filed Aug. 17, 2012, and US Patent Publ. No. 2014/0005166, filed May 17, 2013, each of which is incorporated herein by reference in its entirety.

In some embodiments, the JAK inhibitor, is brepocitinib, or a pharmaceutically acceptable salt thereof. Brepocitinib is a JAK1/JAK2 inhibitor.

In some embodiments, the JAK inhibitor, or the pharmaceutically acceptable salt thereof, is ATI-501, or a pharmaceutically acceptable salt thereof. ATI-501 (Aclaris) is a JAK1/JAK3 inhibitor.

In some embodiments, the JAK inhibitor, or the pharmaceutically acceptable salt thereof, is ATI-1777, or a pharmaceutically acceptable salt thereof. ATI-1777 (Aclaris) is a JAK1/JAK3 inhibitor.

In some embodiments, the JAK inhibitor, or the pharmaceutically acceptable salt thereof, is ATI-502, or a pharmaceutically acceptable salt thereof. ATI-502 (Aclaris) is a JAK1/JAK3 inhibitor.

In some embodiments, the JAK inhibitor, or the pharmaceutically acceptable salt thereof, is tofacitinib, or a pharmaceutically acceptable salt thereof. Tofacinitib inhibits JAK1 and JAK3.

In some embodiments, the JAK inhibitor, or the pharmaceutically acceptable salt thereof, is delgocitinib, or a pharmaceutically acceptable salt thereof. Delgocitinib is a pan-JAK inhibitor.

In some embodiments, the JAK inhibitor, or the pharmaceutically acceptable salt thereof, is peficitinib, or a pharmaceutically acceptable salt thereof. Peficitinib is a pan-JAK inhibitor.

In some embodiments, the JAK inhibitor, or the pharmaceutically acceptable salt thereof, is gusacitinib, or a pharmaceutically acceptable salt thereof. Gusacitinib is a pan-JAK inhibitor that also inhibits SYK.

In some embodiments, the JAK inhibitor, or the pharmaceutically acceptable salt thereof, is cucurbitacin I, or a pharmaceutically acceptable salt thereof. Cucurbitacin I is a pan-JAK inhibitor which also inhibits STAT3.

In some embodiments, the JAK inhibitor, or the pharmaceutically acceptable salt thereof, is cerdulatinib, or a pharmaceutically acceptable salt thereof. Cerdulatinib is a pan-JAK inhibitor, which also inhibits spleen tyrosine kinase (SYK).

In some embodiments, the JAK inhibitor, or the pharmaceutically acceptable salt thereof, is decernotinib, or a pharmaceutically acceptable salt thereof. Decernotinib is a JAK3 inhibitor.

In some embodiments, the JAK inhibitor, or the pharmaceutically acceptable salt thereof, is BMS-986165 having the structure below:

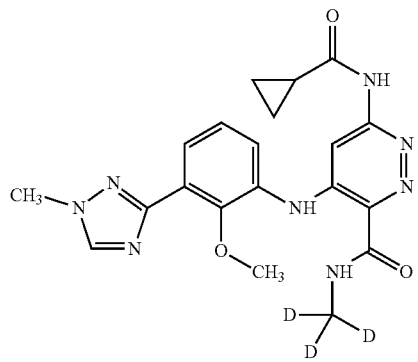 [SMILES: [2H]C([2H])([2H])NC(=O)c1nnc(NC(=O)C2CC2)cc1Nc1cccc(-c2ncn(C)n2)c1OC]

or a pharmaceutically acceptable salt thereof. BMS-986165 is a TYK2 inhibitor.

In some embodiments, the JAK inhibitor, or the pharmaceutically acceptable salt thereof, is ritlecitinib, or a pharmaceutically acceptable salt thereof. Ritlecitinib (Pfizer) is a JAK3 inhibitor, which also inhibits TEC.

In some embodiments, provided are the methods as described herein, wherein the JAK inhibitor, or the pharmaceutically acceptable salt thereof, is selected from ruxolitinib, oclacitinib, baricitinib, momelotinib, and CTP-543, or a pharmaceutically acceptable salt thereof.

In some embodiments, the JAK inhibitor, or the pharmaceutically acceptable salt thereof, is selected from ruxolitinib, oclacitinib, baricitinib, momelotinib, CTP-543, gandotinib, fedratinib, lestaurtinib, pacritinib, upadacitinib, tofacitinib, filgocitinib, abrocitinib, itacitinib, brepocitinib, ATI-501, ATI-1777, ATI-502, delgocitinib, peficitinib, gusacitinib, cucurbitacin I, and cerdulatinib, or a pharmaceutically acceptable salt thereof.

In some embodiments, the JAK inhibitor, or the pharmaceutically acceptable salt thereof, is selected from ruxolitinib, oclacitinib, baricitinib, momelotinib, CTP-543, gandotinib, fedratinib, lestaurtinib, pacritinib, upadacitinib, tofacitinib, filgocitinib, abrocitinib, itacitinib, brepocitinib, delgocitinib, peficitinib, gusacitinib, cucurbitacin I, and cerdulatinib, or a pharmaceutically acceptable salt thereof.

In some embodiments, the JAK inhibitor, or the pharmaceutically acceptable salt thereof, can be an isotopically-labeled compound, or a pharmaceutically acceptable salt thereof. An "isotopically" or "radio-labeled" compound is a compound wherein one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}$Cl, $^{82}$Br, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms, such as —CD$_3$ being substituted for —CH$_3$).

Accordingly, in some embodiments, the JAK inhibitor, or the pharmaceutically acceptable salt thereof, is a compound, wherein one or more hydrogen atoms in the compound are replaced by deuterium atoms, or a pharmaceutically acceptable salt thereof.

In some embodiments, provided are the methods as described herein, wherein the JAK inhibitor, or the pharmaceutically acceptable salt thereof, is combined with any of the JAK inhibitors, or a pharmaceutically acceptable salt thereof, as described herein.

In some embodiments, provided are the methods as described herein, wherein (a) the JAK inhibitor, or the pharmaceutically acceptable salt thereof, is administered in a therapeutically effective amount.

In some embodiments, the JAK inhibitor, or the pharmaceutically acceptable salt thereof, is administered as a topical formulation. In some embodiments, the topical formulation comprises from about 0.1% to about 3.0%, about 0.1% to about 2.0%, from about 0.1% to about 1.5%, from about 0.1% to about 1.0%, from about 0.1% to about 0.5%, from about 0.5% to about 2.0%%, from about 0.5% to about 1.5%, or from about 0.5% to about 1.0% by weight of the formulation on a free base basis of the JAK inhibitor, or the pharmaceutically acceptable salt thereof. In some embodiments, the topical formulation comprises from about 0.5% to about 1.5% by weight of the formulation on a free base basis of the JAK inhibitor, or the pharmaceutically acceptable salt thereof. In some embodiments, the topical formulation comprises about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1.0%, about 1.05%, about 1.1%, about 1.15%, about 1.2%, about 1.25%, about 1.3%, about 1.35%, about 1.4%, about 1.45%, about 1.5%, about 1.55%, about 1.6%, about 1.65%, about 1.7%, about 1.75%, about 1.8%, about 1.85%, about 1.9%, about 1.95%, about 2.0%, about 2.5%, or about 3.0% by weight of the formulation on a free base basis of the JAK inhibitor, or the pharmaceutically acceptable salt thereof.

Cream Formulations of Ruxolitinib

In some embodiments, the ruxolitinib, or pharmaceutically acceptable salt thereof, is administered as a cream formulation comprising the ruxolitinib, or the pharmaceutically acceptable salt thereof.

In some embodiments, the ruxolitinib, or pharmaceutically acceptable salt thereof, is administered as a cream formulation comprising ruxolitinib phosphate.

In some embodiments, the ruxolitinib, or the pharmaceutically acceptable salt thereof, is in a form of a cream formulation. In some embodiments, the cream formulation is an oil-in-water emulsion. In some embodiments, the cream formulation is described in U.S. Pat. No. 10,758,543, which is incorporated by reference in its entirety. In particular, Examples 3-6 of U.S. Pat. No. 10,758,543 (and particularly Tables 3-5 and accompanying text) are incorporated herein by reference. In some embodiments, the cream comprises from about 0.1% to about 3.0%, from about 0.1% to about 3.0%, from about 0.1% to about 1.5%, from about 0.1% to about 1.0%, from about 0.1% to about 0.5%, from about 0.5% to about 2.0%%, from about 0.5% to about 1.5%, from about 0.5% to about 1.4%, from about 0.5% to about 1.3%, from about 0.5% to about 1.2%, from about 0.5% to about 1.1%, from about 0.6% to about 2.0%%, from about 0.6% to about 1.5%, from about 0.6% to about 1.4%, from about 0.6% to about 1.3%, from about 0.6% to about 1.2%, from about 0.6% to about 1.1%, from about 0.7% to about 2.0%%, from about 0.7% to about 1.5%, from about 0.7% to about 1.4%, from about 0.7% to about 1.3%, from about 0.7% to about 1.2%, from about 0.7% to about 1.1%, from about 0.8% to about 2.0%%, from about 0.8% to about 1.5%, from about 0.8% to about 1.4%, from about 0.8% to about 1.3%, from about 0.8% to about 1.2%, from about 0.8% to about 1.1%, from about 0.9% to about 2.0%%, from about 0.9% to about 1.5%, from about 0.9% to about 1.4%, from about 0.9% to about 1.3%, from about 0.9% to about 1.2%, from about 0.9% to about 1.1%, from about 1.0% to about 2.0%%, from about 1.0% to about 1.5%, from about 1.0% to about 1.4%, from about 1.0% to about 1.3%, from about 1.0% to about 1.2%, from about 1.0% to about 1.1%, or from about 0.5% to about 1.0% by weight of the emulsion on a free base basis of the ruxolitinib, or the pharmaceutically acceptable salt thereof. In some embodiments, the oil-in-water emulsion comprises from about 0.5% to about 1.5% by weight of the emulsion on a free base basis of the ruxolitinib, or the pharmaceutically acceptable salt thereof. In some embodiments, the oil-in-water emulsion comprises about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1.0%, about 1.05%, about 1.1%, about 1.15%, about 1.2%, about 1.25%, about 1.3%, about 1.35%, about 1.4%, about 1.45%, about 1.5%, about 1.55%, about 1.6%, about 1.65%, about 1.7%, about 1.75%, about 1.8%, about 1.85%, about 1.9%, about 1.95%, or 2.0% by weight of the emulsion on a free base basis of the ruxolitinib, or the pharmaceutically acceptable salt thereof. In some embodiments, the ruxolitinib, or the pharmaceutically acceptable salt thereof, is ruxolitinib phosphate.

In some embodiments, the cream formulation has a pH from about 6.5 to about 7.0.

In some embodiments, the cream formulation has a pH from about 2.8 to about 3.9.

In some embodiments, the cream formulation has a pH from about 2.8 to about 3.6.

In some embodiments, the cream comprises an oil-in-water emulsion, comprising ruxolitinib.

In some embodiments, the cream comprises an oil-in-water emulsion, comprising ruxolitinib phosphate. In some embodiments, the cream is an oil-in-water emulsion as described in US 2015/0250790, which is incorporated herein by reference in its entirety. In particular, Examples 3-6 of US 2015/0250790 (and particularly Tables 3-5 and accompanying text) are incorporated herein by reference.

In some embodiments, the oil component is present in an amount of about 10% to about 40% by weight of the emulsion.

In some embodiments, the oil component is present in an amount of about 10% to about 24% by weight of the emulsion.

In some embodiments, the oil component is present in an amount of about 15% to about 24% by weight of the emulsion.

In some embodiments, the oil component is present in an amount of about 18% to about 24% by weight of the emulsion.

In some embodiments, the oil component comprises one or more substances independently selected from petrolatums, fatty alcohols, mineral oils, triglycerides, and silicone oils.

In some embodiments, the oil component comprises one or more substances independently selected from white petrolatum, cetyl alcohol, stearyl alcohol, light mineral oil, medium chain triglycerides, and dimethicone.

In some embodiments, the oil component comprises an occlusive agent component.

In some embodiments, the occlusive agent component is present in an amount of about 2% to about 15% by weight of the emulsion.

In some embodiments, the occlusive agent component is present in an amount of about 5% to about 10% by weight of the emulsion.

In some embodiments, the occlusive agent component comprises one or more substances selected from fatty acids (e.g., lanolin acid), fatty alcohols (e.g., lanolin alcohol), hydrocarbon oils & waxes (e.g., petrolatum), polyhydric alcohols (e.g., propylene glycol), silicones (e.g., dimethicone), sterols (e.g., cholesterol), vegetable or animal fat (e.g., cocoa butter), vegetable wax (e.g., Carnauba wax), and wax ester (e.g., bees wax).

In some embodiments, the occlusive agent component comprises one or more substances selected from lanolin acid fatty alcohols, lanolin alcohol, petrolatum, propylene glycol, dimethicone, cholesterol, cocoa butter, Carnauba wax, and bees wax.

In some embodiments, the occlusive agent component comprises petrolatum.

In some embodiments, the occlusive agent component comprises white petrolatum.

In some embodiments, the white petrolatum is present in an amount of about 0.1% to about 15% by weight of the emulsion.

In some embodiments, the white petrolatum is present in an amount of about 7% by weight of the emulsion.

In some embodiments, the oil component comprises a stiffening agent component.

In some embodiments, the stiffening agent component is present in an amount of about 2% to about 8% by weight of the emulsion.

In some embodiments, the stiffening agent component is present in an amount of about 3% to about 6% by weight of the emulsion.

In some embodiments, the stiffening agent component is present in an amount of about 4% to about 7% by weight of the emulsion.

In some embodiments, the stiffening agent component comprises one or more substances independently selected from fatty alcohols.

In some embodiments, the stiffening agent component comprises one or more substances independently selected from $C_{12-20}$ fatty alcohols.

In some embodiments, the stiffening agent component comprises one or more substances independently selected from $C_{16-18}$ fatty alcohols.

In some embodiments, the stiffening agent component comprises one or more substances independently selected from cetyl alcohol and stearyl alcohol.

In some embodiments, the cetyl alcohol is present in an amount of about 0.1% to about 15% by weight of the emulsion.

In some embodiments, the cetyl alcohol in an amount of about 3% by weight of the emulsion.

In some embodiments, the stearyl alcohol is present in an amount of about 0.1% to about 15% by weight of the emulsion.

In some embodiments, the stearyl alcohol is present in an amount of about 1.75% by weight of the emulsion.

In some embodiments, the stiffening agent component comprises one or more substances independently selected from cetyl alcohol, stearyl alcohol, oleyl alcohol, and cetosteryl alcohol.

In some embodiments, the cetosteryl alcohol is present in an amount of about 0.1% to about 30% by weight of the emulsion.

In some embodiments, the cetosteryl alcohol is present in an amount of about 1% to about 20% by weight of the emulsion.

In some embodiments, the oil component comprises an emollient component.

In some embodiments, the emollient component is present in an amount of about 5% to about 15% by weight of the emulsion.

In some embodiments, the emollient component is present in an amount of about 7% to about 13% by weight of the emulsion.

In some embodiments, the emollient component comprises one or more substances independently selected from mineral oils and triglycerides.

In some embodiments, the emollient component comprises one or more substances independently selected from light mineral oil and medium chain triglycerides.

In some embodiments, the light mineral oil is present in an amount of about 0.1% to about 15% by weight of the emulsion.

In some embodiments, the light mineral oil is present in an amount of about 4% by weight of the emulsion.

In some embodiments, the emollient component comprises one or more substances independently selected from light mineral oil, medium chain triglycerides, and dimethicone.

In some embodiments, the dimethicone is present in an amount of about 0.1% to about 15% by weight of the emulsion.

In some embodiments, the dimethicone is present in an amount of about 1% by weight of the emulsion.

In some embodiments, the medium chain triglycerides are in an amount of about 0.1% to about 15% by weight of the emulsion.

In some embodiments, the medium chain triglycerides are in an amount of about 7.0% by weight of the emulsion.

In some embodiments, the water is present in an amount of about 35% to about 65% by weight of the emulsion.

In some embodiments, the water is present in an amount of about 40% to about 60% by weight of the emulsion.

In some embodiments, the water is present in an amount of about 45% to about 55% by weight of the emulsion.

In some embodiments, the emulsifier component is present in an amount of about 1% to about 9% by weight of the emulsion.

In some embodiments, the emulsifier component is present in an amount of about 2% to about 6% by weight of the emulsion.

In some embodiments, the emulsifier component is present in an amount of about 3% to about 5% by weight of the emulsion.

In some embodiments, the emulsifier component is present in an amount of about 4% to about 7% by weight of the emulsion.

In some embodiments, the emulsion comprises an emulsifier component and a stiffening agent component, wherein the combined amount of emulsifier component and stiffening agent component is at least about 8% by weight of the emulsion.

In some embodiments, the emulsifier component comprises one or more substances independently selected from glyceryl fatty esters and sorbitan fatty esters.

In some embodiments, the emulsifier component comprises one or more substances independently selected from glyceryl stearate, and polysorbate 20.

In some embodiments, the glyceryl stearate is present in an amount of about 0.1% to about 15% by weight of the emulsion.

In some embodiments, the glyceryl stearate is present in an amount of about 3% by weight of the emulsion.

In some embodiments, the polysorbate 20 is present in an amount of about 0.1% to about 15% by weight of the emulsion.

In some embodiments, the polysorbate 20 is present in an amount of about 1.25% by weight of the emulsion.

In some embodiments, the emulsifier component comprises a non-ionic surfactant.

In some embodiments, the non-ionic surfactant is cetomacrogol 1000 or poloxamer 407.

In some embodiments, the cetomacrogol 1000 is present in an amount of about 0.01% to about 15% by weight of the emulsion.

In some embodiments, the cetomacrogol 1000 is present in an amount of about 0.1% to about 10% by weight of the emulsion.

In some embodiments, the poloxamer is poloxamer 407.

In some embodiments, the poloxamer 407 is present in an amount of about 0.01% to about 15% by weight of the emulsion.

In some embodiments, the emulsifier component further comprises glyceryl stearate and PEG-100 stearate, such as Arlacel™ 165

In some embodiments, the glyceryl stearate and PEG-100 stearate is present in an amount of about 0.1% to about 15% by weight of the emulsion.

In some embodiments, the emulsion further comprises a stabilizing agent component.

In some embodiments, the stabilizing agent component is present in an amount of about 0.05% to about 5% by weight of the emulsion.

In some embodiments, the stabilizing agent component is present in an amount of about 0.1% to about 2% by weight of the emulsion.

In some embodiments, the stabilizing agent component is present in an amount of about 0.3% to about 0.5% by weight of the emulsion.

In some embodiments, the stabilizing agent component comprises one or more substances independently selected from polysaccharides.

In some embodiments, the stabilizing agent component comprises xanthan gum.

In some embodiments, the xanthan gum is present in an amount of about 0.001% to about 5% by weight of the emulsion.

In some embodiments, the xanthan gum is present in an amount of about 0.2% to about 0.6% by weight of the emulsion.

In some embodiments, the xanthan gum is present in an amount of about 0.4%. by weight of the emulsion.

In some embodiments, the emulsion further comprises a solvent component.

In some embodiments, the solvent component is present in an amount of about 10% to about 35% by weight of the emulsion.

In some embodiments, the solvent component is present in an amount of about 15% to about 30% by weight of the emulsion.

In some embodiments, the solvent component is present in an amount of about 20% to about 25% by weight of the emulsion.

In some embodiments, the solvent component comprises one or more substances independently selected from alkylene glycols and polyalkylene glycols.

In some embodiments, the solvent component comprises one or more substances independently selected from propylene glycol and polyethylene glycol.

In some embodiments, the solvent component comprises one or more substances independently selected from PEG200, PEG300, PEG400, propylene glycol.

In some embodiments, the solvent component comprises PEG300 and propylene glycol.

In some embodiments, the PEG300 is present in an amount of about 7% w/w by weight of the emulsion.

In some embodiments, the solvent is a combination of PEG400 and propylene glycol.

In some embodiments, the PEG400 is present in an amount of about 7% by weight of the emulsion.

In some embodiments, the propylene glycol is present of about 6.5% by weight of the emulsion. In some embodiments, the solvent component comprises diethylene glycol monoethyl ether, such as Transcutol® P. In some embodiments, the diethylene glycol monoethyl ether is present in an amount of about 0.1% to about 30% w/w by weight of the emulsion. In some embodiments, the diethylene glycol monoethyl ether is present in an amount of about 0.1% to about 20% w/w by weight of the emulsion.

In some embodiments, the emulsion further comprises:
from about 35% to about 65% of water by weight of the emulsion;
from about 10% to about 40% of an oil component by weight of the emulsion;
from about 1% to about 9% of an emulsifier component by weight of the emulsion;
from about 10% to about 35% of a solvent component by weight of the emulsion; and
from about 0.05% to about 5% of a stabilizing agent component by weight of the emulsion.

In some embodiments, the emulsion comprises:
from about 35% to about 65% of water by weight of the emulsion;
from about 10% to about 40% of an oil component by weight of the emulsion;
from about 1% to about 9% of an emulsifier component by weight of the emulsion;
from about 10% to about 35% of a solvent component by weight of the emulsion; from about 0.05% to about 5% of a stabilizing agent component by weight of the emulsion; and
from 0.5% to 1.5% of ruxolitinib, or a pharmaceutically acceptable salt thereof, by weight of the emulsion on a free base basis.

In some embodiments, the emulsion further comprises:
from about 35% to about 65% of water by weight of the emulsion;
from about 10% to about 24% of an oil component by weight of the emulsion;
from about 1% to about 9% of an emulsifier component by weight of the emulsion;

from about 10% to about 35% of a solvent component by weight of the emulsion; and
from about 0.05% to about 5% of a stabilizing agent component by weight of the emulsion.

In some embodiments, the emulsion comprises:
from about 35% to about 65% of water by weight of the emulsion;
from about 10% to about 24% of an oil component by weight of the emulsion;
from about 1% to about 9% of an emulsifier component by weight of the emulsion;
from about 10% to about 35% of a solvent component by weight of the emulsion;
from about 0.05% to about 5% of a stabilizing agent component by weight of the emulsion; and
from 0.5% to 1.5% of ruxolitinib, or a pharmaceutically acceptable salt thereof, by weight of the emulsion on a free base basis.

In some embodiments, the emulsion further comprises:
from about 40% to about 60% of water by weight of the emulsion;
from about 15% to about 30% of an oil component by weight of the emulsion;
from about 2% to about 6% of an emulsifier component by weight of the emulsion;
from about 15% to about 30% of a solvent component by weight of the emulsion; and
from about 0.1% to about 2% of a stabilizing agent component by weight of the emulsion.

In some embodiments, the emulsion comprises:
from about 40% to about 60% of water by weight of the emulsion;
from about 15% to about 30% of an oil component by weight of the emulsion;
from about 2% to about 6% of an emulsifier component by weight of the emulsion;
from about 15% to about 30% of a solvent component by weight of the emulsion;
from about 0.1% to about 2% of a stabilizing agent component by weight of the emulsion; and
from 0.5% to 1.5% of ruxolitinib, or a pharmaceutically acceptable salt thereof, by weight of the emulsion on a free base basis.

In some embodiments, the emulsion further comprises:
from about 40% to about 60% of water by weight of the emulsion;
from about 15% to about 30% of an oil component by weight of the emulsion;
from about 2% to about 6% of an emulsifier component by weight of the emulsion;
from about 15% to about 24% of a solvent component by weight of the emulsion; and
from about 0.1% to about 2% of a stabilizing agent component by weight of the emulsion.

In some embodiments, the emulsion comprises:
from about 40% to about 60% of water by weight of the emulsion;
from about 15% to about 30% of an oil component by weight of the emulsion;
from about 2% to about 6% of an emulsifier component by weight of the emulsion;
from about 15% to about 24% of a solvent component by weight of the emulsion;
from about 0.1% to about 2% of a stabilizing agent component by weight of the emulsion; and
from 0.5% to 1.5% of ruxolitinib, or a pharmaceutically acceptable salt thereof, by weight of the emulsion on a free base basis.

In some embodiments, the emulsion further comprises:
from about 45% to about 55% of water by weight of the emulsion;
from about 15% to about 24% of an oil component by weight of the emulsion;
from about 3% to about 5% of an emulsifier component by weight of the emulsion;
from about 20% to about 25% of a solvent component by weight of the emulsion; and
from about 0.3% to about 0.5% of a stabilizing agent component by weight of the emulsion.

In some embodiments, the emulsion comprises:
from about 45% to about 55% of water by weight of the emulsion;
from about 15% to about 24% of an oil component by weight of the emulsion;
from about 3% to about 5% of an emulsifier component by weight of the emulsion;
from about 20% to about 25% of a solvent component by weight of the emulsion;
from about 0.3% to about 0.5% of a stabilizing agent component by weight of the emulsion; and
from 0.5% to 1.5% of ruxolitinib, or a pharmaceutically acceptable salt thereof, by weight of the emulsion on a free base basis.

In some embodiments, the emulsion further comprises:
from about 45% to about 55% of water by weight of the emulsion;
from about 15% to about 24% of an oil component by weight of the emulsion;
from about 4% to about 7% of an emulsifier component by weight of the emulsion;
from about 20% to about 25% of a solvent component by weight of the emulsion; and
from about 0.3% to about 0.5% of a stabilizing agent component by weight of the emulsion.

In some embodiments, the emulsion comprises:
from about 45% to about 55% of water by weight of the emulsion;
from about 15% to about 24% of an oil component by weight of the emulsion;
from about 4% to about 7% of an emulsifier component by weight of the emulsion;
from about 20% to about 25% of a solvent component by weight of the emulsion;
from about 0.3% to about 0.5% of a stabilizing agent component by weight of the emulsion; and
from 0.5% to 1.5% of ruxolitinib, or a pharmaceutically acceptable salt thereof, by weight of the emulsion on a free base basis.

In some embodiments:
the oil component comprises one or more substances independently selected from petrolatums, fatty alcohols, mineral oils, triglycerides, and dimethicones;
the emulsifier component comprises one or more substances independently selected from glyceryl fatty esters and sorbitan fatty esters;
the solvent component comprises one or more substances independently selected from alkylene glycols and polyalkylene glycols; and
the stabilizing agent component comprises one or more substances independently selected from polysaccharides.

In some embodiments:
the oil component comprises one or more substances independently selected from white petrolatum, cetyl alcohol, stearyl alcohol, light mineral oil, medium chain triglycerides, and dimethicone;
the emulsifier component comprises one or more substances independently selected from glyceryl stearate and polysorbate 20;
the solvent component comprises one or more substances independently selected from propylene glycol and polyethylene glycol; and
the stabilizing agent component comprises xanthan gum.

In some embodiments, the emulsion further comprises:
from about 35% to about 65% of water by weight of the emulsion;
from about 2% to about 15% of an occlusive agent component by weight of the emulsion;
from about 2% to about 8% of a stiffening agent component by weight of the emulsion;
from about 5% to about 15% of an emollient component by weight of the emulsion;
from about 1% to about 9% of an emulsifier component by weight of the emulsion; and
from about 0.05% to about 5% of a stabilizing agent component by weight of the emulsion.
from about 10% to about 35% of a solvent component by weight of the emulsion; In some embodiments, the emulsion comprises:
from about 35% to about 65% of water by weight of the emulsion;
from about 2% to about 15% of an occlusive agent component by weight of the emulsion;
from about 2% to about 8% of a stiffening agent component by weight of the emulsion;
from about 5% to about 15% of an emollient component by weight of the emulsion;
from about 1% to about 9% of an emulsifier component by weight of the emulsion;
from about 0.05% to about 5% of a stabilizing agent component by weight of the emulsion;
from about 10% to about 35% of a solvent component by weight of the emulsion; and
from 0.5% to 1.5% of ruxolitinib, or a pharmaceutically acceptable salt thereof, by weight of the emulsion on a free base basis.

In some embodiments, the emulsion further comprises:
from about 40% to about 60% of water by weight of the emulsion;
from about 5% to about 10% of an occlusive agent component by weight of the emulsion;
from about 2% to about 8% of a stiffening agent component by weight of the emulsion;
from about 7% to about 12% of an emollient component by weight of the emulsion;
from about 2% to about 6% of an emulsifier component by weight of the emulsion;
from about 0.1% to about 2% of a stabilizing agent by weight of the emulsion; and
from about 15% to about 30% of a solvent component by weight of the emulsion.

In some embodiments, the emulsion comprises:
from about 40% to about 60% of water by weight of the emulsion;
from about 5% to about 10% of an occlusive agent component by weight of the emulsion;
from about 2% to about 8% of a stiffening agent component by weight of the emulsion;
from about 7% to about 12% of an emollient component by weight of the emulsion;
from about 2% to about 6% of an emulsifier component by weight of the emulsion;
from about 0.1% to about 2% of a stabilizing agent by weight of the emulsion;
from about 15% to about 30% of a solvent component by weight of the emulsion; and
from 0.5% to 1.5% of ruxolitinib, or a pharmaceutically acceptable salt thereof, by weight of the emulsion on a free base basis.

In some embodiments, the emulsion further comprises:
from about 45% to about 55% of water by weight of the emulsion;
from about 5% to about 10% of an occlusive agent component by weight of the emulsion;
from about 3% to about 6% of a stiffening agent component by weight of the emulsion;
from about 7% to about 13% of an emollient component by weight of the emulsion;
from about 3% to about 5% of an emulsifier component by weight of the emulsion;
from about 0.3% to about 0.5% of a stabilizing agent component by weight of the emulsion; and
from about 20% to about 25% of a solvent component by weight of the emulsion.

In some embodiments, the emulsion comprises:
from about 45% to about 55% of water by weight of the emulsion;
from about 5% to about 10% of an occlusive agent component by weight of the emulsion;
from about 3% to about 6% of a stiffening agent component by weight of the emulsion;
from about 7% to about 13% of an emollient component by weight of the emulsion;
from about 3% to about 5% of an emulsifier component by weight of the emulsion;
from about 0.3% to about 0.5% of a stabilizing agent component by weight of the emulsion;
from about 20% to about 25% of a solvent component by weight of the emulsion; and
from 0.5% to 1.5% of ruxolitinib, or a pharmaceutically acceptable salt thereof, by weight of the emulsion on a free base basis.

In some embodiments, the emulsion further comprises:
from about 45% to about 55% of water by weight of the emulsion;
from about 5% to about 10% of an occlusive agent component by weight of the emulsion;
from about 4% to about 7% of a stiffening agent component by weight of the emulsion;
from about 7% to about 13% of an emollient component by weight of the emulsion;
from about 4% to about 7% of an emulsifier component by weight of the emulsion;
from about 0.3% to about 0.5% of a stabilizing agent component by weight of the emulsion; and
from about 20% to about 25% of a solvent component by weight of the emulsion.

In some embodiments, the emulsion comprises:
from about 45% to about 55% of water by weight of the emulsion;
from about 5% to about 10% of an occlusive agent component by weight of the emulsion;
from about 4% to about 7% of a stiffening agent component by weight of the emulsion;

from about 7% to about 13% of an emollient component by weight of the emulsion;

from about 4% to about 7% of an emulsifier component by weight of the emulsion;

from about 0.3% to about 0.5% of a stabilizing agent component by weight of the emulsion;

from about 20% to about 25% of a solvent component by weight of the emulsion; and from 0.5% to 1.5% of ruxolitinib, or a pharmaceutically acceptable salt thereof, by weight of the emulsion on a free base basis.

In some embodiments, the emulsion further comprises:

from about 45% to about 55% of water by weight of the emulsion;

about 7% of an occlusive agent component by weight of the emulsion;

from about 4.5% to about 5% of a stiffening agent component by weight of the emulsion;

about 10% of an emollient component by weight of the emulsion;

from about 4% to about 4.5% of an emulsifier component by weight of the emulsion;

about 0.4% of a stabilizing agent component by weight of the emulsion; and about 22% of a solvent component by weight of the emulsion.

In some embodiments, the emulsion comprises:

from about 45% to about 55% of water by weight of the emulsion;

about 7% of an occlusive agent component by weight of the emulsion;

from about 4.5% to about 5% of a stiffening agent component by weight of the emulsion;

about 10% of an emollient component by weight of the emulsion;

from about 4% to about 4.5% of an emulsifier component by weight of the emulsion;

about 0.4% of a stabilizing agent component by weight of the emulsion;

about 22% of a solvent component by weight of the emulsion; and from 0.5% to 1.5% of ruxolitinib, or a pharmaceutically acceptable salt thereof, by weight of the emulsion on a free base basis.

In some embodiments, the ruxolitinib, or pharmaceutically acceptable salt thereof, is present as ruxolitinib phosphate.

In some embodiments, the emulsion comprises 1.5% of ruxolitinib, or a pharmaceutically acceptable salt thereof, by weight of the emulsion.

In some embodiments, the emulsion comprises 1.5% of ruxolitinib phosphate by weight of the emulsion.

In some embodiments, the emulsion comprises 1.1% of ruxolitinib, or a pharmaceutically acceptable salt thereof, by weight of the emulsion.

In some embodiments, the emulsion comprises 1.1% of ruxolitinib phosphate by weight of the emulsion.

In some embodiments, the emulsion comprises 0.75% of ruxolitinib, or a pharmaceutically acceptable salt thereof, by weight of the emulsion.

In some embodiments, the emulsion comprises 0.75% of ruxolitinib phosphate by weight of the emulsion.

In some embodiments, the combined amount of the stiffening agent component and the emulsifier component is at least about 8% by weight of the emulsion.

In some embodiments:
the occlusive agent component comprises a petrolatum;
the stiffening agent component comprises one or more substances independently selected from one or more fatty alcohols;
the emollient component comprises one or more substances independently selected from mineral oils and triglycerides;
the emulsifier component comprises one or more substances independently selected from glyceryl fatty esters and sorbitan fatty esters;
the stabilizing agent component comprises one or more substances independently selected from polysaccharides; and
the solvent component comprises one or more substances independently selected from alkylene glycols and polyalkylene glycols.

In some embodiments:
the occlusive agent component comprises white petrolatum;
the stiffening agent component comprises one or more substances independently selected from cetyl alcohol and stearyl alcohol;
the emollient component comprises one or more substances independently selected from light mineral oil, medium chain triglycerides, and dimethicone;
the emulsifier component comprises one or more substances independently selected from glyceryl stearate and polysorbate 20;
the stabilizing agent component comprises xanthan gum; and
the solvent component comprises one or more substances independently selected from propylene glycol and polyethylene glycol.

In some embodiments, the emulsion further comprises an antimicrobial preservative component.

In some embodiments, the antimicrobial preservative component is present in an amount of about 0.05% to about 3% by weight of the emulsion.

In some embodiments, the antimicrobial preservative component is present in an amount of about 0.1% to about 1% by weight of the emulsion.

In some embodiments, the antimicrobial preservative component comprises one or more substances independently selected from alkyl parabens and phenoxyethanol.

In some embodiments, the antimicrobial preservative component comprises one or more substances independently selected from methyl paraben, propyl paraben, and phenoxyethanol.

In some embodiments, the antimicrobial preservative component comprises methyl paraben and propyl paraben.

In some embodiments, the methylparaben is present in an amount of about 0.001% to about 5% by weight of the emulsion.

In some embodiments, the methylparaben is present in an amount of about 0.1% by weight of the emulsion.

In some embodiments, the propylparaben is present in an amount of about 0.001% to about 5% by weight of the emulsion.

In some embodiments, the propylparaben is present in an amount of about 0.05% by weight of the emulsion.

In some embodiments, the phenoxyethanol is present in an amount of about 0.1% to about 15% by weight of the emulsion.

In some embodiments, the phenoxyethanol is present in an amount of about 0.5% by weight of the emulsion.

In some embodiments, the phenoxyethanol is present in an amount of about 0.1% to about 10% by weight of the emulsion.

In some embodiments, the pH of the cream is adjusted to about 4.0, about 5.5, or about 7.0.

In some embodiments, the pH of the cream is adjusted to about 4.0, about 5.5, about 6.5, or about 7.0.

In some embodiments, the pH of the cream is adjusted to a range of about 6.5 to about 7.0.

In some embodiments, the pH of the cream is adjusted with trolamine and/or phosphoric acid. In some embodiments, the pH of the cream is adjusted with trolamine. In some embodiments, the pH of the cream is adjusted with phosphoric acid. In some embodiments, the pH of the cream is adjusted with trolamine and phosphoric acid.

In some embodiments, the emulsion further comprises an anti-oxidant.

In some embodiments, the anti-oxidant is butylated hydroxytoluene (BHT), butylated hydroxyanisole (BHA), or tocopherol, or a combination thereof.

In some embodiments, the emulsion further comprises a chelating agent component.

In some embodiments, the chelating agent component comprises edetate disodium.

In some embodiments, the edetate disodium is present in an amount of about 0.001% to about 5% by weight of the emulsion.

In some embodiments, the edetate disodium is present in an amount of about 0.001% to about 1% by weight of the emulsion.

In some embodiments, the emulsion further comprises a calcipotriol stabilizer.

In some embodiments, the calcipotriol stabilizer is ascorbyl palmitate, ascorbic acid, or citric acid, or a combination thereof.

In some embodiments, the emulsion further comprises a humectant.

In some embodiments, the humectant is glycerol.

In some embodiments, the glycerol is present in an amount of about 0.01% to about 20% by weight of the emulsion.

In some embodiments, the glycerol is present in an amount of about 0.1% to about 20% by weight of the emulsion.

In some embodiments, the emulsion further comprises a surfactant.

In some embodiments, the surfactant is polysorbate 80. In some embodiments, the surfactant is polysorbate 80 is present in an amount of about 0.01% to about 15% by weight of the emulsion. In some embodiments, the surfactant is polysorbate 80 is present in an amount of about 0.1% to about 15% by weight of the emulsion.

Ruxolitinib can be prepared as described in U.S. Pat. No. 7,598,257 and U.S. Patent Publ. No. 2009/0181959, each of which is incorporated herein by reference in its entirety. The 1:1 phosphate salt of ruxolitinib can be prepared as described in U.S. Patent Publ. No. 2008/0312259, which is incorporated herein by reference in its entirety.

As will be appreciated, some components of the cream (emulsion) described herein can possess multiple functions. For example, a given substance may act as both an emulsifying agent component and a stabilizing agent. In some such cases, the function of a given component can be considered singular, even though its properties may allow multiple functionality. In some embodiments, each component of the formulation comprises a different substance or mixture of substances.

Pharmaceutical Formulations (Fixed-Dose Combinations)

Pharmaceutical formulations provided and described herein may be used in the methods described in the present disclosure.

The concentrations of JAK inhibitors, vitamin D3, or Vitamin D3 analogs, or the pharmaceutically acceptable salts of any of the aforementioned, described supra, may also be used in the fixed-dose combination formulations described as follows. As used herein, "pharmaceutical formulation for topical treatment of a skin disease" and "topical formulation" are used interchangeably.

The present disclosure further provides a pharmaceutical formulation for topical treatment of a skin disease, comprising (a) a JAK inhibitor, or a pharmaceutically acceptable salt thereof, and (b) a vitamin D derivative, or a pharmaceutically acceptable salt thereof.

The present disclosure also provides a pharmaceutical formulation for topical treatment of a skin disease, comprising (a) ruxolitinib, or a pharmaceutically acceptable salt thereof, and (b) a vitamin D derivative, or a pharmaceutically acceptable salt thereof.

The present disclosure further provides a pharmaceutical formulation for topical treatment of a skin disease, comprising (a) ruxolitinib phosphate, or a pharmaceutically acceptable salt thereof, and (b) a vitamin D derivative, or a pharmaceutically acceptable salt thereof.

The present disclosure also provides a pharmaceutical formulation for topical treatment of a skin disease, comprising (a) a JAK inhibitor, or a pharmaceutically acceptable salt thereof, and (b) vitamin D3, a vitamin D3 analog, or a pharmaceutically acceptable salt thereof.

The present disclosure further provides a pharmaceutical formulation for topical treatment of a skin disease, comprising (a) ruxolitinib, or a pharmaceutically acceptable salt thereof, and (b) vitamin D3, a vitamin D3 analog, or a pharmaceutically acceptable salt thereof. In some embodiments, the ruxolitinib, or the pharmaceutically acceptable salt thereof, is present in an amount of about 0.05%, about 0.06%, about 0.07%, about 0.08%, about 0.09%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1.0%, about 1.05%, about 1.1%, about 1.15%, about 1.2%, about 1.25%, about 1.3%, about 1.35%, about 1.4%, about 1.45%, about 1.5%, about 1.55%, about 1.6%, about 1.65%, about 1.7%, about 1.75%, about 1.8%, about 1.85%, about 1.9%, about 1.95%, about 2.0%, about 2.5%, or about 3.0% by weight of the formulation on a free base basis.

The present disclosure also provides a pharmaceutical formulation for topical treatment of a skin disease, comprising (a) ruxolitinib phosphate, or a pharmaceutically acceptable salt thereof, and (b) vitamin D3, a vitamin D3 analog, or a pharmaceutically acceptable salt thereof. The present disclosure also provides a pharmaceutical formulation for topical treatment of a skin disease, comprising (a) from about 0.75% w/w to about 1.5% w/w of ruxolitinib, or a pharmaceutically acceptable salt thereof, on a free base basis, and (b) vitamin D3, a vitamin D3 analog, or a pharmaceutically acceptable salt thereof. In some embodiments, the ruxolitinib, or the pharmaceutically acceptable salt thereof, is ruxolitinib phosphate.

The present disclosure also provides a pharmaceutical formulation for topical treatment of a skin disease, comprising (a) about 0.75% w/w of ruxolitinib, or a pharmaceutically acceptable salt thereof, on a free base basis, and (b) vitamin D3, a vitamin D3 analog, or a pharmaceutically acceptable salt thereof. In some embodiments, the ruxolitinib, or the pharmaceutically acceptable salt thereof, is ruxolitinib phosphate.

The present disclosure also provides a pharmaceutical formulation for topical treatment of a skin disease, comprising (a) about 1.5% w/w of ruxolitinib, or a pharmaceutically acceptable salt thereof, on a free base basis, and (b) vitamin D3, a vitamin D3 analog, or a pharmaceutically acceptable salt thereof. In some embodiments, the ruxolitinib, or the pharmaceutically acceptable salt thereof, is ruxolitinib phosphate.

The present disclosure also provides a pharmaceutical formulation for topical treatment of a skin disease, comprising (a) about 1.1% w/w of ruxolitinib, or a pharmaceutically acceptable salt thereof, on a free base basis, and (b) vitamin D3, a vitamin D3 analog, or a pharmaceutically acceptable salt thereof. In some embodiments, the ruxolitinib, or the pharmaceutically acceptable salt thereof, is ruxolitinib phosphate.

The present disclosure also provides a pharmaceutical formulation for topical treatment of a skin disease, comprising (a) from about 0.75% w/w to about 1.5% w/w of ruxolitinib, or a pharmaceutically acceptable salt thereof, on a free base basis, and (b) from about 1 µg/mL to about 50 µg/mL of vitamin D3, a vitamin D3 analog, or a pharmaceutically acceptable salt thereof, on a free base basis. In some embodiments, the ruxolitinib, or the pharmaceutically acceptable salt thereof, is ruxolitinib phosphate.

The present disclosure also provides a pharmaceutical formulation for topical treatment of a skin disease, comprising (a) about 0.75% w/w of ruxolitinib, or a pharmaceutically acceptable salt thereof, on a free base basis, and (b) from about 1 µg/mL to about 50 µg/mL of vitamin D3, a vitamin D3 analog, or a pharmaceutically acceptable salt thereof, on a free base basis. In some embodiments, the ruxolitinib, or the pharmaceutically acceptable salt thereof, is ruxolitinib phosphate.

The present disclosure also provides a pharmaceutical formulation for topical treatment of a skin disease, comprising (a) about 1.5% w/w of ruxolitinib, or a pharmaceutically acceptable salt thereof, on a free base basis, and (b) from about 1 µg/mL to about 50 µg/mL of vitamin D3, a vitamin D3 analog, or a pharmaceutically acceptable salt thereof, on a free base basis. In some embodiments, the ruxolitinib, or the pharmaceutically acceptable salt thereof, is ruxolitinib phosphate.

The present disclosure also provides a pharmaceutical formulation for topical treatment of a skin disease, comprising (a) about 1.1% w/w of ruxolitinib, or a pharmaceutically acceptable salt thereof, on a free base basis, and (b) from about 1 µg/mL to about 50 µg/mL of vitamin D3, a vitamin D3 analog, or a pharmaceutically acceptable salt thereof, on a free base basis. In some embodiments, the ruxolitinib, or the pharmaceutically acceptable salt thereof, is ruxolitinib phosphate.

The present disclosure also provides a pharmaceutical formulation for topical treatment of a skin disease, comprising (a) from about 0.75% w/w to about 1.5% w/w of ruxolitinib, or a pharmaceutically acceptable salt thereof, on a free base basis, and (b) about 1 µg/mL of vitamin D3, a vitamin D3 analog, or a pharmaceutically acceptable salt thereof, on a free base basis. In some embodiments, the ruxolitinib, or the pharmaceutically acceptable salt thereof, is ruxolitinib phosphate.

The present disclosure also provides a pharmaceutical formulation for topical treatment of a skin disease, comprising (a) from about 0.75% w/w to about 1.5% w/w of ruxolitinib, or a pharmaceutically acceptable salt thereof, on a free base basis, and (b) about 10 µg/mL of vitamin D3, a vitamin D3 analog, or a pharmaceutically acceptable salt thereof, on a free base basis. In some embodiments, the ruxolitinib, or the pharmaceutically acceptable salt thereof, is ruxolitinib phosphate.

The present disclosure also provides a pharmaceutical formulation for topical treatment of a skin disease, comprising (a) from about 0.75% w/w to about 1.5% w/w of ruxolitinib, or a pharmaceutically acceptable salt thereof, on a free base basis, and (b) about 50 µg/mL of vitamin D3, a vitamin D3 analog, or a pharmaceutically acceptable salt thereof, on a free base basis. In some embodiments, the ruxolitinib, or the pharmaceutically acceptable salt thereof, is ruxolitinib phosphate.

The present disclosure also provides a pharmaceutical formulation for topical treatment of a skin disease, comprising (a) about 0.75% w/w of ruxolitinib, or a pharmaceutically acceptable salt thereof, on a free base basis, and (b) about 1 µg/mL of vitamin D3, a vitamin D3 analog, or a pharmaceutically acceptable salt thereof, on a free base basis. In some embodiments, the ruxolitinib, or the pharmaceutically acceptable salt thereof, is ruxolitinib phosphate.

The present disclosure also provides a pharmaceutical formulation for topical treatment of a skin disease, comprising (a) about 0.75% w/w of ruxolitinib, or a pharmaceutically acceptable salt thereof, on a free base basis, and (b) about 10 µg/mL of vitamin D3, a vitamin D3 analog, or a pharmaceutically acceptable salt thereof, on a free base basis. In some embodiments, the ruxolitinib, or the pharmaceutically acceptable salt thereof, is ruxolitinib phosphate.

The present disclosure also provides a pharmaceutical formulation for topical treatment of a skin disease, comprising (a) about 0.75% w/w of ruxolitinib, or a pharmaceutically acceptable salt thereof, on a free base basis, and (b) about 50 µg/mL of vitamin D3, a vitamin D3 analog, or a pharmaceutically acceptable salt thereof, on a free base basis. In some embodiments, the ruxolitinib, or the pharmaceutically acceptable salt thereof, is ruxolitinib phosphate.

The present disclosure also provides a pharmaceutical formulation for topical treatment of a skin disease, comprising (a) about 1.5% w/w of ruxolitinib, or a pharmaceutically acceptable salt thereof, on a free base basis, and (b) about 1 µg/mL of vitamin D3, a vitamin D3 analog, or a pharmaceutically acceptable salt thereof, on a free base basis. In some embodiments, the ruxolitinib, or the pharmaceutically acceptable salt thereof, is ruxolitinib phosphate.

The present disclosure also provides a pharmaceutical formulation for topical treatment of a skin disease, comprising (a) about 1.1% w/w of ruxolitinib, or a pharmaceutically acceptable salt thereof, on a free base basis, and (b) about 1 µg/mL of vitamin D3, a vitamin D3 analog, or a pharmaceutically acceptable salt thereof, on a free base basis. In some embodiments, the ruxolitinib, or the pharmaceutically acceptable salt thereof, is ruxolitinib phosphate.

The present disclosure also provides a pharmaceutical formulation for topical treatment of a skin disease, comprising (a) about 1.5% w/w of ruxolitinib, or a pharmaceutically acceptable salt thereof, on a free base basis, and (b) about 10 µg/mL of vitamin D3, a vitamin D3 analog, or a pharmaceutically acceptable salt thereof, on a free base basis. In some embodiments, the ruxolitinib, or the pharmaceutically acceptable salt thereof, is ruxolitinib phosphate.

The present disclosure also provides a pharmaceutical formulation for topical treatment of a skin disease, comprising (a) about 1.1% w/w of ruxolitinib, or a pharmaceutically acceptable salt thereof, on a free base basis, and (b) about 10

µg/mL of vitamin D3, a vitamin D3 analog, or a pharmaceutically acceptable salt thereof, on a free base basis. In some embodiments, the ruxolitinib, or the pharmaceutically acceptable salt thereof, is ruxolitinib phosphate.

The present disclosure also provides a pharmaceutical formulation for topical treatment of a skin disease, comprising (a) about 1.5% w/w of ruxolitinib, or a pharmaceutically acceptable salt thereof, on a free base basis, and (b) about 50 µg/mL of vitamin D3, a vitamin D3 analog, or a pharmaceutically acceptable salt thereof, on a free base basis. In some embodiments, the ruxolitinib, or the pharmaceutically acceptable salt thereof, is ruxolitinib phosphate. The present disclosure also provides a pharmaceutical formulation for topical treatment of a skin disease, comprising (a) from about 0.75% w/w to about 1.5% w/w of ruxolitinib, or a pharmaceutically acceptable salt thereof, on a free base basis, and (b) from about 0.0001% w/w to about 0.01% w/w of vitamin D3, a vitamin D3 analog, or a pharmaceutically acceptable salt thereof, on a free base basis.

The present disclosure also provides a pharmaceutical formulation for topical treatment of a skin disease, comprising (a) from about 0.75% w/w to about 1.5% w/w of ruxolitinib, or a pharmaceutically acceptable salt thereof, on a free base basis, and (b) from about 0.0001% w/w to about 0.005% w/w of vitamin D3, a vitamin D3 analog, or a pharmaceutically acceptable salt thereof, on a free base basis. In some embodiments, the ruxolitinib, or the pharmaceutically acceptable salt thereof, is ruxolitinib phosphate.

The present disclosure also provides a pharmaceutical formulation for topical treatment of a skin disease, comprising (a) about 1.5% w/w of ruxolitinib, or a pharmaceutically acceptable salt thereof, on a free base basis, and (b) from about 0.0001% w/w to about 0.005% w/w of vitamin D3, a vitamin D3 analog, or a pharmaceutically acceptable salt thereof, on a free base basis. In some embodiments, the ruxolitinib, or the pharmaceutically acceptable salt thereof, is ruxolitinib phosphate.

The present disclosure also provides a pharmaceutical formulation for topical treatment of a skin disease, comprising (a) about 1.1% w/w of ruxolitinib, or a pharmaceutically acceptable salt thereof, on a free base basis, and (b) from about 0.0001% w/w to about 0.005% w/w of vitamin D3, a vitamin D3 analog, or a pharmaceutically acceptable salt thereof, on a free base basis. In some embodiments, the ruxolitinib, or the pharmaceutically acceptable salt thereof, is ruxolitinib phosphate.

The present disclosure also provides a pharmaceutical formulation for topical treatment of a skin disease, comprising (a) about 0.75% w/w of ruxolitinib, or a pharmaceutically acceptable salt thereof, on a free base basis, and (b) from about 0.0001% w/w to about 0.005% w/w of vitamin D3, a vitamin D3 analog, or a pharmaceutically acceptable salt thereof, on a free base basis. In some embodiments, the ruxolitinib, or the pharmaceutically acceptable salt thereof, is ruxolitinib phosphate.

The present disclosure also provides a pharmaceutical formulation for topical treatment of a skin disease, comprising (a) from about 0.75% w/w to about 1.5% w/w of ruxolitinib, or a pharmaceutically acceptable salt thereof, on a free base basis, and (b) about 0.005% w/w of vitamin D3, a vitamin D3 analog, or a pharmaceutically acceptable salt thereof, on a free base basis.

The present disclosure also provides a pharmaceutical formulation for topical treatment of a skin disease, comprising (a) about 0.75% w/w of ruxolitinib, or a pharmaceutically acceptable salt thereof, on a free base basis, and (b) about 0.005% w/w of vitamin D3, a vitamin D3 analog, or a pharmaceutically acceptable salt thereof, on a free base basis. In some embodiments, the ruxolitinib, or the pharmaceutically acceptable salt thereof, is ruxolitinib phosphate.

The present disclosure also provides a pharmaceutical formulation for topical treatment of a skin disease, comprising (a) about 1.5% w/w of ruxolitinib, or a pharmaceutically acceptable salt thereof, on a free base basis, and (b) about 0.005% w/w of vitamin D3, a vitamin D3 analog, or a pharmaceutically acceptable salt thereof, on a free base basis. In some embodiments, the ruxolitinib, or the pharmaceutically acceptable salt thereof, is ruxolitinib phosphate.

The present disclosure also provides a pharmaceutical formulation for topical treatment of a skin disease, comprising (a) about 1.1% w/w of ruxolitinib, or a pharmaceutically acceptable salt thereof, on a free base basis, and (b) about 0.005% w/w of vitamin D3, a vitamin D3 analog, or a pharmaceutically acceptable salt thereof, on a free base basis. In some embodiments, the ruxolitinib, or the pharmaceutically acceptable salt thereof, is ruxolitinib phosphate.

The formulations described in the preceding paragraphs, wherein the vitamin D3, the vitamin D3 analog, or the pharmaceutically acceptable salt thereof, is a vitamin D3 analog, or a pharmaceutically acceptable salt thereof. In some embodiments, the vitamin D3 analog, or a pharmaceutically acceptable salt thereof, is selected from calcidiol, calcitriol, calcipotriol, alfacalcidol, tacalcitol, maxacalcitol, falecalcitriol, eldecalcitol, inecalcitol, seocalcitol, lexicalcitol, 20-epi-1α,25(OH)$_2$D$_3$, CD578 (17-methyl-19-nor-21-nor-23-yne-26,27-F6-1α,25(OH)$_{2D3}$), TX527 (19-nor-14,20-bisepi-23-yne-1α,25(OH)$_2$D$_3$), 2MD (2-methylene-19-nor-(20S)-1α,25(OH)$_2$D$_3$), PRI-2205 ((5E,7E)-22-ene-26,27-dehydro-1α,25(OH)$_2$D$_3$), ILX23-7553 (16-ene-23-yne-1α,25(OH)$_2$D$_3$), and MART-10(19-nor-2α-(3-hydroxypropyl)-1α,25(OH)$_2$D$_3$). In some embodiments, the vitamin D3 analog, or a pharmaceutically acceptable salt thereof, is calcipotriol. In some embodiments, the vitamin D3 analog, or a pharmaceutically acceptable salt thereof, is tacalcitol. In some embodiments, the vitamin D3 analog, or a pharmaceutically acceptable salt thereof, is maxacalcitol.

The present disclosure also provides a pharmaceutical formulation for topical treatment of a skin disease, comprising (a) from about 0.75% w/w to about 1.5% w/w of ruxolitinib, or a pharmaceutically acceptable salt thereof, on a free base basis, and (b) about 0.005% w/w of calcipotriol. In some embodiments, the ruxolitinib, or the pharmaceutically acceptable salt thereof, is ruxolitinib phosphate.

The present disclosure also provides a pharmaceutical formulation for topical treatment of a skin disease, comprising (a) about 0.75% w/w of ruxolitinib, or a pharmaceutically acceptable salt thereof, on a free base basis, and (b) about 0.005% w/w of calcipotriol. In some embodiments, the ruxolitinib, or the pharmaceutically acceptable salt thereof, is ruxolitinib phosphate.

The present disclosure also provides a pharmaceutical formulation for topical treatment of a skin disease, comprising (a) about 1.5% w/w of ruxolitinib, or a pharmaceutically acceptable salt thereof, on a free base basis, and (b) about 0.005% w/w of calcipotriol. In some embodiments, the ruxolitinib, or the pharmaceutically acceptable salt thereof, is ruxolitinib phosphate.

The present disclosure also provides a pharmaceutical formulation for topical treatment of a skin disease, comprising (a) about 1.1% w/w of ruxolitinib, or a pharmaceutically acceptable salt thereof, on a free base basis, and (b) about 0.005% w/w of calcipotriol. In some embodiments, the ruxolitinib, or the pharmaceutically acceptable salt thereof, is ruxolitinib phosphate.

In some embodiments, the pharmaceutical formulations described herein are creams. In some embodiments, the cream formulations of ruxolitinib described supra, may also be used in the fixed-dose combination formulations described as follows.

In some embodiments, the pharmaceutical formulations described herein are lotions.

In some embodiments, the pharmaceutical formulations described herein further comprise water. In some embodiments, the water comprises from about 5% to about 90% by weight of the pharmaceutical formulation. In some embodiments, the water comprises from about 10% to about 80% by weight of the pharmaceutical formulation. In some embodiments, the water comprises from about 10% to about 70% by weight of the pharmaceutical formulation. In some embodiments, the water comprises from about 10% to about 60% by weight of the pharmaceutical formulation. In some embodiments, the water comprises from about 20% to about 70% by weight of the pharmaceutical formulation. In some embodiments, the water comprises from about 20% to about 60% by weight of the pharmaceutical formulation. In some embodiments, the water comprises from about 20% to about 50% by weight of the pharmaceutical formulation. In some embodiments, the water comprises from about 5% to about 90%, from about 10% to about 80%, from about 10% to about 70%, from about 10% to about 60%, about 20% to about 70%, about 20% to about 60%, or from about 20% to about 50% by weight of the pharmaceutical formulation.

In some embodiments, the pharmaceutical formulations described herein have a pH of not more than about 3.6. In some embodiments, the pharmaceutical formulations described herein have a pH of from about 2.7 to about 3.9. In some embodiments, the pharmaceutical formulations described herein have a pH of from about 2.7 to about 3.6. In some embodiments, the pharmaceutical formulations described herein have a pH of from about 4 to about 8. In some embodiments, the pharmaceutical formulations described herein have a pH of from about 6.0 to about 7.0. In some embodiments, the pharmaceutical formulations described herein have a pH of from about 6.5 to about 7.0. In some embodiments, the pharmaceutical formulations described herein have a pH of from about 6.5 to about 7.5.

In some embodiments, the pharmaceutical formulations described herein are oil-in-water emulsions.

In some embodiments, the oil-in-water emulsion comprises water, an oil component, and an emulsifier or stabilizer component. In some embodiments, the oil-in-water emulsion comprises water, an oil component, and an emulsifier component.

In some embodiments, the water comprises from about 5% to about 90% by weight of the pharmaceutical formulation. In some embodiments, the water comprises from about 10% to about 80% by weight of the pharmaceutical formulation. In some embodiments, the water comprises from about 10% to about 70% by weight of the pharmaceutical formulation. In some embodiments, the water comprises from about 10% to about 60% by weight of the pharmaceutical formulation. In some embodiments, the water comprises from about 20% to about 70% by weight of the pharmaceutical formulation. In some embodiments, the water comprises from about 20% to about 60% by weight of the pharmaceutical formulation. In some embodiments, the water comprises from about 20% to about 50% by weight of the pharmaceutical formulation. In some embodiments, the water comprises from about 5% to about 90%, from about 10% to about 80%, from about 10% to about 70%, from about 10% to about 60%, about 20% to about 70%, about 20% to about 60%, or from about 20% to about 50% by weight of the pharmaceutical formulation.

In some embodiments, the oil component comprises from about 5% to about 90% by weight of the pharmaceutical formulation. In some embodiments, the oil component comprises from about 5% to about 80% by weight of the pharmaceutical formulation. In some embodiments, the oil component comprises from about 5% to about 70% by weight of the pharmaceutical formulation. In some embodiments, the oil component comprises from about 5% to about 60% by weight of the pharmaceutical formulation. In some embodiments, the oil component comprises from about 5% to about 50% by weight of the pharmaceutical formulation. In some embodiments, the oil component comprises from about 5% to about 40% by weight of the pharmaceutical formulation. In some embodiments, the oil component comprises from about 5% to about 30% by weight of the pharmaceutical formulation. In some embodiments, the oil component comprises from about 5% to about 20% by weight of the pharmaceutical formulation. In some embodiments, the oil component comprises from about 5% to about 90%, from about 5% to about 80%, from about 5% to about 70%, from about 5% to about 60%, from about 5% to about 50%, or from about 5% to about 40% by weight of the pharmaceutical formulation. In some embodiments, the oil component comprises a fatty alcohol, a nut oil and/or a mineral oil. In some embodiments, the oil component comprises one of the oil components described herein, including emollients, stiffening agents or other oil components.

In some embodiments, the emulsifier or stabilizer component comprises from about 1% to about 30% by weight of the pharmaceutical formulation. In some embodiments, the emulsifier or stabilizer component comprises from about 5% to about 25% by weight of the pharmaceutical formulation. In some embodiments, the emulsifier or stabilizer component comprises from about 1% to about 30% by weight of the pharmaceutical formulation. In some embodiments, the emulsifier or stabilizer component comprises from about 1% to about 30% or from about 5% to about 25% by weight of the pharmaceutical formulation. In some embodiments, the emulsifier component comprises a non-ionic surfactant. In some embodiments, the emulsifier or stabilizer component comprises a polysorbate, a poloxamer, a fatty alcohol, a polyethylene glycol fatty ether, glyceryl fatty esters, and/or a polyethylene glycol fatty ester. In some embodiments, the emulsifier or stabilizer component comprises one of the emulsifier, stabilizer, or surfactants described herein.

In some embodiments, the emulsifier or stabilizer component comprises a non-ionic surfactant. In some embodiments, the non-ionic surfactant is cetomacrogol 1000 or poloxamer 407.

In some embodiment, the pharmaceutical formulation further comprises a solvent component for dissolving ruxolitinib, or a pharmaceutically acceptable salt thereof. In some embodiment, the solvent component comprises from about 1% to about 40% by weight of the pharmaceutical formulation. In some embodiment, the solvent component comprises from about 2% to about 30% by weight of the pharmaceutical formulation. In some embodiment, the solvent component comprises from about 5% to about 30% by weight of the pharmaceutical formulation. In some embodiment, the solvent component comprises from about 5% to about 25% by weight of the pharmaceutical formulation. In some embodiment, the solvent component comprises from about 5% to about 20% by weight of the pharmaceutical formulation. In some embodiment, the solvent component comprises from about 10% to about 20% by weight of the pharmaceutical formulation. In some embodiment, the solvent component comprises from about 5% to about 20%, from about 2% to about 30%, from about 5% to about 30%, from about 5% to about 25%, from about 5% to about 20%, or from about 10% to about 20% by weight of the pharmaceutical formulation. In some embodiments, the solvent component comprises diethylene glycol monoethyl ether, such as Transcutol® P. In some embodiments, the solvent component comprises one of the solvent components described herein. In some embodiments, the propylene glycol is present of about 6.5% by weight of the emulsion. In some embodiments, the solvent component comprises diethylene glycol monoethyl ether, such as Transcutol® P. In some embodiments, the diethylene glycol monoethyl ether is present in an amount of about 0.1% to about 30% w/w by weight of the emulsion. In some embodiments, the diethylene glycol monoethyl ether is present in an amount of about 0.1% to about 20% w/w by weight of the emulsion.

In some embodiments, the pharmaceutical formulations further comprise an antioxidant. In some embodiments, the anti-oxidant is butylated hydroxytoluene (BHT), butylated hydroxyanisole (BHA), or tocopherol, or a combination thereof. In some embodiments, the antioxidant comprises from about 0.01% to about 10%, from about 0.01% to about 5%, from about 0.01% to about 2%, from about 0.01% to about 1%, or from about 0.1% to about 10% by weight of the pharmaceutical formulation.

In some embodiments, the pH is adjusted to about 6.0 to about 7.0, about 6.5 to about 7.0. In some embodiments, the pH is adjusted with trolamine.

In some embodiments, the oil component is present in an amount of about 10% to about 40% by weight of the emulsion.

In some embodiments, the oil component is present in an amount of about 15% to about 30% by weight of the emulsion.

In some embodiments, the oil component is present in an amount of about 20% to about 28% by weight of the emulsion.

In some embodiments, the oil component comprises one or more substances independently selected from petrolatums, fatty alcohols, mineral oils, triglycerides, and silicone oils.

In some embodiments, the oil component comprises one or more substances independently selected from white petrolatum, cetyl alcohol, stearyl alcohol, light mineral oil, medium chain triglycerides, and dimethicone.

In some embodiments, the oil component comprises an occlusive agent component.

In some embodiments, the occlusive agent is present in an amount of about 0.1% to about 15% by weight of the emulsion.

In some embodiments, the occlusive agent component is present in an amount of about 2% to about 15% by weight of the emulsion.

In some embodiments, the occlusive agent component is present in an amount of about 5% to about 10% by weight of the emulsion.

In some embodiments, the occlusive agent component comprises one or more substances selected from fatty acids (e.g., lanolin acid), fatty alcohols (e.g., lanolin alcohol), hydrocarbon oils & waxes (e.g., petrolatum), polyhydric alcohols (e.g., propylene glycol), silicones (e.g., dimethicone), sterols (e.g., cholesterol), vegetable or animal fat (e.g., cocoa butter), vegetable wax (e.g., Carnauba wax), and wax ester (e.g., bees wax).

In some embodiments, the occlusive agent component comprises one or more substances selected from lanolin acid fatty alcohols, lanolin alcohol, petrolatum, propylene glycol, dimethicone, cholesterol, cocoa butter, Carnauba wax, and bees wax.

In some embodiments, the occlusive agent component comprises petrolatum.

In some embodiments, the occlusive agent component comprises white petrolatum.

In some embodiments, the white petrolatum is present in an amount of about 7% by weight of the emulsion.

In some embodiments, the oil component comprises a stiffening agent component.

In some embodiments, the stiffening agent component is present in an amount of about 0.1% to about 15% by weight of the emulsion.

In some embodiments, the stiffening agent component is present in an amount of about 2% to about 8% by weight of the emulsion.

In some embodiments, the stiffening agent component is present in an amount of about 3% to about 6% by weight of the emulsion.

In some embodiments, the stiffening agent component comprises one or more substances independently selected from fatty alcohols.

In some embodiments, the stiffening agent component comprises one or more substances independently selected from C12-20 fatty alcohols.

In some embodiments, the stiffening agent component comprises one or more substances independently selected from C16-18 fatty alcohols.

In some embodiments, the stiffening agent component comprises one or more substances independently selected from cetyl alcohol and stearyl alcohol.

In some embodiments, the cetyl alcohol is present in an amount of about 0.1% to about 15% by weight of the emulsion.

In some embodiments, the cetyl alcohol in an amount of about 3% by weight of the emulsion.

In some embodiments, the stearyl alcohol is present in an amount of about 0.1% to about 15% by weight of the emulsion.

In some embodiments, the stearyl alcohol is present in an amount of about 1.75% by weight of the emulsion.

In some embodiments, the oil component comprises an emollient component.

In some embodiments, the emollient component is present in an amount of about 0.1% to about 20% by weight of the emulsion.

In some embodiments, the emollient component is present in an amount of about 5% to about 20% by weight of the emulsion.

In some embodiments, the emollient component is present in an amount of about 10% to about 15% by weight of the emulsion.

In some embodiments, the emollient component comprises one or more substances independently selected from mineral oils, triglycerides, and silicone oils.

In some embodiments, the emollient component comprises one or more substances independently selected from light mineral oil, medium chain triglycerides, and dimethicone.

In some embodiments, the light mineral oil is present in an amount of about 0.1% to about 15% by weight of the emulsion.

In some embodiments, the light mineral oil is present in an amount of about 4% by weight of the emulsion.

In some embodiments, the dimethicone is present in an amount of about 1% by weight of the emulsion.

In some embodiments, the medium chain triglycerides are in an amount of about 7% by weight of the emulsion.

In some embodiments, the medium chain triglycerides are in an amount of about 10% by weight of the emulsion.

In some embodiments, the emollient component comprises one or more substances independently selected from mineral oils, triglycerides, silicone oils, and nut oils.

In some embodiments, the nut oil is an almond oil. In some embodiments, the almond oil is a sweet almond oil. In some embodiments, the sweet almond oil is present in an amount of about 0.1% to about 15% by weight of the emulsion. In some embodiments, the sweet almond oil is present in an amount of about 0.1% to about 10% by weight of the emulsion.

In some embodiments, the water is present in an amount of about 20% to about 80% by weight of the emulsion.

In some embodiments, the water is present in an amount of about 35% to about 65% by weight of the emulsion.

In some embodiments, the water is present in an amount of about 45% to about 65% by weight of the emulsion.

In some embodiments, the emulsifier component is present in an amount of about 0.5% to about 15% by weight of the emulsion.

In some embodiments, the emulsifier component is present in an amount of about 1% to about 10% by weight of the emulsion.

In some embodiments, the emulsifier component is present in an amount of about 2% to about 6% by weight of the emulsion.

In some embodiments, the emulsifier component is present in an amount of about 3% to about 5% by weight of the emulsion.

In some embodiments, the emulsion comprises an emulsifier component and a stiffening agent component, wherein the combined amount of emulsifier component and stiffening agent component is at least about 8% by weight of the emulsion.

In some embodiments, the emulsifier component comprises one or more non-ionic emulsifiers.

In some embodiments, the emulsifier component comprises one or more substances independently selected from glyceryl fatty esters and sorbitan fatty esters.

In some embodiments, the emulsifier component comprises one or more substances independently selected from glyceryl stearate, and polysorbate 20.

In some embodiments, the glyceryl stearate is present in an amount of about 3% by weight of the emulsion.

In some embodiments, the polysorbate 20 is present in an amount of about 1.25% by weight of the emulsion.

In some embodiments, the emulsion further comprises a stabilizing agent component.

In some embodiments, the stabilizing agent component is present in an amount of about 0.05% to about 5% by weight of the emulsion.

In some embodiments, the stabilizing agent component is present in an amount of about 0.1% to about 2% by weight of the emulsion.

In some embodiments, the stabilizing agent component is present in an amount of about 0.3% to about 0.5% by weight of the emulsion.

In some embodiments, the stabilizing agent component comprises one or more substances independently selected from polysaccharides.

In some embodiments, the stabilizing agent component comprises xanthan gum.

In some embodiments, the emulsion further comprises a solvent component. In some embodiments, the solvent component is a solvent for the JAK inhibitor (e.g., ruxolitinib), or the pharmaceutically acceptable salt thereof.

In some embodiments, the solvent component is present in an amount of about 1% to about 35% by weight of the emulsion.

In some embodiments, the solvent component is present in an amount of about 5% to about 25% by weight of the emulsion.

In some embodiments, the solvent component is present in an amount of about 10% to about 20% by weight of the emulsion.

In some embodiments, the solvent component comprises one or more substances independently selected from alkylene glycols and polyalkylene glycols.

In some embodiments, the solvent component comprises one or more substances independently selected from propylene glycol and polyethylene glycol.

In some embodiments, the solvent component comprises one or more substances independently selected from PEG200, PEG300, PEG400, and propylene glycol In some embodiments, the solvent component comprises PEG300 and propylene glycol.

In some embodiments, the PEG300 is present in an amount of about 7% by weight of the emulsion.

In some embodiments, the solvent is a combination of PEG400 and propylene glycol.

In some embodiments, the PEG400 is present in an amount of about 7% by weight of the emulsion.

In some embodiments, the propylene glycol is present of about 6.5% by weight of the emulsion.

In some embodiments, the oil-in-water emulsion further comprises:
  from about 20% to about 80% of water by weight of the emulsion;
  from about 10% to about 40% of an oil component by weight of the emulsion;
  from about 1% to about 10% of an emulsifier component by weight of the emulsion;
  from about 1% to about 35% of a solvent component by weight of the emulsion; and
  from about 0.05% to about 5% of a stabilizing agent component by weight of the emulsion.

In some embodiments, the oil-in-water emulsion further comprises:
  from about 35% to about 65% of water by weight of the emulsion;
  from about 15% to about 35% of an oil component by weight of the emulsion;
  from about 2% to about 6% of an emulsifier component by weight of the emulsion;
  from about 5% to about 25% of a solvent component by weight of the emulsion; and
  from about 0.05% to about 5% of a stabilizing agent component by weight of the emulsion.

In some embodiments, the oil-in-water emulsion further comprises:
  from about 40% to about 65% of water by weight of the emulsion;
  from about 20% to about 28% of an oil component by weight of the emulsion;
  from about 3% to about 5% of an emulsifier component by weight of the emulsion;
  from about 10% to about 20% of a solvent component by weight of the emulsion; and from about 0.1% to about 2% of a stabilizing agent component by weight of the emulsion.

In some embodiments, the oil-in-water emulsion further comprises:
from about 40% to about 65% of water by weight of the emulsion;
from about 20% to about 28% of an oil component by weight of the emulsion;
from about 3% to about 5% of an emulsifier component by weight of the emulsion;
from about 10% to about 20% of a solvent component by weight of the emulsion; and
from about 0.3% to about 0.5% of a stabilizing agent component by weight of the emulsion.

In some embodiments, the pharmaceutical formulations described herein are oil-in-water emulsions comprising the oil-in-water emulsion comprises water, an oil component, and an emulsifier component, wherein:
the oil component comprises one or more substances independently selected from petrolatums, fatty alcohols, mineral oils, triglycerides, and dimethicones;
the emulsifier component comprises one or more substances independently selected from glyceryl fatty esters and sorbitan fatty esters;
the solvent component comprises one or more substances independently selected from alkylene glycols and polyalkylene glycols; and
the stabilizing agent component comprises one or more substances independently selected from polysaccharides.

In some embodiments, the pharmaceutical formulations described herein are oil-in-water emulsions comprising the oil-in-water emulsion comprises water, an oil component, and an emulsifier component, wherein:
the oil component comprises one or more substances independently selected from white petrolatum, cetyl alcohol, stearyl alcohol, light mineral oil, medium chain triglycerides, and dimethicone;
the emulsifier component comprises one or more substances independently selected from glyceryl stearate and polysorbate 20;
the solvent component comprises one or more substances independently selected from propylene glycol and polyethylene glycol; and
the stabilizing agent component comprises xanthan gum.

In some embodiments, the emulsion further comprises an antimicrobial preservative component.

In some embodiments, the antimicrobial preservative component is present in an amount of about 0.05% to about 3% by weight of the emulsion.

In some embodiments, the antimicrobial preservative component is present in an amount of about 0.1% to about 1% by weight of the emulsion.

In some embodiments, the antimicrobial preservative component comprises one or more substances independently selected from alkyl parabens and phenoxyethanol.

In some embodiments, the antimicrobial preservative component comprises one or more substances independently selected from methyl paraben, propyl paraben, and phenoxyethanol.

In some embodiments, the antimicrobial preservative component comprises methyl paraben and propyl paraben.

In some embodiments, the methylparaben is present in an amount of about 0.001% to about 5% by weight of the emulsion.

In some embodiments, the methylparaben is present in an amount of about 0.1% by weight of the emulsion.

In some embodiments, the propylparaben is present in an amount of about 0.001% to about 5% by weight of the emulsion.

In some embodiments, the propylparaben is present in an amount of about 0.05% by weight of the emulsion.

In some embodiments, the phenoxyethanol is present in an amount of about 0.1% to about 15% by weight of the emulsion.

In some embodiments, the phenoxyethanol is present in an amount of about 0.5% by weight of the emulsion.

In some embodiments, the pH of the cream is from about 4 to about 8.

In some embodiments, the pH of the cream is from about 6.5 to about 7.0.

In some embodiments, the emulsion further comprises an antioxidant.

In some embodiments, the anti-oxidant is butylated hydroxytoluene (BHT), butylated hydroxyanisole (BHA), or tocopherol, or a combination thereof.

In some embodiments, butylated hydroxytoluene is present in an amount of about 0.01% to about 15% w/w by weight of the emulsion. In some embodiments, the butylated hydroxytoluene is present in an amount of about 0.1% to about 10% by weight of the emulsion. In some embodiments, the butylated hydroxytoluene is present in an amount of about 0.1% to about 5% by weight of the emulsion.

In some embodiments, butylhydroxyanisole is present in an amount of about 0.001% to about 5% w/w by weight of the emulsion. In some embodiments, the butylhydroxyanisole is present in an amount of about 0.01% to about 1% by weight of the emulsion.

In some embodiments, the emulsion further comprises a calcipotriol stabilizer.

In some embodiments, the calcipotriol stabilizer is ascorbyl palmitate, ascorbic acid, fumaric acid, or citric acid, or a combination thereof.

In some embodiments, the present disclosure also provides a pharmaceutical formulation for topical treatment of a skin disease (or, alternatively, a method of any one of embodiments 1-75), wherein the formulation is an oil-in-water emulsion comprising about 1.5% w/w ruxolitinib phosphate on a free base basis, about 0.005% w/w calcipotriol, about 55% w/w purified water, about 0.05% w/w disodium EDTA, about 7% w/w PEG300, about 6.5% w/w propylene glycol, about 0.1% w/w methylparaben, about 0.05% w/w propylparaben, about 0.4% w/w xanthan gum, about 7% w/w white petrolatum, about 4% w/w light mineral oil, about 3% w/w glycerol stearate SE, about 3% w/w cetyl alcohol, about 1.75% w/w stearyl alcohol, about 1% w/w dimethicone, about 7% w/w medium chain triglycerides, about 1.25% w/w polysorbate 20, and about 0.5% w/w phenoxyethanol.

In some embodiments, the present disclosure also provides pharmaceutical formulations for topical treatment of a skin disease (or, alternatively, a method of any one of embodiments 1-75), wherein the formulation is an oil-in-water emulsion comprising about 1.5% w/w ruxolitinib phosphate on a free base basis, about 0.005% w/w calcipotriol, about 55% w/w purified water, about 0.05% w/w disodium EDTA, about 7% w/w PEG400, about 6.5% w/w propylene glycol, about 0.1% w/w methylparaben, about 0.05% w/w propylparaben, about 0.4% w/w xanthan gum, about 7% w/w white petrolatum, about 4% w/w light mineral oil, about 3% w/w glycerol stearate SE, about 3% w/w cetyl alcohol, about 1.75% w/w stearyl alcohol, about 1% w/w dimethicone, about 7% w/w medium chain triglycerides, about 1.25% w/w polysorbate 20, and about 0.5% w/w phenoxyethanol.

In some embodiments, the pH of pharmaceutical formulation described herein is adjusted with trolamine (triethanolamine). In some embodiments, the pH of pharmaceutical formulation described herein is adjusted with phosphoric acid.

In some embodiments, the emulsion formulations of ruxolitinib described supra, may also be used in the fixed-dose combination formulations described as follows. The topical formulation described above can utilize any of the vitamin D derivatives, vitamin D3 analogs, and JAK inhibitors described supra in any suitable combination.

As used in the context of "topical treatment of a skin disease", "topical" means administration to the skin.

Pharmaceutical formulations for topical administration for administration to skin may include solutions, suspensions, foams, ointments, lotions, creams, gels, sprays, liquids, and powders. Conventional pharmaceutical carriers, aqueous, powder or oily bases, thickeners and the like may be necessary or desirable. In some embodiments, the composition is formulated for topical administration by solution, suspension, gel, cream, ointment, lotion, spray, foam, liquid, and powder.

For the treatment of skin diseases as described herein, topical drugs, which are able to penetrate the skin barrier and provide limited systemic effects, are of particular importance.

Topical (dermal/intradermal) formulations are typically solutions, suspensions, gels, creams, ointments, lotions, sprays and foams. Preferred topical formulations should be physically and chemically stable, not cause skin irritation, and deliver the active agent at the appropriate layer of the skin in concentrations that would result in therapeutic response, with limited systemic exposure.

In some embodiments, the administration is topical and comprised of formulations with one or more pharmaceutically (e.g., dermatologically) acceptable excipients. Examples of dermatologically acceptable excipients include, but are not limited to, a pH adjusting agents, chelating agents, preservatives, co-solvents, penetration enhancers, humectants, thickening, gelling, viscosity building agents, surfactants, propellants, fragrance, colorants, or any combination or mixture thereof. In some embodiments, the topical formulation is administered locally to the patient (e.g., administered at the site of a lesion).

In some embodiments, the pH-adjusting agent is selected from an acid, an acid salt, a base, a base salt, and a buffer, or any mixture thereof. Exemplary acids include, but are not limited to, lactic acid, acetic acid, citric acid, and benzoic acid, and salts thereof. Exemplary buffers include, but are not limited to, citrate/citric acid, acetate/acetic acid, edetate/edetic acid, lactate/lactic acid, and the like.

In some embodiments, the chelating agent is a single excipient. In some embodiments, the chelating agent is a mixture of two or more chelating agents. Exemplary chelating agents include, but are not limited to, ethylenediaminetetraacetic acid (EDTA), or a salt thereof. In some embodiments, the chelating agent comprises a mixture of a chelating agent and an antioxidant, wherein the chelating agent and antioxidant prevent, minimize, or reduce oxidative degradation reactions in the composition. Exemplary antioxidants include, but are not limited to, butylated hydroxytoluene (BHT), butylated hydroxyanisole (BHA), tocopherol, and propyl gallate.

In some embodiments, the composition comprises one or more preservatives. In some embodiments, the composition comprises a mixture of two or more preservatives. In some embodiments, the composition comprises one to five preservatives. Exemplary preservatives include, but are not limited to, benzyl alcohol, phenonyexthanol, methyl paraben, ethyl paraben, propyl paraben, butyl paraben, and imidazolidinyl urea.

In some embodiments, the composition comprises one or more co-solvents. In some embodiments, the composition comprises a mixture of two or more co-solvents. In some embodiments, the composition comprises one to five co-solvents. Exemplary solvents include, but are not limited to, water, propylene glycol, diethylene glycol monoethyl ether, dimethyl isosorbide, ethyl alcohol, isopropyl alcohol, benzyl alcohol, propanediol, propylene glycol, polyethylene glycols (e.g., polyethylene glycol 200, polyethylene glycol 300, polyethylene glycol 400, and the like). In some embodiments, the solvent is a non-water soluble agent. Exemplary non-water soluble agents include, but are not limited to, diethyl sebacate, diisopropyl adipate, isopropyl myristate, isopropyl palmitate, and medium chain triglycerides.

In some embodiments, the composition comprises one or more penetration enhancers. In some embodiments, the composition comprises a mixture of two or more penetration enhancers. In some embodiments, the composition comprises one to five penetration enhancers. The penetration enhancers can act as both a solvent and a penetration enhancer. Exemplary penetration enhancers include, but are not limited to, fatty acids, fatty acid esters, fatty alcohols, pyrrolidones, sulfoxides, alcohols, diols and polyols, or any mixture thereof. In some embodiments, a co-solvent provided herein is a penetration enhancer.

In some embodiments, the composition comprises one or more thickening, gelling, or viscosity building agents. In some embodiments, the composition comprises a mixture of two or more thickening, gelling, or viscosity building agents. In some embodiments, the composition comprises one to five thickening, gelling, or viscosity building agents. Exemplary thickening, gelling, or viscosity building agents include, but are not limited to, cellulosic derivatives (e.g., hydroxyethylcellulose (HEC), carboxymethylcellulose, hydroxypropylcellulose (HPC), and hydroxypropyl methylcellulose (HPMC), and polyvinylpyrrolidone (PVP).

The surfactant is a compound that lowers the surface tension between two liquids or between a liquid and a solid. Surfactant may be a mixture of two or more surfactants. Exemplary surfactants include, but are not limited to, ethoxylated fatty alcohol ether (e.g., steareth-2, steareth-10, steareth-20, ceteareth-2, ceteareth-10, and the like), PEG esters (e.g., PEG-4 dilaurate, PEG-20 stearate, and the like), Glyceryl esters or derivatives thereof (e.g., glyceryl dioleate, glyceryl stearate, and the like), polymeric ethers (e.g., poloxamer 124, poloxamer 181, poloxamer 182, poloxamer 407, and the like), sorbitan derivatives (e.g., polysorbate 80, sorbitan monostearate, and the like), fatty alcohols (e.g., cetyl alcohol, stearyl alcohol, cetearyl alcohol, and the like), and emulsifying wax (e.g., emulsifying wax NF, mixtures of mixture of cetearyl alcohol and polysorbate 60, and the like).

Topical (e.g., intradermal) administration provides the advantage of treating the skin diseases and/or disorder as described herein locally, minimizing potential adverse events associated with systemic exposure, and allowing an easier discontinuation of the therapy, if necessary. Additionally, some topical dosage forms such as creams, ointments, and gels have the benefit of excipients that may act as emollients or occlusive agents, which can increase patient well-being and compliance during the treatment period. Other dosage routes such as oral, parenteral, and inhalation may lead to supratherapeutic systemic drug levels, increased likelihood of adverse events, drug-drug interactions, and generation of active/toxic metabolites, which may result in treatment discontinuation and inadequate patient compliance.

Topical formulations intended for dermal delivery are typically solutions, suspensions, gels, creams, ointments, lotions, sprays, and foams and can contain one or more conventional carriers as described herein. The formulation composition should be prepared with the goal of delivering the active ingredient to the appropriate layer(s) of the skin, minimizing systemic exposure, and preventing skin irritation. Additionally, the pharmaceutical composition should be physically and chemically stable. Depending on the selected dosage form, one or more additional excipients as described herein may be necessary, e.g., pH adjusting agents, chelating agents, preservatives, co-solvents, penetration enhancers, humectants, thickening, gelling, viscosity building agents, surfactants, propellants, fragrances, colorants, or any combination or mixture thereof.

In some embodiments, topical formulations can contain one or more conventional carriers as described herein. In some embodiments, ointments can contain water and one or more hydrophobic carriers selected from, for example, liquid paraffin, polyoxyethylene alkyl ether, propylene glycol, white petrolatum, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration.

The compositions of the presently claimed subject matter can further include one or more additional pharmaceutical agents, examples of which are listed hereinabove.

Combination Therapies

The methods described herein can further comprise administering one or more additional therapeutic agents. The one or more additional therapeutic agents can be administered to a patient simultaneously or sequentially.

In some embodiments, the additional therapeutic agent is an antibiotic. In some embodiments, the antibiotic is clindamycin, doxycycline, minocycline, trimethoprim-sulfamethoxazole, erythromycin, metronidazole, rifampin, moxifloxacin, dapsone, or a combination thereof. In some embodiments, the antibiotic is clindamycin, doxycycline, minocycline, trimethoprim-sulfamethoxazole, or erythromycin in combination with metronidazole. In some embodiments, the antibiotic is a combination of rifampin, moxifloxacin, and metronidazole. In some embodiments, the antibiotic is a combination of moxifloxacin and rifampin.

In some embodiments, the additional therapeutic agent is a retinoid. In some embodiments, the retinoid is adapalene, etretinate, acitretin, or isotretinoin.

In some embodiments, the additional therapeutic agent is a steroid. In some embodiments, the additional therapeutic agent is a corticosteroid. In some embodiments, the steroid is such as triamcinolone, dexamethasone, fluocinolone, cortisone, prednisone, prednisolone, or flumetholone.

In some embodiments, the additional therapeutic agent is an immunosuppressant. In some embodiments, the immunosuppressant is methotrexate or cyclosporin A. In some embodiments, the immunosuppressant is mycophenolate mofetil or mycophenolate sodium.

In some embodiments, the additional therapeutic agent is azelaic acid.

In some embodiments, the additional therapeutic agent is for topical treatment. In some embodiments, the additional therapeutic agent is for treating psoriasis, atopic dermatitis, alopecia, vitiligo, Reiter's syndrome, pityriasis rubra pilaris, epidermolysis bullosa simplex, palmoplantar keratoderma, pachyonychia congenita, steatocystoma multiplex, cutaneous lichen planus, cutaneous T-cell lymphoma, hidradenitis suppurativa, contact dermatitis, and ichthyosis. In some embodiments, the additional therapeutic agent is for treating atopic dermatitis. In some embodiments, the additional therapeutic agent is pimecrolimus. In some embodiments, the additional therapeutic agent is for treating psoriasis. In some embodiments, the additional therapeutic agent is for treating alopecia. In some embodiments, the additional therapeutic agent is for treating vitiligo. In some embodiments, the additional therapeutic agent is for treating Reiter's syndrome. In some embodiments, the additional therapeutic agent is for treating pityriasis rubra pilaris. In some embodiments, the additional therapeutic agent is for treating epidermolysis bullosa simplex. In some embodiments, the additional therapeutic agent is for treating palmoplantar keratoderma. In some embodiments, the additional therapeutic agent is for treating pachyonychia congenita. In some embodiments, the additional therapeutic agent is for treating steatocystoma multiplex. In some embodiments, the additional therapeutic agent is for treating cutaneous lichen planus. In some embodiments, the additional therapeutic agent is for treating cutaneous T-cell lymphoma. In some embodiments, the additional therapeutic agent is for treating hidradenitis suppurativa. In some embodiments, the additional therapeutic agent is for treating contact dermatitis. In some embodiments, the additional therapeutic agent is for treating ichthyosis.

In some embodiments, the additional therapeutic agent is crisaborole.

In some embodiments, the additional therapeutic agent is tacrolimus.

In some embodiments, the additional therapeutic agent is pimecrolimus.

Kits

The present disclosure also includes pharmaceutical kits useful, for example, in the treatment and/or prevention of skin diseases as described herein such as psoriasis, alopecia, and vitiligo, which include one or more containers containing a pharmaceutical composition comprising a therapeutically effective amount of ruxolitinib, or a pharmaceutically acceptable salt thereof, as described herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

It is further appreciated that certain features of the presently claimed subject matter, which are, for clarity, described in the context of separate embodiments, can also be provided in combination in a single embodiment. Conversely, various features of the presently claimed subject matter, which are, for brevity, described in the context of a single embodiment, can also be provided separately or in any suitable subcombination.

Definitions

As used herein, "an affected skin area" refers to an area of the patient's skin having a skin disease as described herein.

As used herein, "ruxolitinib phosphate" means the phosphoric acid salt of ruxolitinib, wherein the ruxolitinib and phosphoric acid are in a 1:1 ratio.

As used herein, "cream" means an emulsion, semisolid dosage form for application to the skin.

As used herein, the term "$C_{3-4}$ cycloalkyl", employed alone or in combination with other terms, refers to a non-aromatic monocyclic hydrocarbon moiety, having 3-4 carbon atoms, which may optionally contain one or more alkenylene groups as part of the ring structure. One or more ring-forming carbon atoms of a cycloalkyl group can be oxidized to form carbonyl linkages. Exemplary $C_{3-4}$ cycloalkyl groups include cyclopropyl, cyclobutyl, and the like. In some embodiments, the cycloalkyl group is cyclopropyl. In some embodiments, the cycloalkyl group is cyclobutyl.

As used herein, the term "synergy" or "synergistic effect" when used in connection with a description of the efficacy of a combination of agents or compounds, means any measured effect of the combination which is greater that the effect predicted from a sum of the effects of the individual agents or compounds. For example, as described herein, there are synergistic effects of inhibiting IL-22, MMP12, and CXCL10 respectively between (a) a JAK inhibitor, or a pharmaceutically acceptable salt thereof, and (b) vitamin D3, a vitamin D3 analog, or a pharmaceutically acceptable salt thereof, which means that total inhibiting effects from the combination of (a) and (b) is greater than the sum of the inhibition effects of (a) and (b) alone.

As used herein, "statistically significant" means a p-value of <0.05 (preferably <0.001, and most preferably <0.0001).

As used herein, the phrase "pharmaceutically acceptable" means those compounds, materials, compositions, and/or dosage forms, which are, within the scope of sound medical judgment, suitable for use in contact with tissues of humans and animals. In some embodiments, "pharmaceutically acceptable" means approved by a regulatory agency of the Federal or a state government or listed in the U.S. Pharmacopeia or other generally recognized pharmacopeia for use in animals, and more particularly in humans.

The presently claimed subject matter also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the presently claimed subject matter include the conventional non-toxic salts of the parent compound formed, for example, from non-toxic inorganic or organic acids. The pharmaceutically acceptable salts of the presently claimed subject matter can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (MeCN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety. In some embodiments, the pharmaceutically acceptable salt is a phosphoric acid salt, a sulfuric acid salt, or a maleic acid salt.

As used herein, the term "emulsifier component" refers to, in one aspect, to a substance, or mixtures of substances that maintains an element or particle in suspension within a fluid medium. In some embodiments, the emulsifier component allows an oil phase to form an emulsion when combined with water. In some embodiments, the emulsifier component refers to one or more non-ionic surfactants.

As used herein, the term "occlusive agent component" refers to a hydrophobic agent or mixtures of hydrophobic agents that form an occlusive film on skin that reduces transepidermal water loss (TEWL) by preventing evaporation of water from the stratum corneum.

As used herein, the term "stiffening agent component" refers to a substance or mixture of substances that increases the viscosity and/or consistency of the cream or improves the rheology of the cream.

As used herein, the term "emollient component" refers to an agent that softens or soothes the skin or soothes an irritated internal surface.

As used herein, the term "stabilizing agent component" refers to a substance or mixture of substances that improves the stability of the cream and/or the compatibility of the components in the cram. In some embodiments, the stabilizing agent component prevents agglomeration of the emulsion and stabilizes the droplets in the oil-in-water emulsion.

As used herein, the term "solvent component" is a liquid substance or mixture of liquid substances capable of dissolving a JAK inhibitor as described herein such as ruxolitinib, or a pharmaceutically acceptable salt thereof, or other substances in the cream. In some embodiments, the solvent component is a liquid substance or mixture of liquid substances in which, ruxolitinib, or its pharmaceutically acceptable salt, has reasonable solubility. For example, solubilities of ruxolitinib (free base) or its phosphate salt (1:1 salt) are reported in Table 1. In some embodiments, a solvent is a substance or mixture thereof, in which ruxolitinib, or its pharmaceutically acceptable salt (whichever is used), has a solubility of at least about 10 mg/mL or greater, at least about 15 mg/mL or greater, or at least about 20 mg/mL or greater.

As used herein, the phrase "antimicrobial preservative component" is a substance or mixtures of substances, which inhibits microbial growth in the cream.

As used herein, the phrase "chelating agent component" refers to a compound or mixtures of compounds that has the ability to bind strongly with metal ions.

As used herein, "% by weight of the emulsion" means the percent concentration of the component in the emulsion is on weight/weight basis. For example, 1% w/w of component A=[(mass of component A)/(total mass of the emulsion)]×100.

As used herein, "% by weight of the emulsion on a free base basis" of a JAK inhibitor as described herein such as ruxolitinib, or a pharmaceutically acceptable salt thereof" means that the % w/w is calculated based on the weight of ruxolitinib in the total emulsion. For example, "1.5% w/w on a free base basis" of ruxolitinib phosphate means that for 100 grams of total formulation, there are 1.98 grams of ruxolitinib phosphate in the emulsion (which equates to 1.5 grams of the free base, ruxolitinib).

As used herein, "% by weight of the formulation on a free base basis" of a JAK inhibitor as described herein such as ruxolitinib, or pharmaceutically acceptable salt thereof" means that the % w/w is calculated based on the weight of ruxolitinib in the total formulation. For example, "1.5% w/w on a free base basis" of ruxolitinib phosphate means that for 100 grams of total formulation, there are 1.98 grams of ruxolitinib phosphate in the formulation (which equates to 1.5 grams of the free base, ruxolitinib).

As used herein, the term "component" can mean one substance or a mixture of substances.

As used herein, the term "fatty acid" refers to an aliphatic acid that is saturated or unsaturated. In some embodiments, the fatty acid is in a mixture of different fatty acids. In some embodiments, the fatty acid has between about eight to about thirty carbons on average. In some embodiments, the fatty acid has about 12 to 20, 14-20, or 16-18 carbons on average. Suitable fatty acids include, but are not limited to, cetyl acid, stearic acid, lauric acid, myristic acid, erucic acid, palmitic acid, palmitoleic acid, capric acid, caprylic acid, oleic acid, linoleic acid, linolenic acid, hydroxystearic acid, 12-hydroxystearic acid, cetostearic acid, isostearic acid, sesquioleic acid, sesqui-9-octadecanoic acid, sesquiisooctadecanoic acid, behenic acid, isobehenic acid, and arachidonic acid, or mixtures thereof.

As used herein, the term "fatty alcohol" refers to an aliphatic alcohol that is saturated or unsaturated. In some embodiments, the fatty alcohol is in a mixture of different fatty alcohols. In some embodiments, the fatty alcohol has between about 12 to about 20, about 14 to about 20, or about 16 to about 18 carbons on average. Suitable fatty alcohols include, but are not limited to, stearyl alcohol, lauryl alcohol, palmityl alcohol, cetyl alcohol, capryl alcohol, caprylyl alcohol, oleyl alcohol, linolenyl alcohol, arachidonic alcohol, behenyl alcohol, isobehenyl alcohol, selachyl alcohol, chimyl alcohol, and linoleyl alcohol, or mixtures thereof.

As used herein, the term "polyalkylene glycol", employed alone or in combination with other terms, refers to a polymer containing oxyalkylene monomer units, or copolymer of different oxyalkylene monomer units, wherein the alkylene group has 2 to 6, 2 to 4, or 2 to 3 carbon atoms. As used herein, the term "oxyalkylene", employed alone or in combination with other terms, refers to a group of formula —O-alkylene-. In some embodiments, the polyalkylene glycol is polyethylene glycol.

As used herein, the term, "sorbitan fatty ester" includes products derived from sorbitan or sorbitol and fatty acids and, optionally, poly (ethylene glycol) units, including sorbitan esters and polyethoxylated sorbitan esters. In some embodiments, the sorbitan fatty ester is a polyethoxylated sorbitan ester.

As used herein, the term "sorbitan ester" refers to a compound, or mixture of compounds, derived from the esterification of sorbitol and at least one fatty acid. Fatty acids useful for deriving the sorbitan esters include, but are not limited to, those described herein. Suitable sorbitan esters include, but are not limited to, the Span™ series (available from Uniqema), which includes Span 20 (sorbitan monolaurate), 40 (sorbitan monopalmitate), 60 (sorbitan monostearate), 65 (sorbitan tristearate), 80 (sorbitan monooleate), and 85 (sorbitan trioleate). Other suitable sorbitan esters include those listed in R. C. Rowe and P. J. Shesky, Handbook of pharmaceutical excipients, (2006), 5th ed., which is incorporated herein by reference in its entirety.

As used herein, the term "polyethoxylated sorbitan ester" refers to a compound, or mixture thereof, derived from the ethoxylation of a sorbitan ester. The polyoxethylene portion of the compound can be between the fatty ester and the sorbitan moiety. As used herein, the term "sorbitan ester" refers to a compound, or mixture of compounds, derived from the esterification of sorbitol and at least one fatty acid. Fatty acids useful for deriving the polyethoyxlated sorbitan esters include, but are not limited to, those described herein. In some embodiments, the polyoxyethylene portion of the compound or mixture has about 2 to about 200 oxyethylene units. In some embodiments, the polyoxyethylene portion of the compound or mixture has about 2 to about 100 oxyethylene units. In some embodiments, the polyoxyethylene portion of the compound or mixture has about 4 to about 80 oxyethylene units. In some embodiments, the polyoxyethylene portion of the compound or mixture has about 4 to about 40 oxyethylene units. In some embodiments, the polyoxyethylene portion of the compound or mixture has about 4 to about 20 oxyethylene units. Suitable polyethoxylated sorbitan esters include, but are not limited to the Tween™ series (available from Uniqema), which includes Tween 20 (POE(20) sorbitan monolaurate), 21 (POE(4) sorbitan monolaurate), 40 (POE(20) sorbitan monopalmitate), 60 (POE(20) sorbitan monostearate), 60K (POE(20) sorbitan monostearate), 61 (POE(4) sorbitan monostearate), 65 (POE(20) sorbitan tristearate), 80 (POE(20) sorbitan monooleate), 80K (POE(20) sorbitan monooleate), 81 (POE (5) sorbitan monooleate), and 85 (POE(20) sorbitan trioleate). As used herein, the abbreviation "POE" refers to polyoxyethylene. The number following the POE abbreviation refers to the number of oxyethylene repeat units in the compound. Other suitable polyethoxylated sorbitan esters include the polyoxyethylene sorbitan fatty acid esters listed in R. C. Rowe and P. J. Shesky, Handbook of pharmaceutical excipients, (2006), 5th ed., which is incorporated herein by reference in its entirety. In some embodiments, the polyethoxylated sorbitan ester is a polysorbate. In some embodiments, the polyethoxylated sorbitan ester is polysorbate 20.

As used herein, the term "glyceryl fatty esters" refers to mono-, di- or triglycerides of fatty acids. The glyceryl fatty esters may be optionally substituted with sulfonic acid groups, or pharmaceutically acceptable salts thereof. Suitable fatty acids for deriving glycerides of fatty acids include, but are not limited to, those described herein. In some embodiments, the glyceryl fatty ester is a mono-glyceride of a fatty acid having 12 to 18 carbon atoms. In some embodiments, the glyceryl fatty ester is glyceryl stearate.

As used herein, the term "triglycerides" refers to a triglyceride of a fatty acid. In some embodiments, the triglyceride is medium chain triglycerides.

As used herein, the term "alkylene glycol" refers to a group of formula —O-alkylene-, wherein the alkylene group has 2 to 6, 2 to 4, or 2 to 3 carbon atoms. In some embodiments, the alkylene glycol is propylene glycol (1,2-propanediol).

As used herein, the term "polyethylene glycol" refers to a polymer containing ethylene glycol monomer units of formula —O—CH$_2$—CH$_2$—. Suitable polyethylene glycols may have a free hydroxyl group at each end of the polymer molecule, or may have one or more hydroxyl groups etherified with a lower alkyl, e.g., a methyl group. Also suitable are derivatives of polyethylene glycols having esterifiable carboxy groups. Polyethylene glycols useful in the present disclosure can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to polyethylene glycol-200, polyethylene glycol-300, polyethylene glycol-400, polyethylene glycol-600, and polyethylene glycol-900. The number following the dash in the name refers to the average molecular weight of the polymer.

As used herein, "contains" is equivalent to "comprises".

As used herein, the term "subject," "individual," or "patient," used interchangeably, refers to humans. In some embodiments, the "subject," "individual," or "patient" is in need of said treatment.

In some embodiments, the compounds, or pharmaceutically acceptable salts thereof, or pharmaceutical formulations thereof, topical formulations thereof, as described herein are administered in a therapeutically effective amount. As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease; or (3) preventing the disease, condition or disorder in an individual who may be predisposed to the disease, condition or disorder but does not yet experience or display the pathology or symptomatology of the disease. In some embodiments, treating refers to inhibiting or ameliorating the disease. In some embodiments, treating is preventing the disease.

In some embodiments, the components are present in exactly the ranges specified (e.g., the term "about" is not present). In some embodiments, "about" means plus or minus 10% of the value.

The present disclosure also provides the following non-limiting embodiments:

In order that the embodiments disclosed herein may be more efficiently understood, examples are provided below. It should be understood that these examples are for illustrative purposes only and are not to be construed as limiting the embodiments in any manner.

In some embodiments, the following embodiments are provided:

1. A method of treating a skin disease in a patient in need thereof, comprising topically administering to an affected area of the patient (a) a JAK inhibitor, or a pharmaceutically acceptable salt thereof, and (b) vitamin D3, a vitamin D3 analog, or a pharmaceutically acceptable salt thereof.

2. The method of embodiment 1, the skin disease is an autoimmune skin disease.

3. The method of embodiment 1 or 2, the skin disease is an inflammatory skin disease.

4. The method of any one of embodiments 1-3, wherein the skin disease is a Th1 or Th17 associated skin disease.

5. The method of any one of embodiments 1-4, wherein the skin disease is mediated by interleukin 22 (IL-22), C-X-C motif chemokine 10 (CXCL10), matrix metallopeptidase 12 (MMP12), or a combination thereof.

6. The method of any one of embodiments 1-5, wherein the skin disease is mediated by IL-22.

7. The method of any one of embodiments 1-5, wherein the skin disease is mediated by MMP12.

8. The method of any one of embodiments 1-5, wherein the skin disease is mediated by CXCL10.

9. The method of any one of embodiments 1-8, wherein the skin disease is selected from psoriasis, atopic dermatitis, alopecia, vitiligo, Reiter's syndrome, pityriasis rubra pilaris, epidermolysis bullosa simplex, palmoplantar keratoderma, pachyonychia congenita, steatocystoma multiplex, cutaneous lichen planus, cutaneous T-cell lymphoma, hidradenitis suppurativa, contact dermatitis, and ichthyosis.

10. The method of embodiment 9, wherein the skin disease is psoriasis.

11. The method of embodiment 9, wherein the skin disease is alopecia.

12. The method of embodiment 11, wherein the alopecia is alopecia areata.

13. The method of embodiment 9, wherein the skin disease is vitiligo.

14. The method of any one embodiments 1-13, wherein (a) the JAK inhibitor, or the pharmaceutically acceptable salt thereof, and (b) the vitamin D3, the vitamin D3 analog, or a pharmaceutically acceptable salt thereof, are administered simultaneously.

15. The method of any one of embodiments 1-13, wherein (a) the JAK inhibitor, or the pharmaceutically acceptable salt thereof, and (b) the vitamin D3, the vitamin D3 analog, or a pharmaceutically acceptable salt thereof, are administered sequentially.

16. The method of any one of embodiments 1-15, wherein (a) the JAK inhibitor, or the pharmaceutically acceptable salt thereof, and (b) the vitamin D3, the vitamin D3 analog, or a pharmaceutically acceptable salt thereof, are administered at least one time per day.

17. The method of any one of embodiments 1-15, wherein the JAK inhibitor, or the pharmaceutically acceptable salt thereof, is administered once per day.

18. The method of any one of embodiments 1-15, wherein the JAK inhibitor, or the pharmaceutically acceptable salt thereof, is administered twice per day.

19. The method of any one embodiment 1-18, wherein the vitamin D3, the vitamin D3 analog, or the pharmaceutically acceptable salt thereof, is administered once per day.

20. The method of any one embodiment 1-18, wherein the vitamin D3, the vitamin D3 analog, or the pharmaceutically acceptable salt thereof, is administered twice per day.

21. The method of any one embodiment 1-20, wherein (a) the JAK inhibitor, or the pharmaceutically acceptable salt thereof, and (b) the vitamin D3, the vitamin D3 analog, or the pharmaceutically acceptable salt thereof, are administered as separate formulations.

22. The method of any one embodiment 1-14, wherein (a) the JAK inhibitor, or the pharmaceutically acceptable salt thereof, and (b) the vitamin D3, the vitamin D3 analog, or the pharmaceutically acceptable salt thereof, are administered as a single formulation.

23. The method of embodiment 22, wherein (a) the JAK inhibitor, or the pharmaceutically acceptable salt thereof, and (b) the vitamin D3, the vitamin D3 analog, or the pharmaceutically acceptable salt thereof, are administered once per day.

24. The method of embodiment 22, wherein (a) the JAK inhibitor, or the pharmaceutically acceptable salt thereof, and (b) the vitamin D3, the vitamin D3 analog, or the pharmaceutically acceptable salt thereof, are administered twice per day.

25. The method of any one of embodiments 1-24, wherein the vitamin D3, the vitamin D3 analog, or the pharmaceutically acceptable salt thereof, is administered in a synergistic amount.

26. The method of any one embodiment 1-24, wherein there is a synergistic effect between the JAK inhibitor, or the pharmaceutically acceptable salt thereof, and the vitamin D3, the vitamin D3 analog, or the pharmaceutically acceptable salt thereof.

27. The method of any one of embodiments 1-26, further comprising administering an additional therapeutic agent.

28. The method of embodiment 27, wherein the additional therapeutic agent is a corticosteroid.

29. The method of any one of embodiments 1-28, wherein the patient is a human patient.

30. The method of any one of embodiments 1-29, wherein the vitamin D3, the vitamin D3 analog, or the pharmaceutically acceptable salt thereof, is a compound having Formula (I):

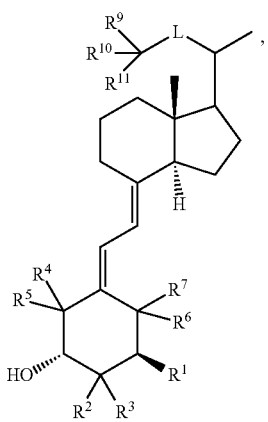

wherein:
$R^1$ is H or OH;
$R^2$ and $R^3$ are each H; or
$R^2$ is O—$R^{24}$; and $R^3$ is H; or
$R^2$ and $R^3$ are taken together to form a =CH$_2$ group;
$R^{24}$ is —C$_{1-4}$ alkylene-OH;
$R^4$ and $R^5$ are each H; or
$R^4$ and $R^5$ are taken together to form a =CH$_2$ group;
$R^6$ and $R^7$ are each H; or
$R^6$ and $R^7$ are taken together to form a =CH$_2$ group;
L is —CH$_2$—CH$_2$—CH(R$^{12}$)—, —CH$_2$—CH$_2$—CH$_2$—CH(R$^{12}$)—, —CH=CH—CH(R$^{12}$)—, —CH=CH—CH=CH—, —CH$_2$—C≡C—, —O—CH$_2$—CH$_2$—, or —O—CH$_2$—CH$_2$—CH$_2$—, wherein R$^{12}$ is H or OH;
$R^9$ is C$_{1-3}$ alkyl or C$_{1-4}$ haloalkyl;
$R^{10}$ is C$_{1-3}$ alkyl or C$_{1-4}$ haloalkyl;
$R^{11}$ is H or OH;
or, alternatively, $R^9$ and $R^{10}$ together with the carbon atom to which they are attached form a C$_{3-4}$ cycloalkyl ring; and $R^{11}$ is H.

31. The method of any one of embodiments 1-29, wherein the vitamin D3, the vitamin D3 analog, or the pharmaceutically acceptable salt thereof, is a compound having Formula (II):

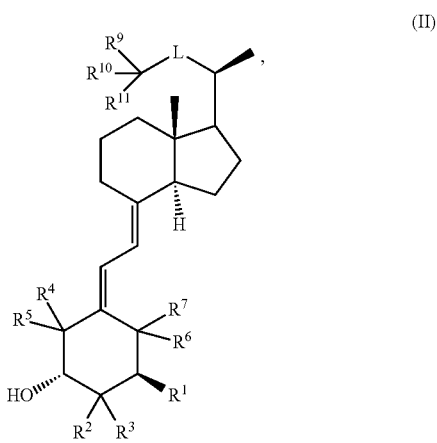

wherein:
$R^1$ is H or OH;
$R^2$ and $R^3$ are each H; or
$R^2$ is O—$R^{24}$; and $R^3$ is H; or
$R^2$ and $R^3$ are taken together to form a =CH$_2$ group;
$R^{24}$ is —C$_{1-4}$ alkylene-OH;
$R^4$ and $R^5$ are each H; or
$R^4$ and $R^5$ are taken together to form a =CH$_2$ group;
$R^6$ and $R^7$ are each H; or
$R^6$ and $R^7$ are taken together to form a =CH$_2$ group;
L is —CH$_2$—CH$_2$—CH(R$^{12}$)—, —CH$_2$—CH$_2$—CH$_2$—CH(R$^{12}$)—, —CH=CH—CH(R$^{12}$)—, —CH=CH—CH=CH—, —CH$_2$—C≡C—, —O—CH$_2$—CH$_2$—, or —O—CH$_2$—CH$_2$—CH$_2$—, wherein R$^{12}$ is H or OH;
$R^9$ is C$_{1-3}$ alkyl or C$_{1-4}$ haloalkyl;
$R^{10}$ is C$_{1-3}$ alkyl or C$_{1-4}$ haloalkyl;
$R^{11}$ is H or OH;
or, alternatively, $R^9$ and $R^{10}$ together with the carbon atom to which they are attached form a C$_{3-4}$ cycloalkyl ring; and $R^{11}$ is H.

32. The method of any one of embodiments 1-29, wherein (b) is a vitamin D3 analog, or a pharmaceutically acceptable salt thereof.

33. The method of embodiment 32, wherein the vitamin D3 analog, or the pharmaceutically acceptable salt thereof, is a vitamin 1α-(OH) D3 analog, or a pharmaceutically acceptable salt thereof.

34. The method of embodiment 32, wherein the vitamin D3 analog, or the pharmaceutically acceptable salt thereof, is a vitamin 1α,25(OH)$_2$ D3 analog, a vitamin 1α,24(OH)$_2$ D3 analog, or a vitamin 1α,26(OH)$_2$ D3 analog, or a pharmaceutically acceptable salt thereof.

35. The method of embodiment 32, wherein the vitamin D3 analog, or the pharmaceutically acceptable salt thereof, is a compound having Formula (III):

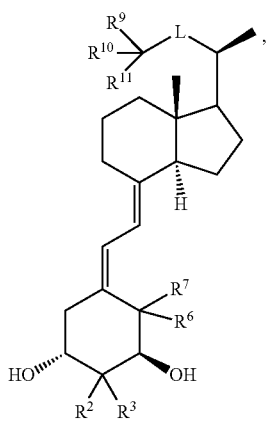

(III)

wherein:
- $R^2$ and $R^3$ are each H; or
- $R^2$ is O—$R^{2A}$; and $R^3$ is H;
- $R^{2A}$ is —$C_{1-4}$ alkylene-OH;
- $R^6$ and $R^7$ are each H; or
- $R^6$ and $R^7$ are taken together to form a =$CH_2$ group;
- L is —$CH_2$—$CH_2$—$CH(R^{12})$—, —CH=CH—CH($R^{12}$)—, —CH=CH—CH=CH—, —$CH_2$—C≡C—, —O—$CH_2$—$CH_2$—, —O—$CH_2$—$CH_2$—$CH_2$—, wherein $R^{12}$ is H or OH;
- $R^9$ is $CH_3$ or $CF_3$;
- $R^{10}$ is $CH_3$ or $CF_3$;
- $R^{11}$ is H or OH;
- or, alternatively, $R^9$ and $R^{10}$ together with the carbon atom to which they are attached form a cyclopropyl ring; and $R^{11}$ is H.

36. The method of embodiment 32, wherein the vitamin D3 analog, or the pharmaceutically acceptable salt thereof, is selected from calcidiol, calcitriol, calcipotriol, alfacalcidol, tacalcitol, maxacalcitol, falecalcitriol, eldecalcitol, inecalcitol, seocalcitol, lexicalcitol, 20-epi-1α,25(OH)$_2$D$_3$, CD-578 (17-methyl-19-nor-21-nor-23-yne-26,27-F6-1α,25 (OH)$_{2D3}$), TX527 (19-nor-14,20-bisepi-23-yne-1α,25 (OH)$_2$D$_3$), 2MD (2-methylene-19-nor-(20S)-1α,25 (OH)$_2$D$_3$), PRI-2205 ((5E,7E)-22-ene-26,27-dehydro-1α,25 (OH)$_2$D$_3$), ILX23-7553 (16-ene-23-yne-1α,25(OH)$_2$D$_3$), and MART-10(19-nor-2α-(3-hydroxypropyl)-1α,25 (OH)$_2$D$_3$).

37. The method of embodiment 32, wherein the vitamin D3 analog, or the pharmaceutically acceptable salt thereof, is calcipotriol.

38. The method of embodiment 32, wherein the vitamin D3 analog, or the pharmaceutically acceptable salt thereof, is maxacalcitol.

39. The method of embodiment 32, wherein the vitamin D3 analog, or the pharmaceutically acceptable salt thereof, is tacalcitol.

40. The method of any one of embodiments 32-39, wherein the vitamin D3 analog, or the pharmaceutically acceptable salt thereof, is administered in a topical formulation.

41. The method of embodiment 40, wherein the topical formulation is a foam, an ointment, a lotion, or a cream.

42. The method of embodiment 40 or 41, wherein the vitamin D3 analog, or the pharmaceutically acceptable salt thereof, is administered as a topical formulation comprising from about 0.0001% to about 0.1% of the vitamin D3 analog by weight of the formulation.

43. The method of embodiment 40 or 41, wherein the vitamin D3 analog, or the pharmaceutically acceptable salt thereof, is administered as a topical formulation comprising from about 0.0004% to about 0.005% of the vitamin D3 analog by weight of the formulation.

44. The method of embodiment 32, wherein the vitamin D3 analog, or the pharmaceutically acceptable salt thereof, is calcipotriol, or a pharmaceutically acceptable salt thereof which is administered as a topical formulation comprising about 50 µg calcipotriol per gram of the formulation.

45. The method of embodiment 44, wherein the topical formulation is a foam, an ointment, a lotion, or a cream.

46. The method of embodiment 44 or 45, wherein the topical formulation further comprises betamethasone dipropionate.

47. The method of embodiment 46, wherein the betamethasone dipropionate is present in an amount of about 0.5 mg per gram of the formulation.

48. The method of embodiment 33, wherein the vitamin D3 analog, or the pharmaceutically acceptable salt thereof, is tacalcitol, which is administered as a topical formulation comprising about 4 µg tacalcitol per gram of the formulation.

49. The method of embodiment 48, wherein the topical formulation is an ointment, a cream, or a lotion.

50. The method of embodiment 33, wherein the vitamin D3 analog, or the pharmaceutically acceptable salt thereof, is maxacalcitol, which is administered as a topical formulation comprising about 6 µg, about 12.5 µg, about 25 µg, or about 50 µg per gram of the formulation.

51. The method of embodiment 50, wherein the topical formulation is an ointment.

52. The method of any one of embodiments 1-51, wherein the JAK inhibitor, or the pharmaceutically acceptable salt thereof, is selected from a JAK1 inhibitor, a JAK2 inhibitor, a JAK3 inhibitor, a TYK2 inhibitor, a JAK1/JAK2 inhibitor, a JAK1/JAK3 inhibitor, a pan-JAK inhibitor, and a JAK1/TYK2 inhibitor, or a pharmaceutically acceptable salt.

53. The method of any one of embodiments 1-51, wherein the JAK inhibitor, or the pharmaceutically acceptable salt thereof, is a JAK1 inhibitor, or a pharmaceutically acceptable salt thereof.

54. The method of any one of embodiments 1-51, wherein the JAK inhibitor, or the pharmaceutically acceptable salt thereof, is a JAK2 inhibitor, or a pharmaceutically acceptable salt thereof.

55. The method of any one of embodiments 1-51, wherein the JAK inhibitor, or the pharmaceutically acceptable salt thereof, is a JAK1/JAK2 inhibitor, or a pharmaceutically acceptable salt thereof.

56. The method of any one of embodiments 1-51, wherein the JAK inhibitor, or the pharmaceutically acceptable salt thereof, is a JAK1/JAK3 inhibitor, or a pharmaceutically acceptable salt thereof.

57. The method of any one of embodiments 1-51, wherein the JAK inhibitor, or the pharmaceutically acceptable salt thereof, is a pan-JAK inhibitor, or a pharmaceutically acceptable salt thereof.

58. The method of any one of embodiments 1-51, wherein the JAK inhibitor, or the pharmaceutically acceptable salt thereof, is a JAK1/TYK2 inhibitor, or a pharmaceutically acceptable salt.

59. The method of any one of embodiments 1-51, wherein the JAK inhibitor, or the pharmaceutically acceptable salt thereof, is selected from ruxolitinib, baricitinib, oclacitinib, momelotinib, CTP-543, AH057, gandotinib, fedratinib, lestaurtinib, pacritinib, CHZ868, upadacitinib, tofacitinib, filgocitinib, abrocitinib, itacitinib, brepocitinib, ATI-501, ATI-1777, ATI-502, delgocitinib, peficitinib, gusacitinib, cucurbitacin I, cerdulatinib, decernotinib, BMS-986165, and ritlecitinib, or a pharmaceutically acceptable salt thereof.

60. The method of any one of embodiments 1-51, wherein the JAK inhibitor, or the pharmaceutically acceptable salt thereof, is selected from ruxolitinib, oclacitinib, baricitinib, momelotinib, CTP-543, gandotinib, fedratinib, lestaurtinib, pacritinib, upadacitinib, tofacitinib, filgocitinib, abrocitinib, itacitinib, brepocitinib, delgocitinib, peficitinib, gusacitinib, cucurbitacin I, and cerdulatinib, or a pharmaceutically acceptable salt thereof 61. The method of any one of embodiments 1-51, wherein the JAK inhibitor, or the pharmaceutically acceptable salt thereof, is ruxolitinib, or a pharmaceutically acceptable salt.

62. The method of any one of embodiments 1-51, the JAK inhibitor, or the pharmaceutically acceptable salt thereof, is ruxolitinib phosphate.

63. The method of embodiment 61 or 62, wherein the JAK inhibitor, or the pharmaceutically acceptable salt thereof, is administered as a cream formulation.

64. The method of embodiment 63, wherein the cream formulation is an oil-in-water emulsion.

65. The method of embodiment 63 or 64, wherein the cream formulation has a pH from about 2.8 to about 3.9.

66. The method of any one of embodiments 1-51, wherein the JAK inhibitor, or the pharmaceutically acceptable salt thereof, is delgocitinib, or a pharmaceutically acceptable salt thereof.

67. The method of any one of embodiments 1-51, wherein the JAK inhibitor, or the pharmaceutically acceptable salt thereof, is tofacitinib, or a pharmaceutically acceptable salt thereof.

68. The method of any one of embodiments 1-51, wherein the JAK inhibitor, or the pharmaceutically acceptable salt thereof, is ATI-1777, or a pharmaceutically acceptable salt thereof.

69. The method of any one of embodiments 1-51, wherein the JAK inhibitor, or the pharmaceutically acceptable salt thereof, is brepocitinib, or a pharmaceutically acceptable salt thereof.

70. The method of any one of embodiments 1-69, wherein the JAK inhibitor, or the pharmaceutically acceptable salt thereof, is administered in a therapeutically effective amount.

71. The method of any one of embodiments 1-70, wherein (b) vitamin D3, the vitamin D3 analog, or the pharmaceutically acceptable salt thereof, is administered in a therapeutically effective amount.

72. A method of treating a skin disease in a patient in need thereof, comprising topically administering to an affected area of the patient (a) ruxolitinib, or a pharmaceutically acceptable salt thereof, and (b) vitamin D3, a vitamin D3 analog, or a pharmaceutically acceptable salt thereof.

73. A method of treating a skin disease in a patient in need thereof, comprising topically administering to an affected area of the patient (a) ruxolitinib, or a pharmaceutically acceptable salt thereof, and (b) a vitamin D3 analog, or a pharmaceutically acceptable salt thereof.

74. The method of embodiment 73, wherein the vitamin D3 analog, or the pharmaceutically acceptable salt thereof, is calcipotriol, or a pharmaceutically acceptable salt thereof.

75. The method of any one of embodiments 72-74, wherein the ruxolitinib, or the pharmaceutically acceptable salt thereof, is ruxolitinib phosphate.

76. A pharmaceutical formulation for topical treatment of a skin disease, comprising (or, alternatively, a method of any one of embodiments 1-75, wherein the formulation comprises) (a) a JAK inhibitor, or a pharmaceutically acceptable salt thereof, and (b) vitamin D3, a vitamin D3 analog, or a pharmaceutically acceptable salt thereof.

77. A pharmaceutical formulation for topical treatment of a skin disease, comprising (or, alternatively, a method of any one of embodiments 1-75, wherein the formulation comprises), comprising (a) ruxolitinib, or a pharmaceutically acceptable salt thereof, and (b) vitamin D3, a vitamin D3 analog, or a pharmaceutically acceptable salt thereof.

78. The formulation (or, alternatively, the method) of embodiment 77, wherein the ruxolitinib, or the pharmaceutically acceptable salt thereof, is present in an amount of about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1.0%, about 1.05%, about 1.1%, about 1.15%, about 1.2%, about 1.25%, about 1.3%, about 1.35%, about 1.4%, about 1.45%, about 1.5%, about 1.55%, about 1.6%, about 1.65%, about 1.7%, about 1.75%, about 1.8%, about 1.85%, about 1.9%, about 1.95%, about 2.0%, about 2.5%, or about 3.0% by weight of the formulation on a free base basis.

79. A pharmaceutical formulation for topical treatment of a skin disease (or, alternatively, a method of any one of embodiments 1-75, wherein the formulation comprises), comprising (a) from about 0.75% w/w to about 1.5% w/w of ruxolitinib, or a pharmaceutically acceptable salt thereof, on a free base basis, and (b) vitamin D3, a vitamin D3 analog, or a pharmaceutically acceptable salt thereof.

80. A pharmaceutical formulation for topical treatment of a skin disease, comprising (or, alternatively, a method of any one of embodiments 1-75, wherein the formulation comprises) (a) about 0.75% w/w of ruxolitinib, or a pharmaceutically acceptable salt thereof, on a free base basis, and (b) vitamin D3, a vitamin D3 analog, or a pharmaceutically acceptable salt thereof.

81. A pharmaceutical formulation for topical treatment of a skin disease, comprising (or, alternatively, a method of any one of embodiments 1-75, wherein the formulation comprises) (a) about 1.5% w/w of ruxolitinib, or a pharmaceutically acceptable salt thereof, on a free base basis, and (b) vitamin D3, a vitamin D3 analog, or a pharmaceutically acceptable salt thereof.

82. A pharmaceutical formulation for topical treatment of a skin disease, comprising (or, alternatively, a method of any one of embodiments 1-75, wherein the formulation comprises) (a) from about 0.75% w/w to about 1.5% w/w of ruxolitinib, or a pharmaceutically acceptable salt thereof, on a free base basis, and (b) from about 1 µg/mL to about 50 µg/mL of vitamin D3, a vitamin D3 analog, or a pharmaceutically acceptable salt thereof, on a free base basis.

83. A pharmaceutical formulation for topical treatment of a skin disease, comprising (or, alternatively, a method of any one of embodiments 1-75, wherein the formulation comprises) (a) about 0.75% w/w of ruxolitinib, or a pharmaceutically acceptable salt thereof, on a free base basis, and (b) from about 1 µg/mL to about 50 µg/mL of vitamin D3, a vitamin D3 analog, or a pharmaceutically acceptable salt thereof, on a free base basis.

84. A pharmaceutical formulation for topical treatment of a skin disease, comprising (or, alternatively, a method of any one of embodiments 1-75, wherein the formulation comprises) (a) from about 0.75% w/w to about 1.5% w/w of ruxolitinib, or a pharmaceutically acceptable salt thereof, on a free base basis, and (b) about 1 µg/mL of vitamin D3, a vitamin D3 analog, or a pharmaceutically acceptable salt thereof, on a free base basis.

85. A pharmaceutical formulation for topical treatment of a skin disease, comprising (or, alternatively, a method of any one of embodiments 1-75, wherein the formulation comprises) (a) from about 0.75% w/w to about 1.5% w/w of ruxolitinib, or a pharmaceutically acceptable salt thereof, on a free base basis, and (b) about 10 µg/mL of vitamin D3, a vitamin D3 analog, or a pharmaceutically acceptable salt thereof, on a free base basis. A pharmaceutical formulation for topical treatment of a skin disease, comprising (or, alternatively, a method of any one of embodiments 1-75, wherein the formulation comprises) (a) from about 0.75% w/w to about 1.5% w/w of ruxolitinib, or a pharmaceutically acceptable salt thereof, on a free base basis, and (b) about 50 µg/mL of vitamin D3, a vitamin D3 analog, or a pharmaceutically acceptable salt thereof, on a free base basis.

86. A pharmaceutical formulation for topical treatment of a skin disease, comprising (or, alternatively, a method of any one of embodiments 1-75, wherein the formulation comprises) (a) about 0.75% w/w of ruxolitinib, or a pharmaceutically acceptable salt thereof, on a free base basis, and (b) about 1 µg/mL of vitamin D3, a vitamin D3 analog, or a pharmaceutically acceptable salt thereof, on a free base basis.

87. A pharmaceutical formulation for topical treatment of a skin disease, comprising (or, alternatively, a method of any one of embodiments 1-75, wherein the formulation comprises) (a) about 0.75% w/w of ruxolitinib, or a pharmaceutically acceptable salt thereof, on a free base basis, and (b) about 10 µg/mL of vitamin D3, a vitamin D3 analog, or a pharmaceutically acceptable salt thereof, on a free base basis.

88. A pharmaceutical formulation for topical treatment of a skin disease, comprising (or, alternatively, a method of any one of embodiments 1-75, wherein the formulation comprises) (a) about 0.75% w/w of ruxolitinib, or a pharmaceutically acceptable salt thereof, on a free base basis, and (b) about 50 µg/mL of vitamin D3, a vitamin D3 analog, or a pharmaceutically acceptable salt thereof, on a free base basis.

89. A pharmaceutical formulation for topical treatment of a skin disease, comprising (or, alternatively, a method of any one of embodiments 1-75, wherein the formulation comprises) (a) about 1.5% w/w of ruxolitinib, or a pharmaceutically acceptable salt thereof, on a free base basis, and (b) about 1 µg/mL of vitamin D3, a vitamin D3 analog, or a pharmaceutically acceptable salt thereof, on a free base basis.

90. A pharmaceutical formulation for topical treatment of a skin disease, comprising (or, alternatively, a method of any one of embodiments 1-75, wherein the formulation comprises) (a) about 1.5% w/w of ruxolitinib, or a pharmaceutically acceptable salt thereof, on a free base basis, and (b) about 10 µg/mL of vitamin D3, a vitamin D3 analog, or a pharmaceutically acceptable salt thereof, on a free base basis.

91. A pharmaceutical formulation for topical treatment of a skin disease, comprising (or, alternatively, a method of any one of embodiments 1-75, wherein the formulation comprises) (a) about 1.5% w/w of ruxolitinib, or a pharmaceutically acceptable salt thereof, on a free base basis, and (b) about 50 µg/mL of vitamin D3, a vitamin D3 analog, or a pharmaceutically acceptable salt thereof, on a free base basis.

92. A pharmaceutical formulation for topical treatment of a skin disease, comprising (or, alternatively, a method of any one of embodiments 1-75, wherein the formulation comprises) (a) from about 0.75% w/w to about 1.5% w/w of ruxolitinib, or a pharmaceutically acceptable salt thereof, on a free base basis, and (b) from about 0.0001% w/w to about 0.01% w/w of vitamin D3, a vitamin D3 analog, or a pharmaceutically acceptable salt thereof, on a free base basis.

93. A pharmaceutical formulation for topical treatment of a skin disease, comprising (or, alternatively, a method of any one of embodiments 1-75, wherein the formulation comprises) (a) from about 0.75% w/w to about 1.5% w/w of ruxolitinib, or a pharmaceutically acceptable salt thereof, on a free base basis, and (b) from about 0.0001% w/w to about 0.005% w/w of vitamin D3, a vitamin D3 analog, or a pharmaceutically acceptable salt thereof, on a free base basis.

94. A pharmaceutical formulation for topical treatment of a skin disease, comprising (or, alternatively, a method of any one of embodiments 1-75, wherein the formulation comprises) (a) about 1.5% w/w of ruxolitinib, or a pharmaceutically acceptable salt thereof, on a free base basis, and (b) from about 0.0001% w/w to about 0.005% w/w of vitamin D3, a vitamin D3 analog, or a pharmaceutically acceptable salt thereof, on a free base basis.

95. A pharmaceutical formulation for topical treatment of a skin disease, comprising (or, alternatively, a method of any one of embodiments 1-75, wherein the formulation comprises) (a) about 0.75% w/w of ruxolitinib, or a pharmaceutically acceptable salt thereof, on a free base basis, and (b) from about 0.0001% w/w to about 0.005% w/w of vitamin D3, a vitamin D3 analog, or a pharmaceutically acceptable salt thereof, on a free base basis.

96. A pharmaceutical formulation for topical treatment of a skin disease, comprising (or, alternatively, a method of any one of embodiments 1-75, wherein the formulation comprises) (a) from about 0.75% w/w to about 1.5% w/w of ruxolitinib, or a pharmaceutically acceptable salt thereof, on a free base basis, and (b) about 0.005% w/w of vitamin D3, a vitamin D3 analog, or a pharmaceutically acceptable salt thereof, on a free base basis.

97. A pharmaceutical formulation for topical treatment of a skin disease, comprising (or, alternatively, a method of any one of embodiments 1-75, wherein the formulation comprises) (a) about 0.75% w/w of ruxolitinib, or a pharmaceutically acceptable salt thereof, on a free base basis, and (b) about 0.005% w/w of vitamin D3, a vitamin D3 analog, or a pharmaceutically acceptable salt thereof, on a free base basis.

98. A pharmaceutical formulation for topical treatment of a skin disease, comprising (or, alternatively, a method of any one of embodiments 1-75, wherein the formulation comprises) (a) about 1.5% w/w of ruxolitinib, or a pharmaceutically acceptable salt thereof, on a free base basis, and (b) about 0.005% w/w of vitamin D3, a vitamin D3 analog, or a pharmaceutically acceptable salt thereof, on a free base basis.

99. The formulation of any one of embodiments 77-98 (or, alternatively, the method of any one of embodiments 77-98), wherein the ruxolitinib, or the pharmaceutically acceptable salt thereof, is ruxolitinib phosphate.

100. The formulation of any one of embodiments 76-99 (or, alternatively, the method of any one of embodiments 76-99), wherein the vitamin D3, the vitamin D3 analog, or the pharmaceutically acceptable salt thereof, is a vitamin D3 analog, or a pharmaceutically acceptable salt thereof.

101. The formulation (or, alternatively, the method) of embodiment 100, wherein the vitamin D3 analog, or a pharmaceutically acceptable salt thereof, is selected from calcidiol, calcitriol, calcipotriol, alfacalcidol, tacalcitol, maxacalcitol, falecalcitriol, eldecalcitol, inecalcitol, seocalcitol, lexicalcitol, 20-epi-1α,25(OH)$_2$D$_3$, CD578 (17-methyl-19-nor-21-nor-23-yne-26,27-F6-1α,25(OH)$_{2D3}$), TX527 (19-nor-14,20-bisepi-23-yne-1α,25(OH)$_2$D$_3$), 2MD (2-methylene-19-nor-(20S)-1α,25(OH)$_2$D$_3$), PRI-2205 ((5E,7E)-22-ene-26,27-dehydro-1α,25(OH)$_2$D$_3$), ILX23-7553 (16-ene-23-yne-1α,25(OH)$_2$D$_3$), and MART-10(19-nor-2α-(3-hydroxypropyl)-1α,25(OH)$_2$D$_3$).

102. The formulation (or, alternatively, the method) of embodiment 100, wherein the vitamin D3 analog, or a pharmaceutically acceptable salt thereof, is calcipotriol.

103. The formulation (or, alternatively, the method) of embodiment 100, wherein the vitamin D3 analog, or a pharmaceutically acceptable salt thereof, is tacalcitol.

104. The formulation (or, alternatively, the method) of embodiment 100, wherein the vitamin D3 analog, or a pharmaceutically acceptable salt thereof, is maxacalcitol.

105. A pharmaceutical formulation for topical treatment of a skin disease, comprising (or, alternatively, a method of any one of embodiments 1-75, wherein the formulation comprises) (a) from about 0.75% w/w to about 1.5% w/w of ruxolitinib, or a pharmaceutically acceptable salt thereof, on a free base basis, and (b) about 0.005% w/w of calcipotriol.

106. A pharmaceutical formulation for topical treatment of a skin disease, comprising (or, alternatively, a method of any one of embodiments 1-75, wherein the formulation comprises) (a) about 0.75% w/w of ruxolitinib, or a pharmaceutically acceptable salt thereof, on a free base basis, and (b) about 0.005% w/w of calcipotriol.

107. A pharmaceutical formulation for topical treatment of a skin disease, comprising (or, alternatively, a method of any one of embodiments 1-75, wherein the formulation comprises) (a) about 1.5% w/w of ruxolitinib, or a pharmaceutically acceptable salt thereof, on a free base basis, and (b) about 0.005% w/w of calcipotriol.

108. The formulation (or, alternatively, the method) of any one of embodiments 105-107, wherein the ruxolitinib, or the pharmaceutically acceptable salt thereof, is ruxolitinib phosphate.

109. The formulation (or, alternatively, the method) of any one of embodiments 76-108, wherein the formulation is a cream.

110. The formulation (or, alternatively, the method) of any one of embodiments 76-108, wherein the formulation is a lotion.

111. The formulation (or, alternatively, the method) of any one of embodiments 76-110, wherein the formulation further comprises water.

112. The formulation (or, alternatively, the method) of any one of embodiments 76-111, wherein the formulation has a pH of not more than about 3.6.

113. The formulation (or, alternatively, the method) of any one of embodiments 76-111, wherein the formulation has a pH of about 2.7 to about 3.9.

114. The formulation (or, alternatively, the method) of any one of embodiments 76-111, wherein the formulation has a pH of about 2.7 to about 3.6.

115. The formulation (or, alternatively, the method) of any one of embodiments 76-111, wherein the formulation has a pH of about 4 to about 8.

116. The formulation (or, alternatively, the method) of any one of embodiments 76-115, wherein the formulation is an oil-in-water emulsion.

117. The formulation (or, alternatively, the method) of embodiment 116, wherein the oil-in-water emulsion comprises water, an oil component, and an emulsifier component.

118. The formulation (or, alternatively, the method) of embodiment 117, wherein the oil component is present in an amount of about 10% to about 40% by weight of the emulsion.

119. The formulation (or, alternatively, the method) of embodiment 117, wherein the oil component is present in an amount of about 15% to about 30% by weight of the emulsion.

120. The formulation (or, alternatively, the method) of embodiment 117, wherein the oil component is present in an amount of about 20% to about 28% by weight of the emulsion.

121. The formulation (or, alternatively, the method) of any one of embodiments 117-120, wherein the oil component comprises one or more substances independently selected from petrolatums, fatty alcohols, mineral oils, triglycerides, and silicone oils.

122. The formulation (or, alternatively, the method) of any one of embodiments 117-120, wherein the oil component comprises one or more substances independently selected from white petrolatum, cetyl alcohol, stearyl alcohol, light mineral oil, medium chain triglycerides, and dimethicone.

123. The formulation (or, alternatively, the method) of any one of embodiments 117-120, wherein the oil component comprises an occlusive agent component.

124. The formulation (or, alternatively, the method) of embodiment 123, wherein the occlusive agent component is present in an amount of about 2% to about 15% by weight of the emulsion.

125. The formulation (or, alternatively, the method) of embodiment 123, wherein the occlusive agent component is present in an amount of about 5% to about 10% by weight of the emulsion.

126. The formulation (or, alternatively, the method) of any one of embodiments 123-125, wherein the occlusive agent component comprises white petrolatum.

127. The formulation (or, alternatively, the method) of any one of embodiments 117-126, wherein the oil component comprises a stiffening agent component.

128. The formulation (or, alternatively, the method) of embodiment 127, wherein the stiffening agent component is present in an amount of about 2% to about 8% by weight of the emulsion.

129. The formulation (or, alternatively, the method) of embodiment 127, wherein the stiffening agent component is present in an amount of about 3% to about 6% by weight of the emulsion.

130. The formulation (or, alternatively, the method) of embodiment 127, wherein the stiffening agent component is present in an amount of about 4% to about 7% by weight of the emulsion.

131. The formulation (or, alternatively, the method) of any one of embodiments 127-130, wherein the stiffening agent component comprises one or more substances independently selected from fatty alcohols.

132. The formulation (or, alternatively, the method) of embodiment 131, wherein the stiffening agent component comprises one or more substances independently selected from $C_{12-20}$ fatty alcohols.

133. The formulation (or, alternatively, the method) of embodiment 131, wherein the stiffening agent component comprises one or more substances independently selected from $C_{16-18}$ fatty alcohols.

134. The formulation (or, alternatively, the method) of any one of embodiments 127-130, wherein the stiffening agent component comprises one or more substances independently selected from cetyl alcohol and stearyl alcohol.

135. The formulation (or, alternatively, the method) of any one of embodiments 117-134, wherein the oil component comprises an emollient component.

136. The formulation (or, alternatively, the method) of embodiment 135, wherein the emollient component is present in an amount of about 0.1% to about 20% by weight of the emulsion.

137. The formulation (or, alternatively, the method) of embodiment 135, wherein the emollient component is present in an amount of about 5% to about 20% by weight of the emulsion.

138. The formulation (or, alternatively, the method) of embodiment 135, wherein the emollient component is present in an amount of about 10% to about 15% by weight of the emulsion.

139. The formulation (or, alternatively, the method) of any one of embodiments 135-138, wherein the emollient component comprises one or more substances independently selected from mineral oils, triglycerides, and silicone oils.

140. The formulation (or, alternatively, the method) of any one of embodiments 135-138, wherein the emollient component comprises one or more substances independently selected from light mineral oil, medium chain triglycerides, and dimethicone.

141. The formulation (or, alternatively, the method) of any one of embodiments 117-140, wherein the water is present in an amount of about 20% to about 80% by weight of the emulsion.

142. The formulation (or, alternatively, the method) of any one of embodiments 117-140, wherein the water is present in an amount of about 35% to about 65% by weight of the emulsion.

143. The formulation (or, alternatively, the method) of any one of embodiments 117-140, wherein the water is present in an amount of about 40% to about 65% by weight of the emulsion.

144. The formulation (or, alternatively, the method) of any one of embodiments 117-143, wherein the emulsifier component is present in an amount of about 0.5% to about 15% by weight of the emulsion.

145. The formulation (or, alternatively, the method) of any one of embodiments 117-143, wherein the emulsifier component is present in an amount of about 1% to about 10% by weight of the emulsion.

146. The formulation (or, alternatively, the method) of any one of embodiments 117-143, wherein the emulsifier component is present in an amount of about 2% to about 6% by weight of the emulsion.

147. The formulation (or, alternatively, the method) of any one of embodiments 117-143, wherein the emulsifier component is present in an amount of about 3% to about 5% by weight of the emulsion.

148. The formulation (or, alternatively, the method) of any one of embodiments 117-147, wherein the emulsifier component comprises one or more substances independently selected from glyceryl fatty esters and sorbitan fatty esters.

149. The formulation (or, alternatively, the method) of any one of embodiments 117-147, wherein the emulsifier component comprises one or more substances independently selected from glyceryl stearate, and polysorbate 20.

150. The formulation (or, alternatively, the method) of any one of embodiments 117-149, wherein the emulsion further comprises a stabilizing agent component.

151. The formulation (or, alternatively, the method) of embodiment 150, wherein the stabilizing agent component is present in an amount of about 0.05% to about 5% by weight of the emulsion.

152. The formulation (or, alternatively, the method) of embodiment 150, wherein the stabilizing agent component is present in an amount of about 0.1% to about 2% by weight of the emulsion.

153. The formulation (or, alternatively, the method) of embodiment 150, wherein the stabilizing agent component is present in an amount of about 0.3% to about 0.5% by weight of the emulsion.

154. The formulation (or, alternatively, the method) of any one of embodiments 150-153, wherein the stabilizing agent component comprises one or more substances independently selected from polysaccharides.

155. The formulation (or, alternatively, the method) of any one of embodiments 150-153, wherein the stabilizing agent component comprises xanthan gum.

156. The formulation (or, alternatively, the method) of any one of embodiments 117-155, wherein the emulsion further comprises a solvent component.

157. The formulation (or, alternatively, the method) of embodiment 156, wherein the solvent component is present in an amount of about 1% to about 35% by weight of the emulsion.

158. The formulation (or, alternatively, the method) of embodiment 156, wherein the solvent component is present in an amount of about 5% to about 25% by weight of the emulsion.

159. The formulation (or, alternatively, the method) of embodiment 156, wherein the solvent component is present in an amount of about 10% to about 20% by weight of the emulsion.

160. The formulation (or, alternatively, the method) of any one of embodiments 156-159, wherein the solvent component comprises one or more substances independently selected from alkylene glycols and polyalkylene glycols.

161. The formulation (or, alternatively, the method) of any one of embodiments 156-159, wherein the solvent component comprises one or more substances independently selected from propylene glycol and polyethylene glycol.

162. A pharmaceutical formulation for topical treatment of a skin disease, comprising (a) a JAK inhibitor, or a pharmaceutically acceptable salt thereof, and (b) vitamin D3, a vitamin D3 analog, or a pharmaceutically acceptable salt thereof.

163. The pharmaceutical formulation of embodiment 162, wherein the JAK inhibitor, or a pharmaceutically acceptable salt thereof, is a JAK1/2 inhibitor, or a pharmaceutically acceptable salt thereof; and the vitamin D3, the vitamin D3 analog, or a pharmaceutically acceptable salt thereof, is a vitamin D3 analog, or a pharmaceutically acceptable salt thereof.

164. The pharmaceutical formulation of embodiment163, wherein the JAK1/2 inhibitor, or a pharmaceutically acceptable salt thereof, is ruxolitinib, or a pharmaceutically acceptable salt thereof.

165. The pharmaceutical formulation of embodiment 165, wherein the JAK1/2 inhibitor, or a pharmaceutically acceptable salt thereof, is ruxolitinib phosphate.

166. The pharmaceutical formulation of any one of embodiments 162-165, wherein the vitamin D3 analog, or a pharmaceutically acceptable salt thereof is a compound having Formula (II):

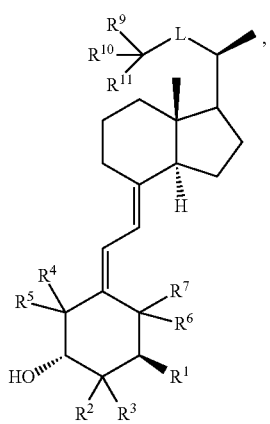

(II)

wherein:
R¹ is H or OH;
R² and R³ are each H; or
R² is O—R²·⁴; and R³ is H; or
R² and R³ are taken together to form a =CH₂ group;
R²·⁴ is —C₁₋₄ alkylene-OH;
R⁴ and R⁵ are each H; or
R⁴ and R⁵ are taken together to form a =CH₂ group;
R⁶ and R⁷ are each H; or
R⁶ and R⁷ are taken together to form a =CH₂ group;
L is —CH₂—CH₂—CH(R¹²)—, —CH₂—CH₂—CH₂—CH(R¹²)—, —CH=CH—CH(R¹²)—, —CH=CH—CH=CH—, —CH₂—C≡C—, —O—CH₂—CH₂—, or —O—CH₂—CH₂—CH₂—, wherein R¹² is H or OH;
R⁹ is C₁₋₃ alkyl or C₁₋₄ haloalkyl;
R¹⁰ is C₁₋₃ alkyl or C₁₋₄ haloalkyl;
R¹¹ is H or OH;
or, alternatively, R⁹ and R¹⁰ together with the carbon atom to which they are attached form a C₃₋₄ cycloalkyl ring; and R¹¹ is H.

167. The pharmaceutical formulation of any one of embodiments 162-166, wherein the vitamin D3 analog, or a pharmaceutically acceptable salt thereof, is calcipotriol or maxacalcitol, or a pharmaceutically acceptable salt thereof.

168. The pharmaceutical formulation of embodiment 163, wherein the JAK1/2 inhibitor is ruxolitinib, or a pharmaceutically acceptable salt thereof, and the vitamin D3 analog is calcipotriol.

169. The pharmaceutical formulation of embodiment 163, wherein the JAK1/2 inhibitor is ruxolitinib, or a pharmaceutically acceptable salt thereof, and the vitamin D3 analog is maxacalcitol.

170. The pharmaceutical formulation according to any one of embodiments 164-169, wherein the formulation comprises from about 0.05% to about 3.0% or about 0.05% to about 1.5% w/w of the ruxolitinib, or a pharmaceutically acceptable salt thereof, on a free base basis.

171. The pharmaceutical formulation according to any one of embodiments 164-169, wherein the formulation comprises about 0.05%, about 0.06%, about 0.07%, about 0.08%, about 0.09%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1.0%, about 1.05%, about 1.1%, about 1.15%, about 1.2%, about 1.25%, about 1.3%, about 1.35%, about 1.4%, about 1.45%, about 1.5%, about 1.55%, about 1.6%, about 1.65%, about 1.7%, about 1.75%, about 1.8%, about 1.85%, about 1.9%, about 1.95%, about 2.0%, about 2.5%, or about 3.0% by weight of the formulation on a free base basis of the ruxolitinib, or the pharmaceutically acceptable salt thereof.

172. The pharmaceutical formulation of any one of embodiments 163-171, wherein the formulation comprises from about 0.0001% w/w to about 0.01% w/w of the vitamin D3 analog, or a pharmaceutically acceptable salt thereof, on a free base basis.

173. The pharmaceutical formulation of any one of embodiments 163-171, wherein the formulation comprises from about 0.0001% w/w to about 0.005% w/w of the vitamin D3 analog, or a pharmaceutically acceptable salt thereof, on a free base basis.

174. The pharmaceutical formulation of any one of embodiments 163-171, wherein the formulation comprises from about 0.0001% w/w to about 0.01% w/w or from about 0.0001% w/w to about 0.005% w/w of the vitamin D3 analog, or a pharmaceutically acceptable salt thereof, on a free base basis.

175. The pharmaceutical formulation of any one of embodiments 163-171, wherein the formulation comprises about 0.005% w/w of the vitamin D3 analog, or a pharmaceutically acceptable salt thereof, on a free base basis.

176. The pharmaceutical formulation of any one of embodiments 162-175, wherein the formulation is a cream or a lotion.

177. The pharmaceutical formulation of any one of embodiments 162-176, wherein the formulation is an oil-in-water emulsion.

178. The pharmaceutical formulation of any one of embodiments 162-177, wherein the formulation comprises water, an oil component, and an emulsifier or stabilizer component.

179. The pharmaceutical formulation of embodiment 178, wherein the water comprises from about 5% to about 90%, from about 10% to about 80%, from about 10% to about 70%, from about 10% to about 60%, about 20% to about 70%, about 20% to about 60%, or from about 20% to about 50% by weight of the pharmaceutical formulation.

180. The pharmaceutical formulation of any one of embodiments 178-179, wherein the oil component comprises from about 5% to about 90%, from about 5% to about 80%, from about 5% to about 70%, from about 5% to about 60%, from about 5% to about 50%, or from about 5% to about 40% by weight of the pharmaceutical formulation.

181. The pharmaceutical formulation of any one of embodiments 178-180 wherein the emulsifier or stabilizer component comprises from about 1% to about 30% or from about 5% to about 25% by weight of the pharmaceutical formulation.

182. The pharmaceutical formulation of any one of embodiments 178-180, further comprising a solvent component for dissolving ruxolitinib, or a pharmaceutically acceptable salt thereof.

183. The pharmaceutical formulation of embodiment 182, wherein the solvent component comprises from about 5% to about 20%, from about 2% to about 30%, from about 5% to about 30%, from about 5% to about 25%, from about 5% to about 20%, or from about 10% to about 20% by weight of the pharmaceutical formulation.

184. The pharmaceutical formulation of any one of embodiments 163-183, wherein the formulation has a pH of from about 6.0 to about 8.0, from about 6.5 to about 7.5, or from about 6.5 to about 7.0.

185. The pharmaceutical formulation of embodiment 184, wherein pH of the formulation is adjusted with trolamine.

186. A method of treating a skin disease in a patient in need thereof, comprising topically administering to an affected area of the patient (a) a JAK inhibitor, or a pharmaceutically acceptable salt thereof, and (b) vitamin D3, a vitamin D3 analog, or a pharmaceutically acceptable salt thereof.

187. The method of embodiment 186, wherein the JAK inhibitor, or a pharmaceutically acceptable salt thereof, is a JAK1/2 inhibitor, or a pharmaceutically acceptable salt thereof, and the vitamin D3, the vitamin D3 analog, or a pharmaceutically acceptable salt thereof, is a vitamin D3 analog, or a pharmaceutically acceptable salt thereof.

188. The method of embodiment 187, wherein the JAK1/2 inhibitor, or a pharmaceutically acceptable salt thereof, is ruxolitinib, or a pharmaceutically acceptable salt thereof.

189. The method of embodiment 187, wherein the JAK1/2 inhibitor, or a pharmaceutically acceptable salt thereof, is ruxolitinib phosphate.

190. The method of any one of embodiments 187-189, wherein the vitamin D3 analog, or a pharmaceutically acceptable salt thereof is a compound having Formula (II):

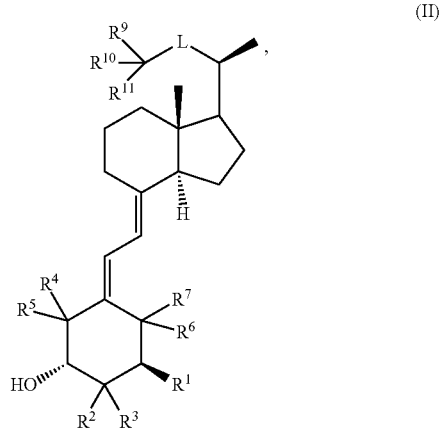

(II)

wherein:
$R^1$ is H or OH;
$R^2$ and $R^3$ are each H; or
$R^2$ is O—$R^{2\text{-}4}$; and $R^3$ is H; or
$R^2$ and $R^3$ are taken together to form a =CH$_2$ group;
$R^{2\text{-}4}$ is —C$_{1\text{-}4}$ alkylene-OH;
$R^4$ and $R^5$ are each H; or
$R^4$ and $R^5$ are taken together to form a =CH$_2$ group;
$R^6$ and $R^7$ are each H; or
$R^6$ and $R^7$ are taken together to form a =CH$_2$ group;
L is —CH$_2$—CH$_2$—CH($R^{12}$)—, —CH$_2$—CH$_2$—CH$_2$—CH($R^{12}$)—, —CH=CH—CH($R^{12}$)—, —CH=CH—CH=CH—, —CH$_2$—C≡C—, —O—CH$_2$—CH$_2$—, or —O—CH$_2$—CH$_2$—CH$_2$—, wherein $R^{12}$ is H or OH;
$R^9$ is C$_{1\text{-}3}$ alkyl or C$_{1\text{-}4}$ haloalkyl;
$R^{10}$ is C$_{1\text{-}3}$ alkyl or C$_{1\text{-}4}$ haloalkyl;
$R^{11}$ is H or OH;
or, alternatively, $R^9$ and $R^{10}$ together with the carbon atom to which they are attached form a C$_{3\text{-}4}$ cycloalkyl ring; and $R^{11}$ is H.

191. The method of any one of embodiments 187-189, wherein the vitamin D3 analog, or a pharmaceutically acceptable salt thereof is calcipotriol or maxacalcitol, or a pharmaceutically acceptable salt thereof.

192. The method of embodiment 187, wherein the JAK1/2 inhibitor is ruxolitinib, or a pharmaceutically acceptable salt thereof, and the vitamin D3 analog is calcipotriol.

193. The method of embodiment 187, wherein the JAK1/2 inhibitor is ruxolitinib, or a pharmaceutically acceptable salt thereof, and the vitamin D3 analog is maxacalcitol.

194. The method of any one of embodiments 187-193, the skin disease is an autoimmune or an inflammatory skin disease.

195. The method of any one of embodiments 187-193, wherein the skin disease is a Th1 or Th17 associated skin disease.

196. The method of any one of embodiments 187-193, wherein the skin disease is mediated by interleukin 22 (IL-22), C-X-C motif chemokine 10 (CXCL10), matrix metallopeptidase 12 (MMP12), or a combination thereof.

197. The method of any one of embodiments 187-193, wherein the skin disease is mediated by Defb4, S100a12, or Serpinb4.

198. The method of any one of embodiments 187-193, wherein the skin disease is mediated by filaggrin/FLG, Loricin/LOR, IL-31, TSLP, CAMP, CCL17, CCL22, DefB4a, interferon-gamma, IL-17A, IL-17F, IL-22, IL-33, IL-4, or TNFSF18.

199. The method of any one of embodiments 187-193, wherein the skin disease is selected from psoriasis, atopic dermatitis, alopecia, vitiligo, Reiter's syndrome, pityriasis rubra pilaris, epidermolysis bullosa simplex, palmoplantar keratoderma, pachyonychia congenita, steatocystoma multiplex, cutaneous lichen planus, cutaneous T-cell lymphoma, hidradenitis suppurativa, contact dermatitis, and ichthyosis.

200. The method of any one of embodiments 187-193, wherein the skin disease is rosacea, psoriatic arthritis, dermal fibrosis, morphea, spitz nevi, dermatophytosis, or acne vulgaris.

201. The method of any one of embodiments 187-200, wherein there is a synergistic effect between the JAK1/2 inhibitor, or the pharmaceutically acceptable salt thereof, and the vitamin D3 analog, or the pharmaceutically acceptable salt thereof.

202. The method of any one of embodiments 187-201, wherein (a) the JAK1/2 inhibitor, or the pharmaceutically acceptable salt thereof, and (b) the vitamin D3 analog, or a pharmaceutically acceptable salt thereof, are administered at least one time per day.

203. The method of any one of embodiments 187-201, wherein (a) the JAK1/2 inhibitor, or the pharmaceutically acceptable salt thereof, and (b) the vitamin D3 analog, or a pharmaceutically acceptable salt thereof, are administered at least two times per day.

204. The method of any one of embodiments 187-203, wherein (a) the JAK1/2 inhibitor, or the pharmaceutically acceptable salt thereof, and (b) the vitamin D3 analog, or a pharmaceutically acceptable salt thereof, are administered simultaneously.

205. The method of any one of embodiments 187-203, wherein (a) the JAK1/2 inhibitor, or the pharmaceutically acceptable salt thereof, and (b) the vitamin D3 analog, or a pharmaceutically acceptable salt thereof, are administered sequentially.

206. The method of any one of embodiments 187-205, wherein (a) the JAK1/2 inhibitor, or the pharmaceutically acceptable salt thereof, and (b) the vitamin D3 analog, or the pharmaceutically acceptable salt thereof, are administered as separate formulations.

207. The method of any one of embodiments 187-204, wherein (a) the JAK1/2 inhibitor, or the pharmaceutically acceptable salt thereof, and (b) the vitamin D3 analog, or the pharmaceutically acceptable salt thereof, are administered in a single formulation.

208. The method of embodiment 206, wherein the JAK1/2 inhibitor, or a pharmaceutically acceptable salt thereof, and the vitamin D3 analog, or the pharmaceutically acceptable salt thereof, are each administered in a topical formulation.

209. The method of embodiment 207, wherein the JAK1/2 inhibitor, or a pharmaceutically acceptable salt thereof, and the vitamin D3 analog, or the pharmaceutically acceptable salt thereof, are administered in a single topical formulation.

210. The method of embodiment 208, wherein each topical formulation is an ointment, a cream, or a lotion.

211. The method of embodiment 209, wherein the single topical formulation is an ointment, a cream, or a lotion.

212. The method of embodiment 211, wherein the single topical formulation is a cream or a lotion.

213. The method of embodiment 211, wherein the single topical formulation is a cream formulation.

214. The method of any one of embodiments 211-213, wherein the single topical formulation has a pH of from about 6.0 to about 8.0, from about 6.5 to about 7.5, or from about 6.5 to about 7.0.

215. The method of any one of embodiments 187-214, further comprising administering an additional therapeutic agent.

216. The method of embodiment 215, wherein the additional therapeutic agent is a corticosteroid.

217. The method of embodiment 216, wherein the corticosteroid is betamethasone dipropionate.

EXAMPLES

The presently claimed subject matter will be described in greater detail by way of specific examples. The following examples are offered for illustrative purposes, and are not intended to limit the presently claimed subject matter in any manner. Those of skill in the art will readily recognize a variety of non-critical parameters, which can be changed or modified to yield essentially the same results.

All statistical analysis of in vitro experiments were performed with GraphPad prism software (version 7) using Kruskal-Wallis-Test and Mann-Whitney U test. Gene expression was analyzed with Partek Flow genomic analysis software and Subio Platform software v1.22.5266 using Welch's t-test. Confidence intervals were determined at 95%. P<0.05 was considered to be "significant" (*), p<0.01 to be "highly significant" (**). KEGG pathways were mapped to differentially expressed genes using DAVID v6.8 (Database for Annotation, Visualization and Integrated Discovery).

Example 1. In Vitro JAK Kinase Assay

JAK1 inhibitors that can be used for the treatment of cytokine-related diseases or disorders are tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) with an N-terminal His tag are expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). $IC_{50}$s of compounds are measured for each kinase in the 40 µL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM $IC_{50}$ measurements, ATP concentration in the reactions is 1 mM. Reactions are carried out at room temperature for 1 hour and then stopped with 20 µL 45 mM EDTA, 300 nM SA-APC, 6 nM Eu-Py20 in assay buffer (Perkin Elmer, Boston, MA). Binding to the Europium labeled antibody takes place for 40 minutes and HTRF signal was measured on a Fusion plate reader (Perkin Elmer, Boston, MA). The compounds in Table 1 were tested in this assay and shown to have the $IC_{50}$ values in Table 1.

Example 2: Ex Vivo Skin Pharmacodynamics Experiment on the Combination of a JAK Inhibitor and a Vitamin D3 Analog Materials and Methods The pharmacodynamics assay described in the present disclosure involves a similar paradigm to elicit a Th1, Th2 and Th17 responses as the one to elicit a TH17 response published by Susan H. Smith, et al., Development of a Topical Treatment for Psoriasis Targeting RORγ: From Bench to Skin. PlosOne. Published: February 2016, which is incorporated by reference in its entirety. This paradigm was used to evaluate the therapeutic potential of the active compounds in topical formulations for dermatological diseases (i.e. psoriasis, vitiligo, and alopecia).

Figure 4:
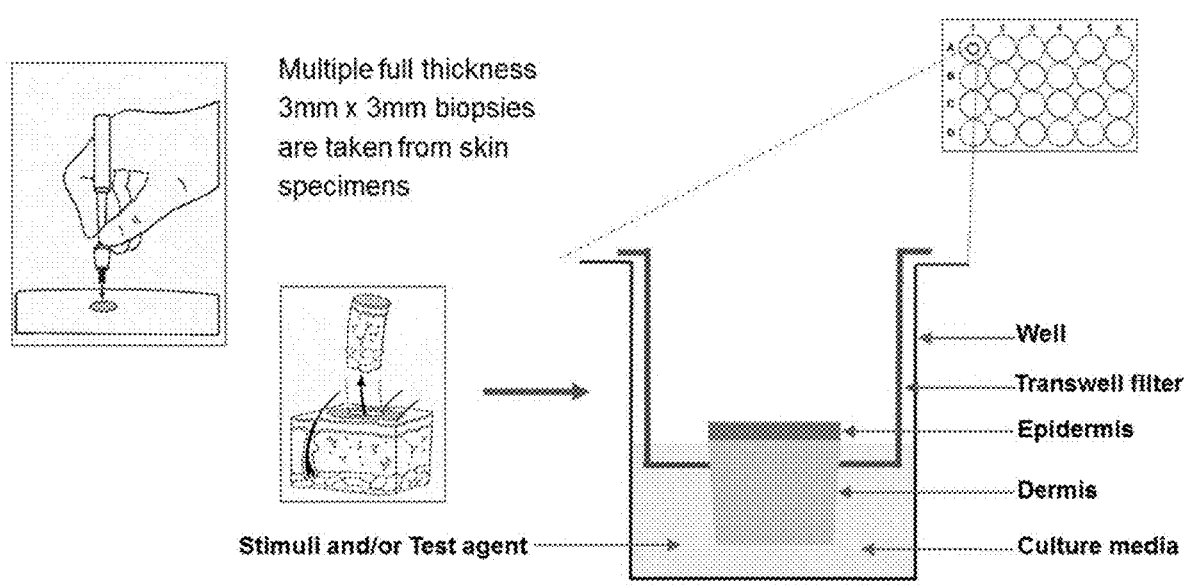
FIG. 4 depicts a schematic representation of a Transwell® insert.

Freshly excised healthy human skin from cosmetic reduction surgery can be dermatomed to an approximate thickness of 750±100 µm using an Integra® dermatome. The dermatomed skin is then be further sectioned into 7 mm biopsies for basolateral or topical dosing, careful to avoid areas of variable thickness or striation. The biopsies are placed into 6.5 mm permeable membrane Transwell® inserts for basolateral or topical dosing. Human skin are placed into Transwell® inserts, Stratum corneum side apical, with a small volume of collagen between the basal dermal tissue and the permeable membrane. A schematic representation of a Transwell® insert is shown in FIG. 4. A full-scale experiment was performed with 8 individual skin donors, n=4 for basolateral dosing; or 2 individual skin donors for topical dosing. One donor can be utilized per combination of the JAK inhibitor and the vitamin D3 analog at desired concentrations according to Method A for basolateral dosing or Method B for topical dosing.

Method A (Basolateral Dosing)
- (i) Transwell® permeable inserts (n=4 per treatment), with an average surface area of approximately 0.33 cm² and a volume of 0.5 mL are employed.
- (ii) Skin prepared as described herein are placed into the Transwell® inserts, Stratum corneum side apical, with a small volume of collagen between the basal dermal tissue and the permeable membrane.
- (iii) The basal chambers are filled with 0.5 mL of culture media and drug (the JAK inhibitor and/or the vitamin D3 analog) added to the media at the designated final concentration to pre-treat in a humidified incubator overnight at 37° C. (ca. 16 hours).
- (iv) The next day, the contents of the basal chambers from each insert were vacuum aspirated and replaced with 0.5 mL of pre-warmed (ca. 37° C.) Cornification media containing test compound and fresh stimulation cocktail.
- (v) Cultures can be stored in a humidified incubator with a temperature of 37° C.
- (vi) Tissue explants can be harvested at 24 hours post stimulation. Half of tissue are placed in RNALater to assay cytokine production by RT-qPCR.
- (vii) Tissue homogenization: tissue tubes were placed in Omni homogenizer and run at 3 cycles for 30 sec at 5 m/s with a 10 sec dwell setting. The homogenization was repeated 4 times for a total of 12 cycles with 1 min and 30 seconds on ice between each run to cool sample. After final run, the tissue tubes cooled on ice for the same duration of time.

(viii) RT-PCR was ran on the samples in duplicate on the Applied Biosystems Quant 6 standard RT-qPCR program with a 40 cycle threshold, utilizing GAPDH as a housekeeping gene.

Appropriate concentrations for the JAK inhibitor and the vitamin D3 analog can be determined based on the $IC_{50}$ of the compounds. For example, the JAK inhibitor, ruxolitinib, has an $IC_{50}$ of 50 nM for inhibiting IL-23 stimulated IL-22 production in human T-cells and an IC50 of 281 nM in a human whole blood TPO induced STAT3 phosphorylation assay (Fridman, et al., *J Invest Dermatol*, 2011 September; 131(9):1838-44 (PMID: 21677670); and Fridman, et al., *J Immunol*, 2010 May 1; 184(9):5298-307 (PMID: 20363976). Similarly, tacalcitol, calcipotriol, and maxacalcitol decreased keratinocyte cell line proliferation in a concentration-dependent manner with $IC_{50}$s of about 10-100 nM (Takahasi, et al., *J Dermatol Sci*, 2003 February; 31(1): 21-8 (PMID: 12615360)). Concentrations below (down to 0) and above the $IC_{50}$ concentrations can be used for the JAK inhibitor (e.g., ruxolitinib, delgocitinib, etc.) and the vitamin D3 analog (e.g., tacalcitol, calcipotriol, and maxacalcitol).

Method B (Topical Dosing)

(i) Transwell® permeable inserts (n=4 per treatment), with an average surface area of approximately 0.33 cm² and a volume of 0.5 mL are employed.

(ii) Skin prepared as described herein are placed into the Transwell® inserts, Stratum corneum side basolateral, with a small volume of collagen between the basal dermal tissue and the permeable membrane.

(iii) The basal chambers are filled with 0.5 mL of culture media. Drug (the JAK inhibitor and/or the vitamin D3 analog) applied topically to the apical side of dermatomed skin (~18 ul/cm²) to pre-treat for 16 or 24 hr, in a humidified incubator overnight at 37° C.

(iv) The next day, the contents of the basal chambers from each insert were vacuum aspirated. Media replaced with 0.5 mL of pre-warmed (ca. 37° C.) cornification media containing fresh stimulation cocktail.

(v) Cultures can be stored in a humidified incubator with a temperature of 37° C.

(vi) Tissue explants can be harvested at 24 hours post stimulation. Half of tissue are placed in RNALater to assay cytokine production by RT-qPCR.

(vii) Tissue homogenization: tissue tubes were placed in Omni homogenizer and run at 3 cycles for 30 sec at 5 m/s with a 10 sec dwell setting. The homogenization was repeated 4 times for a total of 12 cycles with 1 min and 30 seconds on ice between each run to cool sample. After final run, the tissue tubes cooled on ice for the same duration of time.

(viii) RT-PCR was ran on the samples in duplicate on the Applied Biosystems Quant 6 standard RT-qPCR program with a 40 cycle threshold, utilizing GAPDH as a housekeeping gene.

Ruxolitinib and Calcipotriol—Basolateral Dosing (Method A)

Experiments were carried out as described above in the Materials and Methods (Method A) section of Example 2 for ruxolitinib phosphate and calcipotriol. A list of the treatment conditions for donors 2 and 3 with stimulation for Th1 or Th17 with addition of ruxolitinib phosphate (calculated on a free base basis) and/or calcipotriol are as shown in Table 2 and 3, respectively.

TABLE 2

Donor 2

| | Calcipotriol (nM) | Ruxolitinib (nM) | Stimulation |
|---|---|---|---|
| a | 0 | 0 | No |
| b | 0 | 0 | Th1 |
| c | 2250 | 0 | Th1 |
| d | 750 | 0 | Th1 |
| e | 250 | 0 | Th1 |
| f | 83.3 | 0 | Th1 |
| g | 27.8 | 0 | Th1 |
| h | 0 | 500 | Th1 |
| i | 0 | 166.7 | Th1 |
| j | 0 | 55.6 | Th1 |
| k | 0 | 18.5 | Th1 |
| l | 2250 | 500 | Th1 |
| m | 2250 | 18.5 | Th1 |
| n | 750 | 166.7 | Th1 |
| o | 750 | 55.6 | Th1 |
| p | 250 | 166.7 | Th1 |
| q | 250 | 55.6 | Th1 |
| r | 83.3 | 166.7 | Th1 |
| s | 83.3 | 55.6 | Th1 |
| t | 27.8 | 500 | Th1 |

TABLE 3

Donor 3

| | Calcipotriol (nM) | Ruxolitinib (nM) | Stimulation |
|---|---|---|---|
| a | 0 | 0 | No |
| b | 0 | 0 | Th17 |
| c | 2250 | 0 | Th17 |
| d | 750 | 0 | Th17 |
| e | 250 | 0 | Th17 |
| f | 83.3 | 0 | Th17 |
| g | 27.8 | 0 | Th17 |
| h | 0 | 500 | Th17 |
| i | 0 | 166.7 | Th17 |
| j | 0 | 55.6 | Th17 |
| k | 0 | 18.5 | Th17 |
| l | 2250 | 500 | Th17 |
| m | 2250 | 18.5 | Th17 |
| n | 750 | 166.7 | Th17 |
| o | 750 | 55.6 | Th17 |
| p | 250 | 166.7 | Th17 |
| q | 250 | 55.6 | Th17 |
| r | 83.3 | 166.7 | Th17 |
| s | 83.3 | 55.6 | Th17 |
| t | 27.8 | 500 | Th17 |

Note:
After solubilizing each of the test compounds in 100% DMSO at 1000x, the stocks were stored at −20° C.

Figure 2:
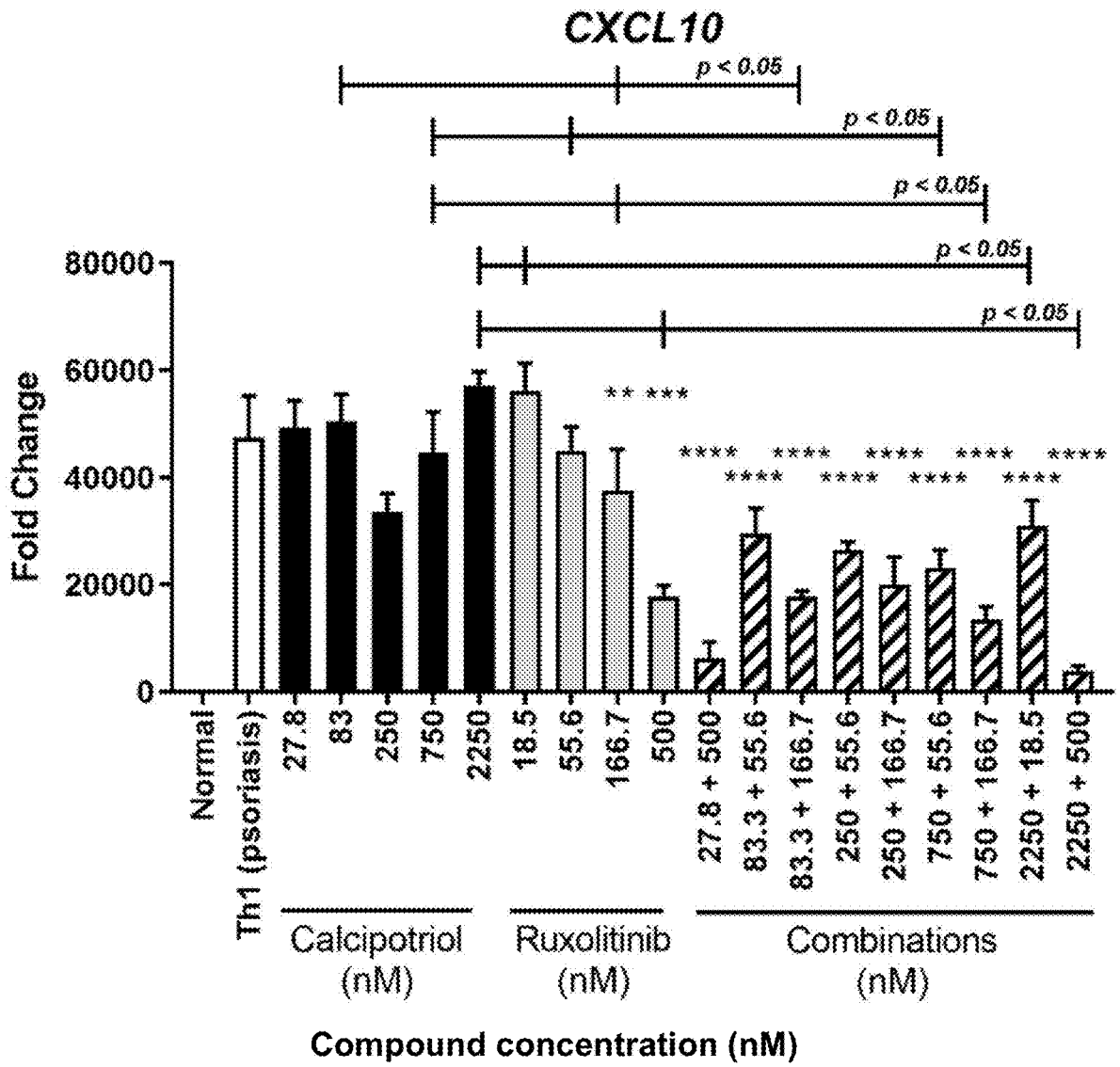
FIG. 2 depicts fold changes and p-values of CXCL10 levels of the skins treated basolaterally with various concentrations of ruxolitinib, calcipotriol, and a combination of thereof at 24 hours following stimulation over normal (healthy) unstimulated and stimulated human skins.
Figure 3:
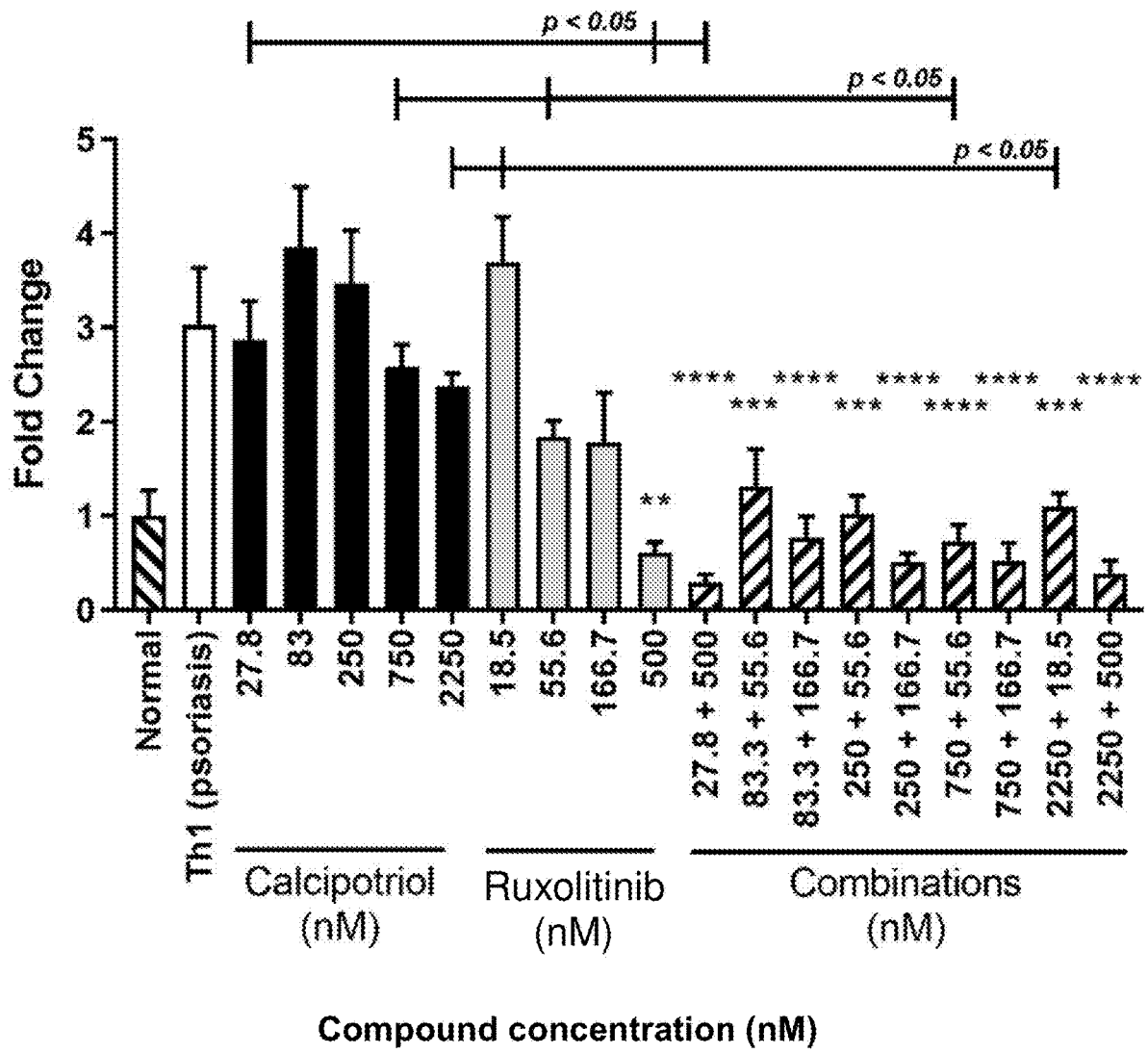
FIG. 3 depicts fold changes and p-values of MMP12 levels of the skins treated basolaterally with various concentrations of ruxolitinib, calcipotriol, and a combination of thereof at 24 hours following stimulation over normal (healthy) unstimulated and stimulated human skins.

The levels of biomarkers such as IL-22, CXCL10, and MMP12 with regard to the test compounds and combinations thereof were quantified and fold changes in gene expression were calculated against untreated control. Unexpectedly and surprisingly, combinations of calcipotriol and ruxolitinib showed synergistic effects in decreasing the levels of IL-22, CXCL10, and MMP12, as shown in FIG. 1-3. For example, the tested combinations significantly decreased the IL-22 level and such decreasing effect is statistically significant. The tested combinations also effectively decreased the CXCL10 level and such decreasing effect is statistically significant. The tested combinations effectively decreased the MMP12 level and such decreasing effect is statistically significant. These results are unexpected and surprising for several reasons. One reason is that it is commonly known in the art that the major source of vitamin D in humans is the cutaneous synthesis in the presence of sunlight and, to date, the anti-inflammatory efficacy of JAK inhibitors on skin diseases has not been associated to geographic location or sunlight exposure. Another reason is that the clinical efficacy of vitamin D3 analogues is thought to be primarily driven by their ability to normalize keratinocyte hyperproliferation and modulation of epidermal differentiation and these mechanisms are independent of inflammatory cytokines utilizing the JAK pathway. See, Hu et al. "Reciprocal role of vitamin D receptor on β-catenin regulated keratinocyte proliferation and differentiation" J Steroid Biochem Mol Biol. 2014 October; 144 Pt A:237-41, PMID: 24239508, which is incorporated by reference in its entirety herein. Moreover, a recent study on psoriasis shows that the skin biopsies from psoriasis patients treated with topical calcipotriol demonstrate a significant decrease in CD8(+) IL-17(+) T cells but there was no changes in the frequency of IL-22(+) or IFN-γ(+) cells in psoriasis lesions. See, Dyring-Andersen et al. "The Vitamin D Analogue Calcipotriol Reduces the Frequency of CD8+ IL-17+ T Cells in Psoriasis Lesions. Scand J Immunol" 2015 July; 82(1):84-91, PMID: 25904071, which is incorporated by reference in its entirety herein. Therefore, it is unexpected and surprising to find the synergistic effect between calcipotriol and ruxolitinib in decreasing the levels of IL-22, CXCL10, and MMP12.

Additionally, the levels of other gene markers were also quantified with respect to the test compounds (ruxolitinib and calcipotriol) and combinations thereof. Absolute fold changes in gene expression were calculated against untreated control. FIG. 6A-6B shows that combinations of calcipotriol and ruxolitinib caused >2 or >4 absolute fold changes in certain genes as compared to untreated control (white indicates <2 absolute fold change, grey indicates >2 absolute fold change, and black indicates >4 absolute fold change). Of the genes having the highest absolute fold change, barrier function genes (filaggrin/FLG and Loricin/LOR) are involved in many dermatology diseases; IL-31 and TSLP are involved in itch, prevalent in many dermatology diseases, and CAMP and DefB4 are antimicrobial peptides with involvement of skin diseases with barrier disruptions (that can increase infection).

Ruxolitinib and Maxacalcitol—Basolateral Dosing (Method A)

Experiments were carried out as described above in the Materials and Methods (Method A) section of Example 2 for ruxolitinib phosphate and maxacalcitol. A list of the treatment conditions for donors 2 and 3 with stimulation for Th1 or Th17 with addition of ruxolitinib phosphate (calculated on a free base basis) and/or maxacalcitol are as shown in Tables 4 and 5, respectively.

TABLE 4

| | Ruxolitinib (nM) | Maxacalcitol (nM) | Stimulation |
|---|---|---|---|
| a | 0 | 0 | No |
| b | 0 | 0 | Th1 |
| c | 18.519 | 0 | Th1 |
| d | 6.173 | 0 | Th1 |
| e | 0 | 0 | Th1 |
| f | 0 | 0 | Th1 |
| g | 0 | 540 | Th1 |
| h | 0 | 0 | Th1 |
| i | 18.519 | 0 | Th1 |
| j | 18.519 | 0 | Th1 |
| k | 18.519 | 240 | Th1 |

TABLE 4-continued

| | Ruxolitinib (nM) | Maxacalcitol (nM) | Stimulation |
|---|---|---|---|
| l | 18.519 | 0 | Th1 |
| m | 6.173 | 0 | Th1 |
| n | 6.173 | 0 | Th1 |
| o | 6.173 | 240 | Th1 |
| p | 6.173 | 0 | Th1 |

TABLE 5

| | Ruxolitinib (nM) | Ntmumlcitol (nM) | Stimulation |
|---|---|---|---|
| a | 0 | 0 | No |
| b | 0 | 0 | Th17 |
| c | 18.519 | 0 | Th17 |
| d | 6.173 | 0 | Th17 |
| e | 0 | 0 | Th17 |
| f | 0 | 0 | Th17 |
| g | 0 | 540 | Th17 |
| h | 0 | 0 | Th17 |
| i | 18.519 | 0 | Th17 |
| j | 18.519 | 0 | Th17 |
| k | 18.519 | 240 | Th17 |
| l | 18.519 | 0 | Th17 |
| m | 6.173 | 0 | Th17 |
| n | 6.173 | 0 | Th17 |
| o | 6.173 | 240 | Th17 |
| p | 6.173 | 0 | Th17 |

Note:
After solubilizing each of the test compounds in 100% DMSO at 1000x, the stocks were stored at −20° C.

Figure 7A:
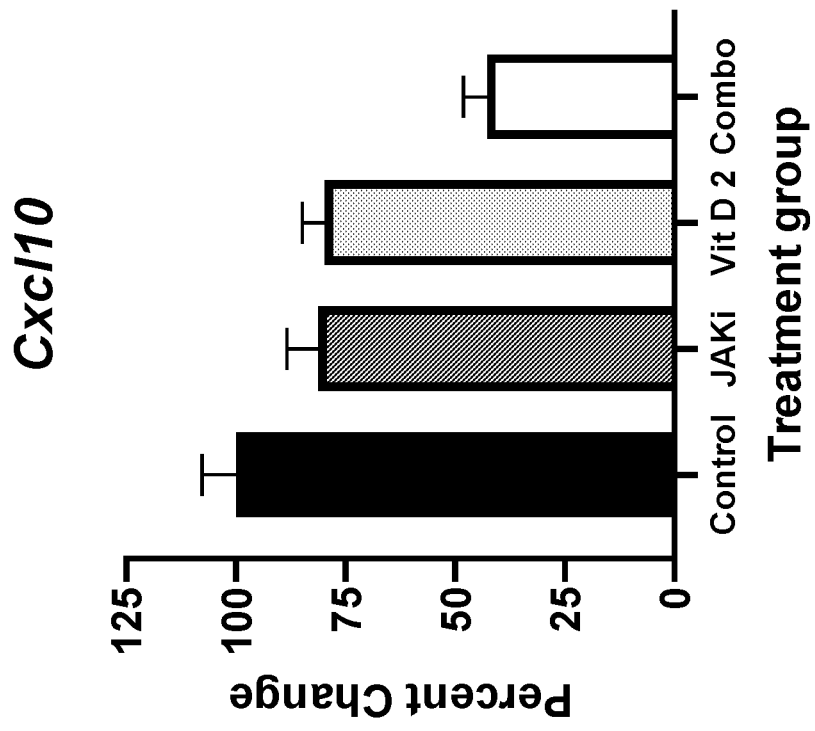
FIGS. 7A-7B depict fold changes (with mean+SEM) of IL-22 levels and CXCL10, respectively of the skins treated basolaterally with various concentrations of ruxolitinib, maxacalcitol, and a combination of thereof at 24 hours following stimulation over normal (healthy) unstimulated and stimulated human skins (JAKi is ruxolitinib; Vit D is maxacalcitol).
Figure 7B:
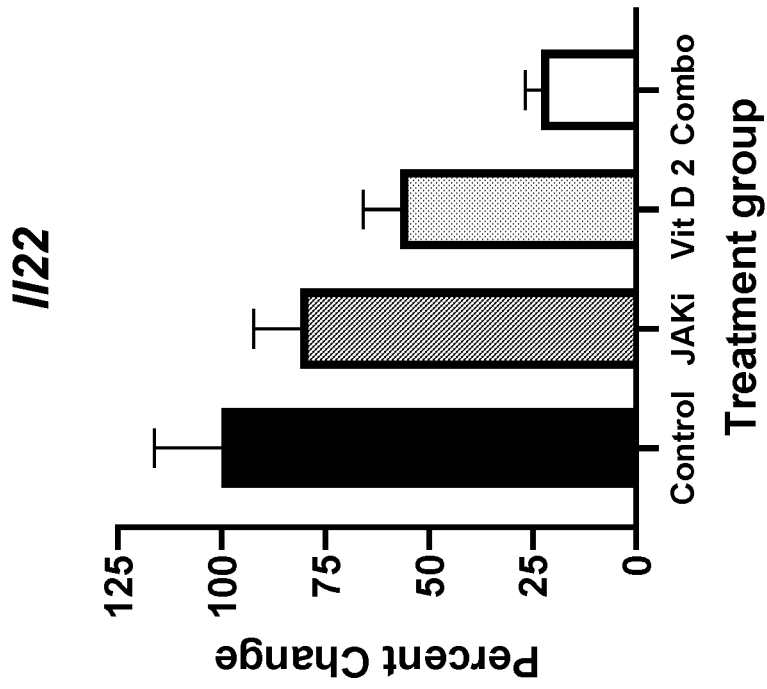

The levels of biomarkers such as IL-22 and CXCL10 with regard to the test compounds and combinations thereof were quantified and fold changes in gene expression were calculated against untreated control. Unexpectedly and surprisingly, combinations of maxacalcitol and ruxolitinib showed synergistic effects in decreasing the levels of IL-22 and CXCL10, as shown in FIG. 7A-7B.

Ruxolitinib and Calcipotriol—Topical Dosing (Method B)

Aqueous based solutions of ruxolitinib phosphate and calcipotriol, alone and in combination (see Table 6), were prepared using ruxolitinib phosphate and calcipotriol according to the following procedure:

(i) BHT was initially added to the Transcutol P in an amber Duran and stirred at 500 RPM until visually homogenous.

(ii) The solution from Step (i) was added to the rest of the polar phase excipients in an amber Duran and stirred by magnetic stirrer bar at 500 RPM until visually homogenous.

(iii) Ruxolitinib phosphate was added to the polar phase from Step (ii) and stirred for 5 mins at 500 RPM, ruxolitinib phosphate does not fully dissolve in this step.

(iv) The suspension from Step (iii) was pH adjusted to pH 6.5-7.0 with Trolamine, and the ruxolitinib phosphate dissolved during this step.

(v) Calcipotriol monohydrate was added to the polar phase from Step (iv) and stirred at 500 RPM at 65° C. for 1 hour, then at ambient laboratory temperature overnight, to dissolve.

(vi) Quantity sufficient with water to 100%.

TABLE 6

| Component | Vehicle | Ruxolitinib 1.5% w/w + Calcipotriol 0.005% (w/w) | Ruxolitinib 0.75% w/w + Calcipotriol 0.005% (w/w) | Calcipotriol 0.005% (w/w) | Ruxolitinib 1.5% (w/w) | Ruxolitinib 0.75% (w/w) |
|---|---|---|---|---|---|---|
| Ruxolitinib phosphate | — | 1.982 | 0.99 | — | 1.982 | 0.99 |
| Calcipotriol monohydrate | — | 0.0052 | 0.0052 | 0.0052 | — | — |
| Water | 57.00 | 55.00 | 56.00 | 57.00 | 55.00 | 56.00 |
| Transcutol P | 27.50 | 27.50 | 27.50 | 27.50 | 27.50 | 27.50 |
| PEG 400 | 6.50 | 6.50 | 6.50 | 6.50 | 6.50 | 6.50 |
| Phenoxyethanol | 1.00 | 1.00 | 1.00 | 1.00 | 1.00 | 1.00 |
| BHA | 0.05 | 0.05 | 0.05 | 0.05 | 0.05 | 0.05 |
| Polyoxyl 35 castor oil | 5.30 | 5.30 | 5.30 | 5.30 | 5.30 | 5.30 |
| Phosphoric Acid | To pH 6.5-7.0 | To pH 6.5-7.0 | To pH 6.5-7.0 | To pH 6.5-7.0 | To pH 6.5-7.0 | To pH 6.5-7.0 |
| Trolamine | | | | | | |
| 2$^{nd}$ addition of water | Q.S. | Q.S. | Q.S. | Q.S. | Q.S. | Q.S. |
| Total | 100.00 | 100.00 | 100.00 | 100.00 | 100.00 | 100.00 |

The aqueous solutions shown in Table 6 were tested as described above in the Materials and Methods (Method B) section of Example 2 for ruxolitinib phosphate and calcipotriol. A list of the treatment conditions for donors 1 and 2 with stimulation for Th1 or Th17 with addition of ruxolitinib phosphate (calculated on a free base basis) and/or calcipotriol are as shown in Tables 7 and 8, respectively.

TABLE 7

Donor 1

| | Ruxolitinib (w/w/) | Calcipotriol (w/w/) | Stimulation | Pre-treatment time |
|---|---|---|---|---|
| a | 0 | 0 | No | 16 hr |
| b | 0 | 0 | Th1 | 16 hr |
| c | 1.5% | 0 | Th1 | 16 hr |
| d | 0.75% | 0 | Th1 | 16 hr |
| e | 0 | 0.005% | Th1 | 16 hr |
| f | 0 | 0.005% | Th1 | 16 hr |
| g | 1.5% | 0.005% | Th1 | 16 hr |
| h | 0.75% | 0.005% | Th1 | 16 hr |
| i | 0 | 0 | No | 24 hr |
| j | 0 | 0 | Th1 | 24 hr |
| k | 1.5% | 0 | Th1 | 24 hr |
| l | 0.75% | 0 | Th1 | 24 hr |
| m | 0 | 0.005% | Th1 | 24 hr |
| n | 0 | 0.005% | Th1 | 24 hr |
| o | 1.5% | 0.005% | Th1 | 24 hr |
| p | 0.75% | 0.005% | Th1 | 24 hr |

TABLE 8

Donor 2

| | Ruxolitinib (w/w/) | Calcipotriol (w/w/) | Stimulation | Pre-treatment time |
|---|---|---|---|---|
| a | 0 | 0 | No | 16 hr |
| b | 0 | 0 | Th17 | 16 hr |
| c | 1.5% | 0 | Th17 | 16 hr |
| d | 0.75% | 0 | Th17 | 16 hr |
| e | 0 | 0.005% | Th17 | 16 hr |
| f | 0 | 0.005% | Th17 | 16 hr |
| g | 1.5% | 0.005% | Th17 | 16 hr |
| h | 0.75% | 0.005% | Th17 | 16 hr |
| i | 0 | 0 | No | 24 hr |
| j | 0 | 0 | Th17 | 24 hr |
| k | 1.5% | 0 | Th17 | 24 hr |
| l | 0.75% | 0 | Th17 | 24 hr |
| m | 0 | 0.005% | Th17 | 24 hr |
| n | 0 | 0.005% | Th17 | 24 hr |
| o | 1.5% | 0.005% | Th17 | 24 hr |
| p | 0.75% | 0.005% | Th17 | 24 hr |

The levels of biomarkers such as S100a12, Defb4, Serpinb4, MMP12, IL-22, and CXCL10 with regard to the test compounds and combinations thereof were quantified and fold changes in gene expression were calculated against untreated control (FIG. 8A-8C and FIG. 9A-9C). Unexpectedly and surprisingly, calcipotriol and ruxolitinib combined in a topically applied aqueous based solution showed synergistic effects in decreasing the levels of S100a12, Defb4, Serpinb4, and MMP12 as shown in FIG. 8A-8C and FIG. 9A. S100a12 is a significant marker for psoriasis disease activity (Wilsmann-Theis, D, et al., J Eur Acad Dermatol Venereol, 30(7):1165-70 (2016); doi: 10.1111/jdv.13269). Defb4 encodes human beta-defensin 2(hBD2), an antimicrobial peptide that plays an essential role in inflammatory processes in the skin and is important in the pathogenesis of psoriasis (Johansen C, et al., J Invest Derm, 136(8):1608-1616 (2016); doi: 10.1016/j.jid.2016.04.012). Serpinb4 contributes to inflammation in patients with chronic skin diseases, including atopic dermatitis (Sivaprasad, U, et al., J Invest Derm 135(1):160-169 (2015); DOI:10.1038/jid.2014.353). These results are unexpected and surprising for several reasons. One reason is that it is commonly known in the art that the major source of vitamin D in humans is the cutaneous synthesis in the presence of sunlight and, to date, the anti-inflammatory efficacy of JAK inhibitors on skin diseases has not been associated to geographic location or sunlight exposure. Another reason is that the clinical efficacy of vitamin D3 analogues is thought to be primarily driven by their ability to normalize keratinocyte hyperproliferation and modulation of epidermal differentiation and these mechanisms are independent of inflammatory cytokines utilizing the JAK pathway. Therefore, it is unexpected and surprising to find the synergistic effect between calcipotriol and ruxolitinib in decreasing the levels of S100a12, Defb4, Serpinb4 and MMP12. The calcipotriol and ruxolitinib combined in a topically applied aqueous based solution also decreased the gene expression of IL-22 and CXCL10 (FIG. 9B-9C); however, the high level of ruxolitinib in the aqueous solutions (0.75% and 1.5%) also had a strong effect on gene expression, making it difficult to assess synergy in the topical application although such synergy is seen at lower concentrations in the basolateral application (Method A).

Example 3: Methods for Preparations of Ruxolitinib Creams and for Preparations of Ruxolitinib and Calcipotriol Combination Creams Methods for preparations of ruxolitinib creams (Formulations #1, #2, #4, and #5) containing 1.5% w/w of ruxolitinib on a free base basis and preparations of ruxolitinib and calcipotriol combination creams (Formulations #3 and #6) containing 1.5% w/w of ruxolitinib on a free base basis and 50 microgram/g of calcipotriol are described herein.

For preparations of ruxolitinib and calcipotriol combination creams, ruxolitinib was incorporated in the water phase, and calcipotriol was first dissolved in medium chain triglycerides, and then added into the oil-in-water emulsion. Details of the preparation steps are as follows:

1. Preparation of a 1 mg/g calcipotriol solution in medium chain triglycerides. calcipotriol was dissolved in medium chain triglycerides at 1 mg/g via heating at about 60° C. When calcipotriol was fully dissolved, the heating was stopped. The resulting stock solution was covered with aluminum foil to avoid light.

2. Preparation of an aqueous phase. Purified water, disodium EDTA, low molecular weight PEG, and ruxolitinib phosphate were mixed altogether according to their respective weight percentages as described in Table 10 and the resulting mixture was heated at about 55° C. to about 60° C. while stirring to dissolve disodium EDTA and ruxolitinib to form an aqueous phase.

3. Preparation of a paraben phase. Methylparaben and propylparaben were added into propylene glycol according to their respective weight percentages as described in Table 10 to form a mixture. The resulting mixture was heated at about 55° C. to about 60° C. while stirring to dissolve the methylparaben and propylparaben to form a paraben phase.

4. Preparation of the xanthan gum phase. Xanthan gum was mixed with propylene glycol according to the respective weight percentages described in Table 10 and the resulting mixture was heated at about 55° C. to about 60° C. to form a Xanthan gum phase in a form of dispersion.

5. Preparation of the oil phase. White petrolatum, light mineral oil, glycerol stearate SE, cetyl alcohol, stearyl alcohol, dimethicone, medium chain triglycerides, and polysorbate 20 were mixed according to the respective weight percentages described in Table 10 and the resulting mixture was heated to about 65° C. to about 68° C. while stirring till all of the excipients were melt to form an oil phase.

6. The aqueous phase was heated to about 65° C. to about 68° C., while stirring at about 600-800 rpm.

7. Into the heated aqueous phase was transferred the paraben phase according to the percentage described in Table 10 and the resulting mixture was well stirred and maintained at about 65° C. to about 68° C. with the stirring speed maintained at about 600-800 rpm.

8. Into the mixture of the aqueous phase and the paraben phase was transferred the xanthan gum phase according to the percentage described in Table 10 and the resulting mixture was well stirred and maintained at about 65° C. to about 68° C. with the stirring speed maintained at about 600-800 rpm.

9. Preparation of the oil-in-water emulsion. Into the mixture of the aqueous phase, the paraben phase, and the xanthan Gum phase was transferred the oil phase according to the percentage described in Table 10. The resulting mixture was well stirred and maintained at about 65° C. to about 68° C. with the stirring speed maintained at about 600-800 rpm to form an oil-in-water emulsion.

10. The oil-in-water emulsion was cooled to about 38° C. to about 40° C.

11. Into the cooled oil-in-water emulsion was added phenoxyethanol according to the percentage described in Table 10. The temperature of resulting mixture was maintained at about 38° C. to about 40° C., and the stirring speed was maintained at about 600-800 rpm.

For the combination creams of ruxolitinib and calcipotriol (Formulations #3 and #6), calcipotriol solution in medium chain triglycerides, and light mineral oil were added into the oil-in-water emulsion according to the respective percentages described in Table 10. The resulting mixture was maintained at about 38° C. to about 40° C. with the stirring speed maintained at about 600-800 rpm. For ruxolitinib only creams (Formulation #1, #2, #4, and #5), medium chain triglycerides and light mineral oil were added into the oil-in-water emulsion according to the respective percentages described in Table 10. The resulting mixture was maintained at about 38° C. to about 40° C. with the stirring speed was maintained at about 600-800 rpm. After cooling down the resulting mixtures and stopping the stirring, the creams (Formulations #1 to #6) were formed and collected.

Table 9 lists weight percentages of different phases of the cream Formulations #1 to #6. Table 10 lists weight percentages of ruxolitinib phosphate, calcipotriol, and excipients in the cream Formulations #1 to #6.

TABLE 9

Weight percentages of different phases of the ruxolitinib creams (Formulations #1, #2, #4, and #5), and ruxolitinib and calcipotriol combination creams (Formulations #3 and #6). Note that ruxolitinib phosphate was in an amount of 1.98 wt % for Formulations #1 to #6, which corresponds to 1.5% w/w of ruxolitinib on a free base basis. The calcipotriol was in an amount of 0.005% w/w or 50 microgram/g for Formulation #3 and #6. Formulations #1, #2, #4 and #5 do not contain calcipotriol.

| Ingredient | Function | #1 (% w/w) | #2 (% w/w) | #3 (% w/w) | #4 (% w/w) | #5 (% w/w) | #6 (% w/w) |
|---|---|---|---|---|---|---|---|
| | | Aqueous Phase | | | | | |
| Purified water | | 55.42 | 53.42 | 55.42 | 55.42 | 53.42 | 55.42 |
| Disodium EDTA | Chelating agent | 0.05 | 0.05 | 0.05 | 0.05 | 0.05 | 0.05 |

TABLE 9-continued

Weight percentages of different phases of the ruxolitinib creams (Formulations #1, #2, #4, and #5), and ruxolitinib and calcipotriol combination creams (Formulations #3 and #6). Note that ruxolitinib phosphate was in an amount of 1.98 wt % for Formulations #1 to #6, which corresponds to 1.5% w/w of ruxolitinib on a free base basis. The calcipotriol was in an amount of 0.005% w/w or 50 microgram/g for Formulation #3 and #6. Formulations #1, #2, #4 and #5 do not contain calcipotriol.

| Ingredient | Function | #1 (% w/w) | #2 (% w/w) | #3 (% w/w) | #4 (% w/w) | #5 (% w/w) | #6 (% w/w) |
|---|---|---|---|---|---|---|---|
| PEG300 | Solvent | 7 | 7 | 7 | 0 | 0 | 0 |
| PEG400 | Solvent | 0 | 0 | 0 | 7 | 7 | 7 |
| Ruxolitinib phosphate | Active | 1.98 | 1.98 | 1.98 | 1.98 | 1.98 | 1.98 |
| Paraben Phase | | | | | | | |
| Propylene glycol | Solvent | 1.5 | 3.5 | 1.5 | 1.5 | 3.5 | 1.5 |
| Methylparaben | Antimicrobial preservative | 0.1 | 0.1 | 0.1 | 0.1 | 0.1 | 0.1 |
| Propylparaben | Antimicrobial preservative | 0.05 | 0.05 | 0.05 | 0.05 | 0.05 | 0.05 |
| Xanthan Gum Phase | | | | | | | |
| Propylene glycol | Solvent | 5 | 5 | 5 | 5 | 5 | 5 |
| Xanthan Gum | Stabilizing agent | 0.4 | 0.4 | 0.4 | 0.4 | 0.4 | 0.4 |
| Oil Phase | | | | | | | |
| White petrolatum | Occlusive agent | 7 | 7 | 7 | 7 | 7 | 7 |
| Light mineral oil | Emollient | 2 | 2 | 2 | 2 | 2 | 2 |
| Glycerol stearate SE | Emulsifier | 3 | 3 | 3 | 3 | 3 | 3 |
| Cetyl alcohol | Stiffening agent | 3 | 3 | 3 | 3 | 3 | 3 |
| Stearyl alcohol | Stiffening agent | 1.75 | 1.75 | 1.75 | 1.75 | 1.75 | 1.75 |
| Dimethicone | Emollient; Skin protectant | 1 | 1 | 1 | 1 | 1 | 1 |
| Medium chain triglycerides | Emollient | 2 | 2 | 2 | 2 | 2 | 2 |
| Polysorbate 20 | Emulsifier | 1.25 | 1.25 | 1.25 | 1.25 | 1.25 | 1.25 |
| Added into the oil-in-water emulsion at a lower temperature (38-40° C.) | | | | | | | |
| Phenoxyethanol | Antimicrobial preservative | 0.5 | 0.5 | 0.5 | 0.5 | 0.5 | 0.5 |
| Calcipotriol in medium chain triglycerides (1 mg/g) | Active | 0 | 0 | 5 | 0 | 0 | 5 |
| Medium chain triglycerides | Emollient | 5 | 5 | 0 | 5 | 5 | 0 |
| Light mineral oil | Emollient | 2 | 2 | 2 | 2 | 2 | 2 |

TABLE 10

Weight percentages of ruxolitinib phosphate, calcipotriol, and excipients for Formulations #1 to #6.

| Ingredient | #1 (% w/w) | #2 (% w/w) | #3 (% w/w) | #4 (% w/w) | #5 (% w/w) | #6 (% w/w) |
|---|---|---|---|---|---|---|
| Ruxolitinib phosphate | 1.98 | 1.98 | 1.98 | 1.98 | 1.98 | 1.98 |
| Calcipotriol | 0 | 0 | 0.005 | 0 | 0 | 0.005 |
| Purified water | 55.42 | 53.42 | 55.42 | 55.42 | 53.42 | 55.42 |
| Disodium EDTA | 0.05 | 0.05 | 0.05 | 0.05 | 0.05 | 0.05 |
| PEG300 | 7 | 7 | 7 | 0 | 0 | 0 |
| PEG400 | 0 | 0 | 0 | 7 | 7 | 7 |
| Propylene glycol | 6.5 | 8.5 | 6.5 | 6.5 | 8.5 | 6.5 |

TABLE 10-continued

Weight percentages of ruxolitinib phosphate, calcipotriol, and excipients for Formulations #1 to #6.

| Ingredient | #1 (% w/w) | #2 (% w/w) | #3 (% w/w) | #4 (% w/w) | #5 (% w/w) | #6 (% w/w) |
|---|---|---|---|---|---|---|
| Methylparaben | 0.1 | 0.1 | 0.1 | 0.1 | 0.1 | 0.1 |
| Propylparaben | 0.05 | 0.05 | 0.05 | 0.05 | 0.05 | 0.05 |
| Xanthan Gum | 0.4 | 0.4 | 0.4 | 0.4 | 0.4 | 0.4 |
| White petrolatum | 7 | 7 | 7 | 7 | 7 | 7 |
| Light mineral oil | 4 | 4 | 4 | 4 | 4 | 4 |
| Glycerol stearate SE | 3 | 3 | 3 | 3 | 3 | 3 |
| Cetyl alcohol | 3 | 3 | 3 | 3 | 3 | 3 |
| Stearyl alcohol | 1.75 | 1.75 | 1.75 | 1.75 | 1.75 | 1.75 |
| Dimethicone | 1 | 1 | 1 | 1 | 1 | 1 |
| Medium chain triglycerides | 7.0 | 7.0 | 6.995 | 7.0 | 7.0 | 6.995 |
| Polysorbate 20 | 1.25 | 1.25 | 1.25 | 1.25 | 1.25 | 1.25 |
| Phenoxyethanol | 0.5 | 0.5 | 0.5 | 0.5 | 0.5 | 0.5 |

Figure 5:
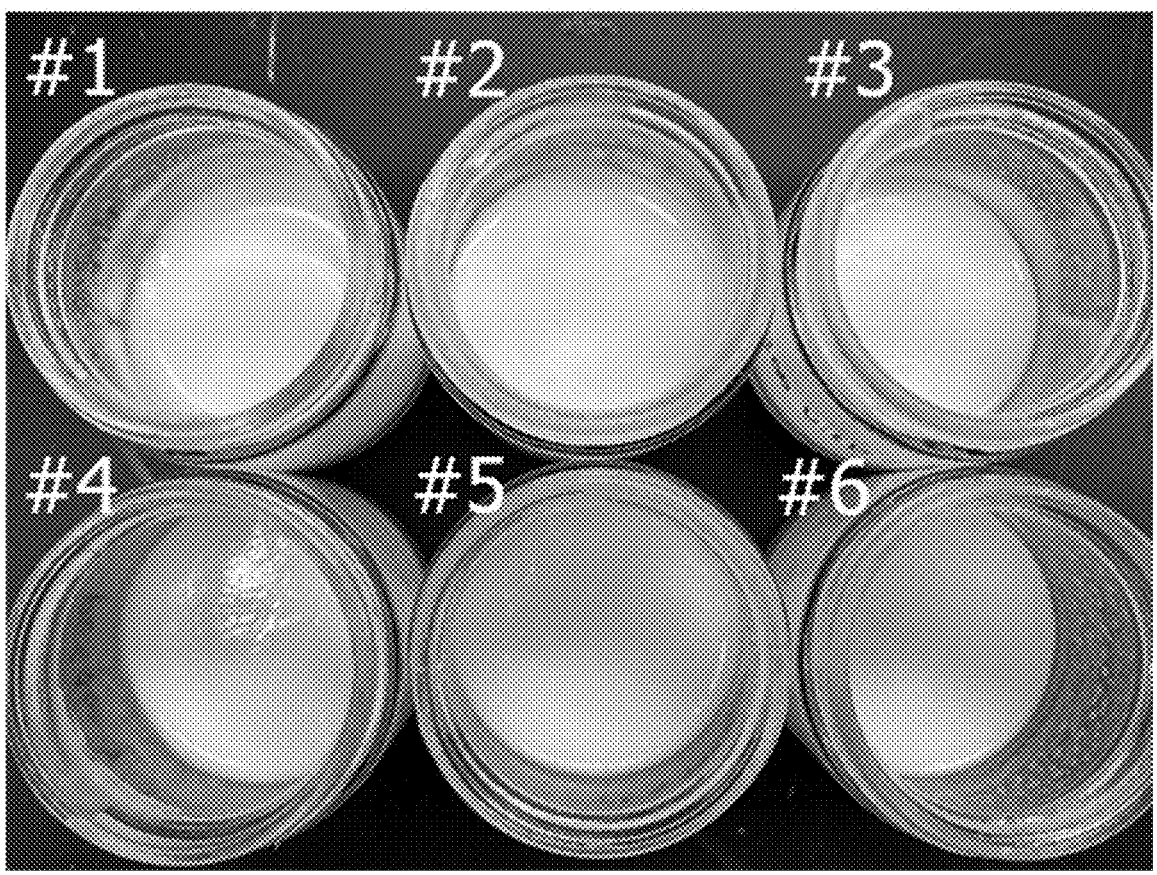
FIG. 5 depicts photograph of cream formulations #1 to #6.

The cream forms of Formulations #1 to #6 are as shown in FIG. 5. Cream Formulations #1 to #3 contained 7.0% w/w of PEG 300; while cream Formulations #4 to #6 contained 7.0% w/w of PEG400. The propylene glycol content in the cream Formulation #1, #3, #4, and #6 was 6.5% w/w, while the propylene glycol content in the cream Formulations #2 and #5 was 8.5% w/w. ruxolitinib content was 1.5% w/w on a free base basis in all the cream Formulations #1 to #6. Formulation #3 and #6 are ruxolitinib and calcipotriol combination creams containing both ruxolitinib (1.5% w/w on a free base basis) and calcipotriol (0.005% w/w).

An additional formulation (Formulation #7) containing 1.1% w/w of ruxolitinib on a free base basis and 0.0005 w/w of calcipotriol was prepared.

For preparations of ruxolitinib and calcipotriol combination creams, ruxolitinib was incorporated in the water phase, and calcipotriol was dissolved in the liquid oil phase upon heating, solid oil phase excipients were heated to melt, and then the water phase, the liquid oil phase and the melted solid oil phase excipients were combined and homogenized to produce a formulation, which was then cooled. To the cooled formulation, was added the antimicrobial preservative and the resulting formulation was stirred until visually homogeneous, of which the pH was adjusted if necessary and to which was added water to make up the volume as needed. Details of the preparation steps are as follows:

(i) EDTA was initially added to the water in an amber Duran and stirred at 500 RPM until visually homogenous.

(ii) BHA was initially added to the Transcutol P in an amber Duran and stirred at 500 RPM until visually homogeneous.

(iii) The solutions from Step (i) and (ii) were added to the rest of the aqueous phase excipients (glycerol) in an amber Duran and stirred by magnetic stirrer bar at 500 RPM until visually homogenous.

(iv) Ruxolitinib phosphate was added to the aqueous phase from Step (iii) and stirred for 5 mins at 500 RPM, ruxolitinib phosphate does not fully dissolve in this step.

(v) The suspension from Step (iv) was pH adjusted to pH 6.0-7.0 with trolamine, and ruxolitinib phosphate dissolved during this step.

(vi) In a separate amber Duran, BHT was added to oleyl alcohol and sweet almond oil and placed on stir at 250 RPM until visually homogenous.

(vii) The solution from Step (vi) was added to the remaining liquid oil phase excipients (polysorbate 80 and light mineral oil) and stirred for 3-5 mins at 500 RPM until visually homogenous.

(viii) Calcipotriol was added to the liquid oil phase from Step (vii) and stirred at 500 RPM at 65° C. for 1 hour, and then at ambient laboratory temperature overnight, to dissolve.

(ix) Following calcipotriol dissolution in Step (viii) poloxamer 407 was dispersed into the solution from Step (viii) by stirring at 500 RPM.

(x) The solid oil phase excipients were weighed into a separate amber Duran placed in a water bath at 70° C. until molten. The aqueous phase from Step (v), liquid oil phase from Step (ix) and the homogeniser head (silverson, square hole, high shear screen) were also placed in the water bath for 3 mins.

(xi) The phases were combined and homogenized for 2 mins at 10,000 RPM.

(xii) The formulation from Step (xi) was stirred using an IKA anchor paddle at 100 RPM until the formulation had cooled to ambient laboratory temperature.

(xiii) Phenoxyethanol was added to the formulation from Step (xii) and hand stirred until visually homogenous.

(xiv) The pH of the formulation was checked, adjusted if necessary, made to volume with water and further hand stirred until visually homogenous.

Table 11 lists weight percentages for Formulation #7.

TABLE 11

Composition of Cream Formulation #7. Note that ruxolitinib phosphate was in an amount of 1.464 wt %, which corresponds to 1.1% w/w of ruxolitinib on a free base basis. The calcipotriol was in an amount of 0.005% w/w.

| Excipient | % w/w | Functionality |
|---|---|---|
| Aqueous Phase | | |
| Purified Water | 32.021 | Solvent |
| Edetate disodium (EDTA) | 0.050 | Chelating agent |
| Butylhydroxyanisole (BHA) | 0.020 | Antioxidant |
| Transcutol P | 16.090 | Solvent/Solubilizer |
| Glycerol | 8.045 | Humectant |
| Ruxolitinib Phosphate | 1.464 (1.1% on free base basis) | API |
| Trolamine[1] | to pH 6.0-7.0 | Buffering agent |
| Oil Phase | | |
| Butylhydroxytoluene (BHT) | 0.500 | Antioxidant |
| Oleyl Alcohol | 5.000 | Emulsifying agent |
| Sweet Almond Oil | 2.000 | Emollient |

TABLE 11-continued

Composition of Cream Formulation #7. Note that ruxolitinib phosphate was in an amount of 1.464 wt %, which corresponds to 1.1% w/w of ruxolitinib on a free base basis. The calcipotriol was in an amount of 0.005% w/w.

| Excipient | % w/w | Functionality |
|---|---|---|
| Polysorbate 80 | 2.011 | Surfactant |
| Light Mineral Oil | 10.000 | Emollient, Solvent |
| Calcipotriol Monohydrate | 0.0052 | API |
| Poloxamer 407 | 1.000 | Surfactant/Stabilizer |
| Cetosteryl Alcohol | 12.000 | Stiffening agent, consistency improver |
| Cetomacrogol 1000 | 1.962 | Emulsifier/Surfactant |
| Arlacel 165 (Glyceryl Stearate (and) PEG-100 Stearate) | 2.538 | Emulsifier |
| Added after cooling | | |
| Phenoxyethanol | 1.000 | Preservative |
| Trolamine | to pH 6.5-7.0[1] | Buffering agent |
| Phosphoric acid | | Buffering agent |
| Purified Water | Q.S to 100% | Solvent |
| Total | 100.000 | |

[1]Trolamine and phosphoric acid may be used to adjust the pH and additional water may be added to make up 100 w/w % for Formulation #7.

Example 4. Ruxolitinib and Calcipotriol Combination Creams with Other Excipient Concentrations Cream formulations are prepared as described in Example 3 having ruxolitinib phosphate present in an amount of about 0.75% w/w on a free base basis with adjustments to the water percentage in Example 3 as necessary.

Cream formulations are prepared as described in Example 3 with propylene glycol of about 6.5% w/w to about 15% w/w (e.g., about 6.5% w/w, about 7% w/w, about 7.5% w/w, about 8% w/w, about 8.5% w/w, about 9% w/w, about 9.5% w/w, about 10% w/w, about 10.5% w/w, about 11% w/w, about 11.5% w/w, about 12% w/w, about 12.5% w/w, about 13% w/w, about 13.5% w/w, about 14% w/w, about 14.5% w/w or about 15% w/w) with adjustments to the water percentage in Example 3 as necessary.

Cream formulations are prepared as described in Example 3 with various low molecular weight polyethylene glycols (PEGs) as co-solvent, including PEG200, PEG300, PEG400, or a combination thereof.

Cream formulations are prepared as described in Example 3 with methylparaben content ranging between 0 and about 0.1% w/w, and with propylparaben content from 0 to about 0.05% w/w (with adjustments to the water percentage in Example 3 as necessary).

Cream formulations are prepared as described in Example 3 with the xanthan gum content from about 0.2 to about 0.6% w/w can be prepared (with adjustments to the water percentage in Example 3 as necessary).

Cream formulations are prepared as described in Example 3 with butylated hydroxytoluene (BHT), butylated hydroxyanisole (BHA), and tocopherol, used either alone or in combination, added to the oil phase (with adjustments to the water percentage in Example 3 as necessary.

Cream formulations are prepared as described in Example 3 with ascorbyl palmitate, ascorbic acid, or citric acid, or a combination thereof, added to enhance the stability of calcipotriol.

Figure 10:
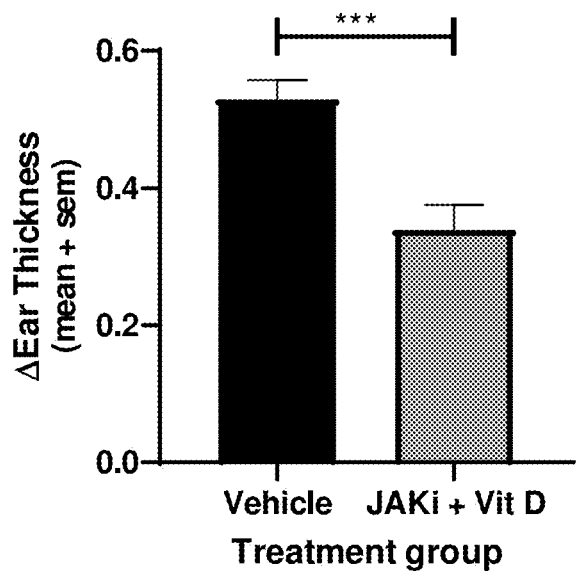
FIG. 10 depicts the change in ear thickness in an IL-23 induced psoriasis-like in vivo mouse model with treatment with vehicle or a combination cream of ruxolitinib and calcipotriol (*** indicates a p<0.001) (JAKi is ruxolitinib; Vit D is calcipotriol; and Combo is a combination of ruxolitinib and calcipotriol).

Example 5. Ruxolitinib and Calcipotriol Combination Creams in a Murine Model of IL-23 Induced Psoriasis-Like Disease A combination cream formulation (Formulation #7 of Example 3) was tested in established murine model of IL-23 induced psoriasis-like disease (Rizzo H L, et al., "IL-23-mediated psoriasis-like epidermal hyperplasia is dependent on IL-17A," *J Immunol* 186:1495-1502 (2011); T. P. Singh, et al., "IL-23- and Imiquimod-induced models of experimental psoriasis in mice," *Curr. Protoc. Immunol.* e71, (2019); 10.1002/cpim.71), including acanthosis and accumulation of inflammatory cells in both the epidermis and dermis leading to local thickening of skin. IL-23 was intradermally injected to one ear on Day 0, 2, 4 and Day 7. Topical cream vehicle or Formulation #7 (Example 3) were topically applied to one ear of IL-23-induced psoriasis like mice. Cream (20 ug per application) was applied twice per day (B.I.D) for 8 days. Ears were measured by engineer's calipers for swelling. A statistically significant decrease in ear thickening (p<0.001) was measured in mice treated with Formulation #7 compared to vehicle treated mice (FIG. 10).

Various modifications of the presently claimed subject matter, in addition to those described herein, will be apparent to those skilled in the art from the foregoing description. Such modifications are also intended to fall within the scope of the appended claims. Each reference cited in the present disclosure, including all patent, patent applications, and publications, is incorporated herein by reference in its entirety.

What is claimed is:

1. A pharmaceutical formulation for topical treatment of a skin disease, comprising (a) a JAK inhibitor, or a pharmaceutically acceptable salt thereof, and (b) a vitamin D3 analog, or a pharmaceutically acceptable salt thereof, wherein the JAK inhibitor, or a pharmaceutically acceptable salt thereof, is a JAK1/2 inhibitor, which is ruxolitinib, or a pharmaceutically acceptable salt thereof; and the vitamin D3 analog, or a pharmaceutically acceptable salt thereof, is a compound of Formula (II):

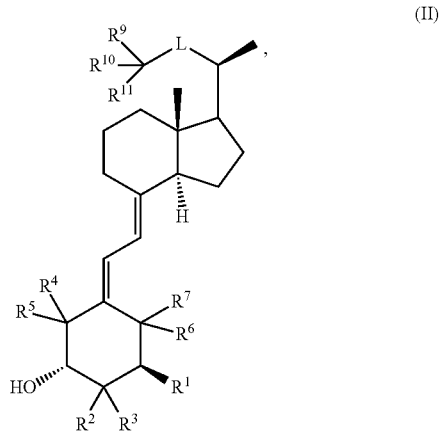

wherein:
$R^1$ is H or OH;
$R^2$ and $R^3$ are each H; or
$R^2$ is O—$R^{2A}$; and $R^3$ is H; or
$R^2$ and $R^3$ are taken together to form a =CH$_2$ group;
$R^{2A}$ is —C$_{1-4}$ alkylene-OH;
$R^4$ and $R^5$ are each H; or R⁴ and R⁵ are taken together to form a =CH₂ group;
R⁶ and R⁷ are each H; or
R⁶ and R⁷ are taken together to form a =CH₂ group;
L is —CH₂—CH₂—CH(R¹²)—, —CH₂—CH₂—CH₂—CH(R¹²)—, —CH=CH—CH(R¹²)—, —CH=CH—CH=CH—, —CH₂—C≡C—, —O—CH₂—CH₂—, or —O—CH₂—CH₂—CH₂—, wherein R¹² is H or OH;
R⁹ is $C_{1-3}$ alkyl or $C_{1-4}$ haloalkyl;
R¹⁰ is $C_{1-3}$ alkyl or $C_{1-4}$ haloalkyl;
R¹¹ is H or OH;
or, alternatively, R⁹ and R¹⁰ together with the carbon atom to which they are attached form a $C_{3-4}$ cycloalkyl ring; and
R¹¹ is H.

2. The pharmaceutical formulation of claim 1, wherein the JAK1/2 inhibitor, or a pharmaceutically acceptable salt thereof, is ruxolitinib phosphate.

3. The pharmaceutical formulation of claim 1, wherein the vitamin D3 analog, or a pharmaceutically acceptable salt thereof, is calcipotriol or maxacalcitol, or a pharmaceutically acceptable salt thereof.

4. The pharmaceutical formulation of claim 1, wherein the JAK1/2 inhibitor is ruxolitinib, or a pharmaceutically acceptable salt thereof, and the vitamin D3 analog is calcipotriol.

5. The pharmaceutical formulation of claim 1, wherein the JAK1/2 inhibitor is ruxolitinib, or a pharmaceutically acceptable salt thereof, and the vitamin D3 analog is maxacalcitol.

6. The pharmaceutical formulation of claim 1, wherein the formulation comprises from about 0.05% to about 3.0% or about 0.05% to about 1.5% w/w of the ruxolitinib, or a pharmaceutically acceptable salt thereof, on a free base basis.

7. The pharmaceutical formulation of claim 1, wherein the formulation comprises about 0.05%, about 0.06%, about 0.07%, about 0.08%, about 0.09%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1.0%, about 1.05%, about 1.1%, about 1.15%, about 1.2%, about 1.25%, about 1.3%, about 1.35%, about 1.4%, about 1.45%, about 1.5%, about 1.55%, about 1.6%, about 1.65%, about 1.7%, about 1.75%, about 1.8%, about 1.85%, about 1.9%, about 1.95%, about 2.0%, about 2.5%, or about 3.0% by weight of the formulation on a free base basis of the ruxolitinib, or the pharmaceutically acceptable salt thereof.

8. The pharmaceutical formulation of claim 1, wherein the formulation comprises from about 0.0001% w/w to about 0.01% w/w of the vitamin D3 analog, or a pharmaceutically acceptable salt thereof, on a free base basis.

9. The pharmaceutical formulation of claim 1, wherein the formulation comprises from about 0.0001% w/w to about 0.005% w/w of the vitamin D3 analog, or a pharmaceutically acceptable salt thereof, on a free base basis.

10. The pharmaceutical formulation of claim 1, wherein the formulation comprises from about 0.0001% w/w to about 0.01% w/w or from about 0.0001% w/w to about 0.005% w/w of the vitamin D3 analog, or a pharmaceutically acceptable salt thereof, on a free base basis.

11. The pharmaceutical formulation of claim 1, wherein the formulation comprises about 0.005% w/w of the vitamin D3 analog, or a pharmaceutically acceptable salt thereof, on a free base basis.

12. The pharmaceutical formulation of claim 1, wherein the formulation is a cream or a lotion.

13. The pharmaceutical formulation of claim 1, wherein the formulation is an oil-in-water emulsion.

14. The pharmaceutical formulation of claim 1, wherein the formulation comprises water, an oil component, and an emulsifier or stabilizer component.

15. The pharmaceutical formulation of claim 14, wherein the water comprises from about 5% to about 90%, from about 10% to about 80%, from about 10% to about 70%, from about 10% to about 60%, about 20% to about 70%, about 20% to about 60%, or from about 20% to about 50% by weight of the pharmaceutical formulation.

16. The pharmaceutical formulation of claim 14, wherein the oil component comprises from about 5% to about 90%, from about 5% to about 80%, from about 5% to about 70%, from about 5% to about 60%, from about 5% to about 50%, or from about 5% to about 40% by weight of the pharmaceutical formulation.

17. The pharmaceutical formulation of claim 14, wherein the emulsifier or stabilizer component comprises from about 1% to about 30% or from about 5% to about 25% by weight of the pharmaceutical formulation.

18. The pharmaceutical formulation of claim 14, further comprising a solvent component for dissolving ruxolitinib, or a pharmaceutically acceptable salt thereof.

19. The pharmaceutical formulation of claim 18, wherein the solvent component comprises from about 5% to about 20%, from about 2% to about 30%, from about 5% to about 30%, from about 5% to about 25%, from about 5% to about 20%, or from about 10% to about 20% by weight of the pharmaceutical formulation.

20. The pharmaceutical formulation of claim 1, wherein the formulation has a pH of from about 6.0 to about 8.0, from about 6.5 to about 7.5, or from about 6.5 to about 7.0.

21. The pharmaceutical formulation of claim 20, wherein pH of the formulation is adjusted with trolamine.

* * * * *